United States Patent [19]

Lutz et al.

[11] 4,251,264

[45] Feb. 17, 1981

[54] 2,6-DINITROANILINE HERBICIDES

[75] Inventors: Albert W. Lutz, Princeton; Robert E. Diehl, Lawrenceville, both of N.J.

[73] Assignee: American Cyanamid Company, Stamford, Conn.

[21] Appl. No.: 1,624

[22] Filed: Jan. 8, 1979

Related U.S. Application Data

[60] Division of Ser. No. 777,271, Mar. 11, 1977, Pat. No. 4,165,231, which is a continuation-in-part of Ser. No. 639,729, Dec. 11, 1975, abandoned, which is a division of Ser. No. 538,980, Jan. 6, 1975, Pat. No. 4,066,441, which is a division of Ser. No. 323,000, Jan. 12, 1973, Pat. No. 3,920,742, which is a continuation-in-part of Ser. No. 262,807, Jun. 14, 1972, abandoned, which is a continuation-in-part of Ser. No. 174,938, Aug. 25, 1971, abandoned.

[51] Int. Cl.³ .................................. A01N 37/34
[52] U.S. Cl. .................................. 71/105
[58] Field of Search .................................. 71/105

[56] References Cited

U.S. PATENT DOCUMENTS

| | | | |
|---|---|---|---|
| 3,257,190 | 6/1966 | Soper | 71/121 |
| 3,332,769 | 7/1967 | Soper | 71/121 |
| 3,672,866 | 6/1972 | Damian | 71/121 |
| 3,726,923 | 4/1973 | Foster | 71/121 |
| 3,764,624 | 10/1973 | Strong | 71/121 |

*Primary Examiner*—Glennon H. Hollrah
*Attorney, Agent, or Firm*—H. G. Jackson

[57] ABSTRACT

The invention is the use of substituted 2,6-dinitroaniline compounds as preemergence herbicides and compositions employing the substituted 2,6-dinitroaniline compounds.

7 Claims, No Drawings

2,6-DINITROANILINE HERBICIDES

This is a division of Ser. No. 777,271 filed Mar. 11, 1977 now U.S. Pat. No. 4,165,231 (1979) which is a continuation-in-part of Ser. No. 639,729 filed Dec. 11, 1975 now abandoned which is a division of Ser. No. 538,980 filed Jan. 6, 1975 now U.S. Pat. 4,066,441 (1978) which is a division of Ser. No. 323,000 filed Jan. 12, 1973 now U.S. Pat. No. 3,920,742 (1975) which is a continuation-in-part of Ser. No. 262,807 filed June 14, 1972 now abandoned which is a continuation-in-part of Ser. No. 174,938 filed Aug. 25, 1971 now abandoned.

The invention is the use of substituted 2,6-dinitroaniline compounds as preemergence herbicides and herbicidal compositions employing the substituted 2,6-dinitroaniline compounds.

The 2,6-dinitroaniline compounds useful in the invention may be represented by the following structural formula:

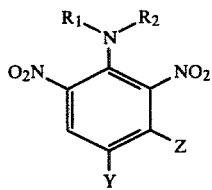

wherein,

Y is halogen, alkyl $C_1C_4$, alkenyl $C_2-C_4$, CN, $-SO_2NR_3R_4$ or $CF_3$;

Z is alkyl $C_1-C_4$, alkenyl $C_2-C_4$ or mono-substituted alkyl $C_1-C_4$ where the substituent is halogen, alkoxy $C_1-C_4$ or $-NR_3R_4$;

$R_1$ is hydrogen, alkyl $C_1-C_6$, alkenyl $C_2-C_6$ or alkynyl $C_2-C_6$;

$R_2$ is alkyl $C_2-C_7$ (straight, branched or cyclo), alkenyl $C_2-C_6$, alkynyl $C_2-C_6$, or mono-substituted alkyl $C_1-C_4$ where the substituent is halogen or alkoxy $C_1-C_4$;

$R_3$ and $R_4$ each are hydrogen or alkyl $C_1-C_4$ and when $R_1$ and $R_2$ are taken together they represent piperidino, pyrrolidino or morpholino;

with the proviso that when Y and Z are methyl and $R_1$ is hydrogen or ethyl, then $R_2$ cannot be ethyl; and that when $R_1$ is hydrogen and Y and Z are methyl, $R_2$ cannot be 1-ethylbutyl, 1-ethylpropyl, 1-methylpropyl or 1-methylbutyl.

Illustrative lower alkyl substituents are methyl, ethyl, n-propyl, iso-propyl, n-butyl, t-butyl, n-pentyl, n-hexyl, 2-pentyl, 3-pentyl, sec-butyl, and the like.

Illustrative loweralkenyl substituents are ethenyl, 1-propenyl, 2-propenyl, 1-butenyl, 2-butenyl, 3butenyl, 1-pentenyl, 1-hexenyl, and the like.

Illustrative loweralkynyl substituents are ethynyl, 1-propynyl, 2-propynyl, 1-butynyl, 2-butynyl, 3-butynyl, 1-pentynyl, 1-hexynyl, and the like.

Illustrative cyclic hydrocarbons are cyclopropyl, cyclobutyl, cyclopentyl, and cyclohexyl groups.

Illustrative halogen substituents are fluoro, chloro, bromo and iodo groups.

The above-identified compounds are highly effective herbicidal agents and particularly efficacious are those represented by the following structural formula:

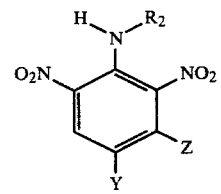

wherein,

Y is $CH_3$, $C_2H_5$, $C_3H_7$-n, $C_3H_7$-i, $C_4H_9$-i; sec-$C_4H_9$, $CF_3$ or Cl, Z is $CH_3$, $CH_2OCH_3$ or $-CH(CH_3)OCH_3$; $R_2$ is $C_3-C_7$ secondary alkyl free from quaternary carbon atoms or monochloroalkyl $C_3-C_4$; with the proviso that when Z and Y are each methyl, $R_2$ is a member other than sec-butyl, 2-pentyl, 3-pentyl or 3-hexyl. These compounds represent a preferred class of compounds within the above-broader generic class and show a marked superiority in herbicidal performance.

The preferred compounds can be divided into 2 groups, i.e., (a) compounds of Formula II, wherein $R_2$ is $C_3-C_7$ secondary-alkyl free from quaternary carbon atoms or monochloro ($C_3-C_4$) alkyl; Y is $CH_3$, $C_2H_5$, $C_3H_7$-n, $C_3H_7$-i, $C_4H_9$-i, sec-$C_4H_9$ or Cl; and Z is $-CH_2OCH_3$ or $-CH(CH_3)OCH_3$ and (b) compounds of formula II wherein $R_2$ is $C_3H_7$ sec-alkyl free from quaternary carbon atoms or monochloro ($C_3-C_4$) alkyl; Y is $CH_3$, $C_2H_5$, $C_3H_7$-i, $C_3H_7$-n, $C_4H_9$-i, sec-$C_4H_9$, Cl or $CF_3$; and Z is $CH_3$; with the proviso that when Z and Y are each methyl, $R_2$ represents a member other that sec-butyl, 2-pentyl, 3-pentyl or 3-hexyl.

The herbicidal methods of the invention comprise application of a herbicidally effective amount of one or more compounds above to the soil containing the seeds or propagating organs of undesirable plant species to be controlled.

Wherein an asymmetric carbon atom exists in the dinitroaniline compounds above, optical isomerism may exist. Accordingly, such compounds may be employed as separate antimers or in admixture, as in a racemix composition. Unless there is indication to the contrary by reference to such a compound, the unresolved composition is intended herein. Separation of antimers, where desired, may be effected by conventional resolution techniques. A convenient method relates to the introduction of an optically active substituent, such as a (-)-sec-butylamino group into the ring system, as by nucleophilic substitution, as exemplified below.

Preferably, application of these compounds or active ingredients is made using the herbicidal compositions described below with conventional application methods.

The 2,6-dinitroaniline compounds are prepared by a nucleophilic substitution of a 1-substituent, such as, a chloro group, with the appropriately substituted amine. While chloro is a preferred substituent, and the discussion is in terms thereof other conventional equivalent substituents, such as, bromo or iodo are included herein. The displacement may be conducted with or without an organic solvent, such as toluene, benzene or preferably xylene.

The reaction, which is graphically illustrated below, is carried out by heating the reactants, preferably between 50° C. and 150° C.

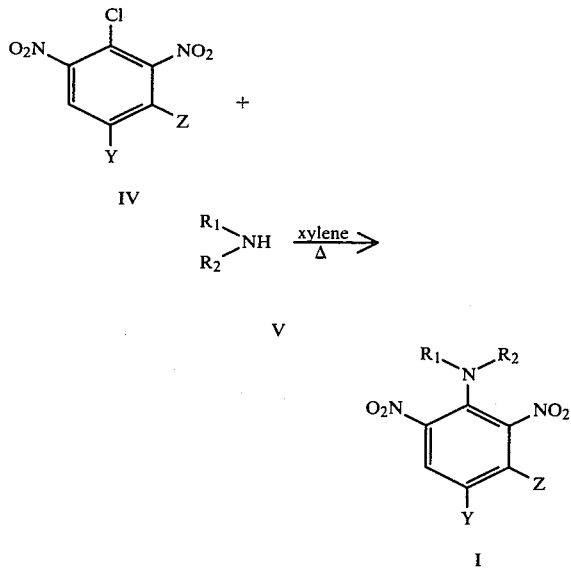

For purposes of further discussion, the active ingredients may be considered as falling into one of six classes of compounds, labeled as Types A through F. In Type A compounds, Y is alkyl $C_1$-$C_4$. In Type B compound, Y is alkenyl $C_2$-$C_4$. In Type C compounds, Y is halogen and preferably chlorine or bromine. In Type D compounds, Y is -$SO_2NR_3R_4$, where $R_3$ and $R_4$ are as described above. In Type E compounds, Y is trifluoromethyl. In Type F compounds, Y is CN.

Type A compounds, where Y and Z are lower alkyl groups, can be prepared by reacting the appropriately substituted 2,6-dinitrochlorobenzene with the appropriate amine.

The chlorobenzene intermediates for Type A compounds can be prepared by reacting an appropriately substituted aniline with ethyl chloroformate in benzene at about 10° C. to 50° C. to yield the correspondingly substituted N-(ethoxycarbonyl)-3,4-substituted aniline. This product is then treated with a cold solution of sulfuric and nitric acid, i.e., at about 0° C. to 20° C. to obtain the N-(ethoxycarbonyl)-3,4-disubstituted-2,6dinitroaniline. Reaction of the thus-formed product with sulfuric acid at an elevated temperature, preferably between about 100° C. and 150° C., converts the N-(ethoxycarbonyl) product to the 3,4-disubstituted-2,6dinitroaniline. The amino group is replaced by a chlorine atom by first heating the compound with glacial acetic acid and diazotizing the amine with a mixture of sodium nitrite in sulfuric acid. This is followed by treating the diazotized mixture with a mixture of cuprous chloride in hydrochloric acid, and then heating the thus-formed mixture to about 40° C. to 80° C. to obtain the chlorinated compound.

Selected chlorinated intermediates for Type A compounds can also be prepared by reacting a mixture of fuming sulfuric acid and fuming nitric acid with 4-chloro-o-xylene at about 10° C. to 60° C., pouring the mixture over ice and separating the precipitated solid. Recrystallization of the solid from methanol or other lower alkyl alcohol $C_1$-$C_4$ yields the high purity product.

Illustrative Type A compounds which are readily prepared by the preceding procedure include, for example:
3,4-dimethyl-2,6-dinitro-N,N-di-n-propylaniline;
N-ethyl-N-n-propyl-3,4-dimethyl-2,6-dinitroaniline;
N,N-di-n-butyl-3,4-dimethyl-2,6-dinitroaniline;
3,4-dimethyl-2,6-dinitro-N-oxydiethyleneaniline;
3,4-dimethyl-2,6-dinitro-N-pentamethyleneaniline;
3,4-dimethyl-2,6-dinitro-N-tetramethyleneaniline;
N,N-dicyclopropyl-3,4-dimethyl-2,6-dinitroaniline;
N,N-diallyl-3,4-dimethyl-2,6-dinitroaniline;
N-ethyl-N, 3,4-trimethyl-2,6-dinitroan-iline;
N,3,4-trimethyl-2,6-dinitro-N-(cyclopropyl)aniline;
N,N-dipropargyl-3,4-dimethyl-2,6-dinitroaniline;
N,N-bis(1-buten-3-yl)-3,4-dimethyl-2,6-dinitroaniline;
N-ethyl-3-isopropyl-4-methyl-2,6-dinitroaniline;
3-sec-butyl-4-methyl-2,6-dinitro-N,N-dimethylaniline;
N,N-3,4-tetramethyl-2,6-dinitroaniline;
N,N-diethyl-3,4-dimethyl-2,6-dinitroaniline;
N,3,4-trimethyl-2,6-dinitro-N-propylaniline;
N-cyclobutyl-N,3,4-trimethyl-2,6-dinitroaniline;
3,4-dimethyl-2,6-dinitro-N,N-(dicyclopropylmethyl)aniline;
3,4-dimethyl-2,6-dinitro-N-(cyclopropyl)aniline;
N-isopropyl-3,4-dimethyl-2,6-dinitroaniline;
N-allyl-3,4-dimethyl-2,6-dinitroaniline;
N-n-butyl-3,4-dimethyl-2,6-dinitroaniline;
N-sec-butyl-3,4-dimethyl-2,6-dinitroaniline;
3,4-dimethyl-2,6-dinitro-N-3-pentylaniline;
(1-ethylpropyl)-3-(methoxymethyl)-4-methyl-2,6-dinitroaniline;
(1-methylpropyl-3-ethoxymethyl)-4-ethyl-2,6-dinitroaniline;
(1-methylethyl)-3-(aminomethyl)-4-isopropyl-2,6-dinitroaniline and (1-ethylpropyl)-3-[(dimethylamino)methyl]-4-methyl-2,6dinitroaniline.

The 3,4-diethyl derivatives, 3-methyl-4-ethyl derivatives, 3-ethyl-4-methyl, 3-ethyl-4-propyl, 3,4-diisopropyl, 3,4di-n-propyl, 3,4-di-n-butyl, 3,4-diisobutyl, 3-propyl-4-butyl, and 3-methyl-4-isopropyl derivatives of the above-named 2,6-dinitroanilines, are likewise prepared by the above procedure, utilizing the appropriate 3,4-disubstituted-2,6-dinitrochlorobenzene and appropriate amine.

Type B compounds, where Y represents a lower alkenyl $C_2$-$C_4$ group, are prepared by the procedure described above. The reaction is preferably run in xylene at a temperature between about 50° C. and 150° C. and involves the reaction of a 3-substituted-4-alkenyl-2,6-dinitrochlorobenzene with the appropriate amine. In this reaction, Z is preferably methyl or ethyl, although it may be any of the radicals previously described for it.

Illustrative Type B compounds, which can be prepared by this procedure include, for example:
N-sec-butyl-4-isobutenyl-3-methyl-2,6-dinitroaniline;
4-isopropenyl-3-methyl-2,6-dinitro-N,N-di-n-propylaniline;
N,3-di-methyl-2,6-dinitro-4-n-propenylaniline; and
4-isopropenyl-N,N,3,5-tetramethyl-2,6-dinitroaniline.

A preferred method for the preparation of Type C compounds wherein Y is halogen and Z is lower alkyl involves the reaction of a dihalo-dinitroalkylbenzene, such as 3,6-dihalo-2,4-dinitrotoluene, with the appropriate amine. The reaction is preferably carried out in the presence of an organic solvent, such as $C_1$-$C_4$ alcohols, toluene and the like. The reaction may be conducted at room temperature, although heating is generally advantageously employed.

Type C compounds having the following structure may be prepared by the process described in *Chemical Abstracts* 44: 1433 g; 66; 109, 220 K and 54: 9921 c:

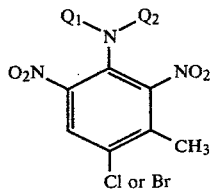

where $Q_1$ and $Q_2$ are hydrogen or methyl.

Type D compounds, in which Y represents an -$SO_2NR_3R_4$ group, can be synthesized by reacting, at an elevated temperature, a 1-chloro-3-substituted-2,6-dinitro-4 sulfonamide or alkyl-substituted sulfonamide with an amide, preferably in an organic solvent, such as xylene, toluene or the like. The intermediates for this reaction can be prepared by reacting-m-chlorotoluene with sulfuric acid and potassium nitrate to form the potassium 4-chloro-3,5-dinitro-o-toluenesulfonate which is converted to the corresponding o-toluenesulfonyl chloride by reaction with phosphorus pentachloride and phosphorus oxychloride. The thus-formed toluenesulfonyl chloride is then treated with ammonia, alkylamine or dialkylamine in acetone at 0° C. to 25° C. to obtain the corresponding o-toluenesulfonamide. Treatment of this product with the appropriate amine (i.e.,

where $R_1$ and $R_2$ are as described above) then yields the 4-sulfamoyl or alkyl-substituted sulfamoyl-2,6-dinitroaniline of this invention.

Illustrative Type D compounds which can be prepared by the process of the instant invention are:
  3-methyl-2,6-dinitro-$N^4$,$N^4$-di-n-propyl-4-sulfamoylaniline;
  $N^4$-sec-butyl-3-methyl-4-(methylsulfamoyl)-2,6-dinitroaniline;
  4-(dimethylsulfamoyl)-3-methyl-2,6-dinitro-$N^4$-3-pentylaniline;
  $N^4$,3-dimethyl-2,6-dinitro-4-sulfamoylaniline;
  3-methyl-$N^4$-oxydiethylene-2,6-dinitro-4-sulfamoylaniline;
  3-methyl-4-(methylsulfamoyl)-2,6-dinitro-$N^4$-pentamethyleneaniline;
  3,5-dimethyl-4-(methylsulfamoyl)-2,6-dinitro-$N^4$-tetramethyleneaniline.

Type E compounds can be prepared by reacting the appropriate 3-substituted-4-trifluoromethyl-2,6-dinitrochlorobenzene with the appropriate amine, preferably by heating the reactants in the presence of an organic solvent such as benzene, toluene or the like.

Preparation of chlorobenzene intermediates for use in this reaction are described by Newman and Pinkus, *Journal of Organic Chemistry* 19; 978, and Von Auwers and Julicker, *Chemische Berichte* 55: 2167 (1922). For example, 4-methylphenol may be treated with aluminum trichloride in carbon tetrachloride to obtain 2,5-cyclohexadiene-1-one which is treated with phosphoruspentachloride to yield 3-methyl-4-trichloromethylchlorobenzene. When the latter compound is treated with $SbF_3$, 1-chloro-3-methyl-4-(trifluoromethyl)-benzene is obtained. This product may be nitrated using a mixture of nitric acid and sulfuric acid to give the intermediate, 1-chloro-3-methyl-2,6-dinitro-4-(trifluoromethyl)-benzene.

Illustrative Type E compounds which can be prepared by this process include, for example:
  3-methyl-2,6-dinitro-N,N-di-n-propyl-4-(trifluoromethyl) aniline;
  N-sec-butyl-3-methyl-2,6-dinitro-4-(trifluoromethyl)aniline;
  3-methyl-2,6-dinitro-N-3-pentyl-4-(trifluoromethyl)aniline;
  N-cyclopropyl-3-methyl-2,6-dinitro-4-(trifluoromethyl)aniline;
  and 3-ethyl-2,6-dinitro-N-isopropyl-4-(trifluoromethyl)-aniline.

Type F compounds are prepared by reacting the appropriate 3,5-disubstituted-4-cyano-2,6-dinitrochlorobenzene with the appropriate amine.

o-Toluoyl chlorides may be prepared by reacting 3,5-dinitro-4-chloro-o-toluic acid with phosphorus pentachloride. The resulting o-toluoyl chloride is then treated with ammonia in cold acetone to yield the corresponding 3,5-dinitro-4-chloro-o-toluamide which is converted to the corresponding nitrile by reaction with phosphorus pentoxide or preferably with $POCl_3$.

The preemergence herbicidal compositions of the present invention are solid or liquid formulations comprising an effective amount of one or more of the 2,6-dinitroaniline compounds of Formula I, or preferably Formula II, and those compounds corresponding to Formula I wherein $R_2$ also represents methyl with a herbicidal adjuvant, i.e., an inert carrier or other conventional formulation aid.

Preparation of the compositions broadly involves admixing an effective amount of the herbicidal agent and adjuvant.

Use of the compositions broadly involves application of an effective amount of the compounds or preferably the compositions to the soil containing seeds of the plants to be controlled.

Typical formulations include, for example, dusts, dust concentrates, wettable powders, granulars, and the like. Application by conventional methods and equipment is usually made at rates of from about ⅛ pound per acre to about 20 pounds per acre and preferably ¼ to 8 pounds per acre of active material.

Dusts are generally prepared by grinding together from about 1% to 15% by weight of the active material with from about 99% to 85% by weight of a solid diluent, such as an attaclay, kaolin, diatomaceous earth, fullers earth, talc, pumice or the like.

Dust concentrates are prepared in similar fashion to the dusts excepting that generally about 15% to about 95% by weight of active material is used.

Granular formulations may be prepared by applying a liquid solution of the active material to sorptive granular carriers, such as attaclay, kaolin, or diatomite granules. Alternatively, they may be mixed with inert carriers and applied to non-sorptive granules, such as sand or limestone.

Wettable powders are prepared by grinding the active ingredient with a solid carrier, such as used in the dust formulations. Usually, about 25% to 75% by weight of the active material and from about 73% to 23% by weight of solid carrier is used. In addition, there is generally added about 1% to 5% by weight of a dispersing agent, such as alkali metal salts of napthalene sulfuric acid and anionic-non-ionic blends, and from about 1% to 5% by weight of a surfactant, such as polyoxyethylene alcohols, acids, adducts, sorbitan fatty acid esters and sorbitol esters. Typical formulations by weight percent are given below.

TABLE I

Typical Wettable Powder Formulations

A Ingredients

| | |
|---|---|
| 25% | N-(1-Ethylpropyl)-3-(methoxymethyl)-2,6-dinitro-p-toluidine |
| 65% | attaclay |
| 5% | sodium lignosulfonate |
| 5% | sodium N-methyl-N-oleoyl taurate |

B Ingredients

| | |
|---|---|
| 33% | 4-Ethyl-N-(1-ethylpropyl)-α-methoxy-2,6-dinitro-m-toluidine |
| 59% | attaclay |
| 5% | sodium lignosulfonate |
| 3% | alkyl phenoxy polyoxyethylene ethanol |

C Ingredients

| | |
|---|---|
| 40% | N-(1-ethylpropyl)-7-methoxy-4,6-dinitro-o-cymen-5-amine |
| 50% | precipitated hydrated silicon dioxide (Hi Sil)[a] |
| 5% | sodium lignosulfonate |
| 3% | anionic-nonionic blend (MAL-77L)[b] |
| 2% | wetting agent |

[a] By Pittsburgh Plate Glass Company
[b] By Wm. Cooper and Nephews

The wettable powder formulations are usually dispersed in water and applied as a liquid spray to the area or locus where control of undesirable plant species is desired.

For use as preemergence herbicides, the dusts or liquid sprays containing the active compound can be applied to the soil shortly after planting or they may be incorporated into the soil by the technique referred to as preplant incorporation.

The practice and advantages of the present invention and preparation of the active ingredients used therein is further illustrated by the following examples which are not to be taken as being limitative thereof. Parts and percentages herein are by weight unless otherwise indicated.

EXAMPLE 1

Preparation of 3,4-Dimethyl-2,6-Dinitrochlorobenzene

Two grams of 3,4-dimethyl-2,6-dinitroaniline [*Chemical Abstracts* 44: 4447 (1950)] is dissolved in 40 ml. of warm glacial acetic acid. The solution is cooled to room temperature and a mixture of 0.9 grams of sodium nitrite in 7 ml. of concentrated sulfuric acid is added very slowly leaving a solid in the mixture. This mixture is then added to a solution of cuprous chloride in concentrated hydrochloric acid. The cuprous chloride solution is prepared by dissolving 3.24 grams of $CuSO_4.5H_2O$ in water and adding NaCl to the warm solution. While holding the blue solution in an ice bath, a solution of 1.24 grams of sodium meta-bisulfite and 0.52 grams of NaOH in 12 ml. of water is added. A white precipitate forms and is dissolved in 12 ml. of concentrated hydrochloric acid. The diazonium mixture is then warmed, filtered, and the solid collected and recrystallized from cyclohexane. The product has a melting point of 109° C. to 111° C. The procedures are repeated using 16 grams of the amine, yielding 11 grams of product, having a melting point of 111° C. to 113° C.

EXAMPLE 2

Preparation of 3,4-Dimethyl-2,6-Dinitrochlorobenzene

Fuming sulfuric acid (750 ml., 23%) and fuming nitric acid (240 ml., 90%) are mixed at 0° C. to 45° C. Then 4-chloro-o-xylene (270 grams, 1.93 moles) is added at 10° C. to 60° C. When the addition is complete, the reaction mixture is poured into 8000 ml. of ice and 4000 ml. water and then filtered. The cake is washed with 4000 ml. of water, 500 ml. methanol, and finally 500 ml. of petroleum ether. The cake is then slurried two times with 200 ml. xylene and filtered. The filter cake is then washed with 50 ml. cold xylene and 300 ml. of methanol at 50° C. The solid is then recrystallized from 2500 ml. of methanol and washed with 2 pints of petroleum ether. The yield of white solid is 120 grams with melting point 112° C. to 113° C.

EXAMPLE 3

Preparation of 3,4-Dimethyl-2,6-dinitro-N,N-di-n-propylaniline

Five grams of 1-chloro-3,4-dimethyl-2,6-dinitrobenzene and 5.05 grams of di-n-propylamine are dissolved in benzene and the mixture is refluxed. The benzene is then removed from the mixture by boiling and toluene is added to the remaining residue. The thus-formed mixture is then refluxed, filtered, and the filtrate stripped in vacuo. The residue is treated with hexane and the mixture chilled in dry ice and acetone. The solid from the mixture is collected and dried, it has a melting point of 42° C. to 43.5° C. and is the desired product.

EXAMPLE 4

Preparation of N-Isopropyl-3,4-Dimethyl-2,6-Dinitroaniline

4-Chloro-3,5-dinitro-o-xylene (10.0 grams, 0.043 mole) and i-propylamine (10.1 grams, 0.17 mole) are mixed and refluxed for 12 hours using an efficient reflux condenser. The mixture is then cooled and poured into 100 ml. of 5% hydrochloric acid and extracted with diethyl ether. The ether extract is dried over magnesium sulfate. Removal of the drying agent and solvent leaves an orange oil which readily solidifies. The product is recrystallized from methanol to give 8.7 grams (80%) of an orange solid with melting point 69° C. to 70° C.

EXAMPLE 5

Preparation of N-sec-Butyl-3,4-dimethyl-2,6-dinitroaniline

A mixture of 4-chloro-3,5-dinitro-o-xylene (140 grams, 0.61 mole), mono-sec-butylamine (184 ml., 1.82 moles), and xylene (1400 ml.) is brought to reflux. After refluxing overnight, the reaction mixture is cooled and filtered. The precipitate is washed with petroleum ether. The filtrate and washings are combined, washed with 500 ml. of 10% hydrochloric acid, and finally with 2 liters of water. The organic layer is separated and dried. Removal of the drying agent and the solvent leaves an orange oil which crystallizes with the addition of petroleum ether. A yellow orange solid (150.6 grams, 86.5%) with melting point 42° C. to 43° C. is collected.

Following the above procedure, but substituting 1-chloro-3-methoxymethyl-4-methyl-2,6-dinitrobenzene for 4-chloro-3,5-dinitro-o-xylene and ethylpropylamine for monosec-butylamine, yields (1-ethylpropyl)-3-(methoxymethyl)-4-methyl-2,6-dinitroaniline. Similarly, substituting 1-chloro-3-[(dimethylamino)methyl]-4-methyl-2,6-dinitrobenzene for 4-chloro-3,5-dinitro-o-xylene and ethylpropylamine for mono-sec-butylamine yields (1-ethylpropyl)-3-[(dimethylamino)methyl]-4-methyl-2,6-dinitroaniline.

EXAMPLES 6 TO 50

Following the general procedures of Examples 4 and 5, substituting the appropriate amine for the amines used therein, yields products having the following formula and properties set forth in Table II below.

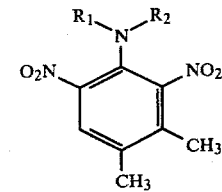

VI

TABLE II

| Example Number | Substituents $R_1$ | $R_2$ | Melting Point °C. | Crystallizing Solvent |
|---|---|---|---|---|
| 6 | H | H | 141–142 | ethanol |
| 7 | H | $C_3H_7$ | 71–71.5 | cyclohexane |
| 8 | $C_4H_9$ | $C_2H_5$ | oil | |
| 9 | $CH_2CH=CH_2$ | $CH_2CH=CH_2$ | 41–42 | hexane/petroleum ether |
| 10 | $CH_3$ | $CH_3$ | 84–85 | methanol |
| 11 | | ⟨O—⟩ (morpholino) | 118–119 | methanol |
| 12 | $C_3H_7$ | $C_3H_7$ | 42–43.5 | hexane |
| 13 | H | $CH_2C(CH_3)_3$ | 88–89 | methanol |
| 14 | H | CHCH$_2$CH$_2$CH(CH$_3$)$_2$ / CH$_3$ | 79–80 | |
| 15 | H | $CH(CH_2CH_2CH_3)_2$ | 48–49 | |
| 16 | H | CHC$_4$H$_9$-t / CH$_3$ | 100–101 | |
| 17 | $C_2H_5$ | $C_2H_5$ | oil | |
| 18 | H | CH—C$_3$H$_7$-n / C$_2$H$_5$ | 40–42 | |
| 19 | H | $C_6H_{13}$-n | oil | |
| 20 | H | $C_4H_9$-n | 68–71 | methanol |
| 21 | H | CHC$_2$H$_5$ / CH$_3$ | 43–44 | hexane |
| 22 | $C_4H_9$-n | $C_4H_9$-n | 30–31 | methanol |
| 23 | H | $CH(CH_3)_2$ | 67–68 | $H_2O$/methanol |
| 24 | H | $CH_2CH(CH_3)_2$ | 46–47 | methanol |
| 25 | H | $CH_2CH=CH_2$ | 81–82 | methanol |
| 26 | H | CHCH$_2$CH(CH$_3$)$_2$ / CH$_3$ | 81–82 | methanol |
| 27 | $C_2H_5$ | $CH_2CH_2CH_3$ | oil | |
| 28 | H | $CH(C_2H_5)_2$ | 56–57 | methanol |
| 29 | H | CHCH$_2$CH$_2$CH$_3$ / CH$_3$ | 42–43 | methanol |
| 30 | H | $CH_2CH_2CH(CH_3)_2$ | 48–50 | methanol |
| 31 | | (cyclohexyl) | 106–108 | cyclohexane |
| 32 | | (cyclopentyl) | 120–122 | cyclohexane |
| 33 | H | CH—CH(CH$_3$)$_2$ / CH$_3$ | 61–63 | methanol |
| 34 | H | $C(CH_3)_3$ | 66–67 | hexane |
| 35 | H | CH$_2$CH—C$_2$H$_5$ / CH$_3$ | 44–45 | |
| 36 | H | CH—C≡H / CH$_3$ | | |

TABLE II-continued

| | | | | |
|---|---|---|---|---|
| 37 | H | CH2C(CH3)3 | 88–89 | methanol |
| 38 | H | CH(CH3)C(CH3)3 | 100–101 | methanol |
| 39 | H | CH(CH2)2CH(CH3)2<br>\|<br>CH3 | 79–80 | methanol |
| 40 | H | CH(C3H7-n)2 | 48–49 | methanol |
| 41 | CH3 | –⟨cyclohexyl⟩ | 57–60 | petroleum ether |
| 42 | H | CHC4H9-n<br>\|<br>CH3 | 51–53 | |
| 43 | H | CHCH2OCH3<br>\|<br>CH3 | oil | |
| 44 | CH3 | CH2CH2Cl | oil | |
| 45 | H | CH2CH(OCH3)2 | 72–73 | |
| 46 | H | CH(C2H5)CH2OCH3 | 46–47.5 | |
| 47 | H | CH(CH3)CH2Cl | oil | |
| 48 | H | CH(C2H5)CH2Cl | oil | |
| 49 | H | CH(C2H5)CH2OC2H5 | 47–49 | |
| 50 | H | CH2CH2CH2OCH3 | 43–44 | |

EXAMPLE 51

Preparation of N-(3-Hexyl)-4-allyl-3-methyl-2,6-dinitroaniline

One equivalent of 4-allyl-3-methyl-2,6-dinitrochlorobenzene is dissolved in three volumes of xylene containing two equivalents of 3-hexylamine. The mixture is refluxed for 5 hours and then poured into water. The organic phase is washed with 5% hydrochloric acid and then water, dried over calcium sulfate, and removed in vacuo to leave the above-named product.

EXAMPLE 52

Preparation of 4-Chloro-N-isopropyl-3-methyl-2,6-dinitroaniline

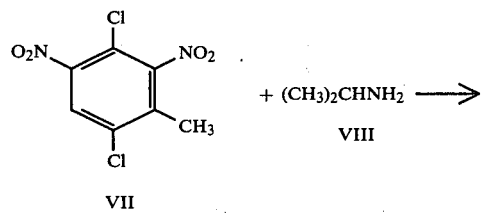

VII

+ (CH3)2CHNH2 ⟶

VIII

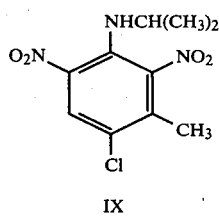

IX

To a stirred mixture of 10.0 grams (0.04 mole) of 3,6-dichloro-2,4-dinitrotoluene in 50 ml. of ethanol is added 9.0 grams (0.15 mole) of isopropylamine. The mixture is stirred at room temperature for 2 hours and then at reflux for one hour. The solution is allowed to cool to room temperature and the crystalline precipitate is filtered and washed with a little hexane to give 10.2 grams of golden crystals, melting point 69° C. to 73° C. Two recrystallizations from methanol give the analytically pure compound, melting point 69° C. to 70° C.

EXAMPLE 53

Preparation of 4-Chloro-3-methyl-2,6-dinitro-N,N-dipropylaniline

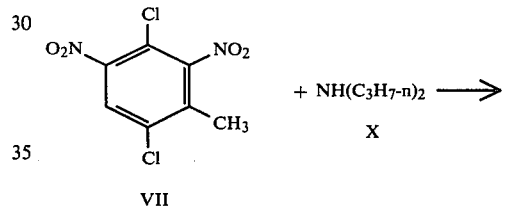

VII

+ NH(C3H7-n)2 ⟶

X

XI

A solution of 10.04 grams (0.04 mole) of 3,6-dichloro-2,4-dinitrotoluene, 12.2 grams (0.12 mole) of di-n-propylamine, and 60 ml. of toluene is stirred at reflux for 9 hours. The mixture is cooled, diluted with ether, and extracted twice with dilute hydrochloric acid. The organic phase is then extracted consecutively with water, aqueous sodium bicarbonate, and brine and dried over magnesium sulfate. Evaporation of the solvent at reduced pressure gives 12.5 grams of an oil. Crystallization of the product from hexane gives 9.08 grams of yellow solid, melting point 36° C. to 38° C. The analytically pure compound, melting point 41° C. to 42° C., is obtained by recrystallization from 95% ethanol.

EXAMPLES 54 TO 74

Following the general procedure of Example 53 substituting the appropriate amine for the di-n-propylamine used therein, yields compounds of the following structural formula having properties set forth in Table III below:

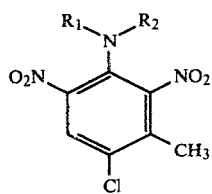

XIII

TABLE III

| Example Number | Substituents R₁ | R₂ | Melting Point °C. |
|---|---|---|---|
| 54 | H | H | 123–125 |
| 55 | H | CH₂CH₂CH₃ | 83.5–85 |
| 56 | H | CH₂CH=CH₂ | 61–62.5 |
| 57 | H | CH(CH₃)₂ | 69–70 |
| 58 | H | CH₂CH(CH₃)₂ | 52–55 |
| 59 | H | CH₃<br>\|<br>CHCH₂CH₃ | oil |
| 60 | H | C(CH₃)₃ | 41–46 |
| 61 | H | CH(CH₂CH₃)₂ | 41.5–44 |
| 62 | H | CH₃<br>\|<br>CHCH₂CH₂CH₃ | 31–32 |
| 63 | H | (CH₂)₅CH₃ | 32.5–34 |
| 64 | H | CH₃<br>\|<br>CHCH₂CH(CH₃)₂ | 62.5–65.5 |
| 65 | H | CH₂CH₂CH₂OCH₃ | 42.5–46.5 |
| 66 | H | CH₂CH₂CN | 101–104 |
| 67 | cyclohexyl | | 84–87 |
| 68 | H | phenyl | 93–94 |
| 69 | CH₃ | CH₃ | 67.5–70 |
| 70 | C₂H₅ | C₂H₅ | oil |
| 71 | CH₂CH=CH₂ | CH₂CH=CH₂ | oil |
| 72 | CH₂CH₂CH₃ | CH₂CH₂CH₃ | 41–43 |
| 73 | morpholino | | 117–120.5 |
| 74 | H | CH₂CH₂CH₂OCH₃ | 43–47 |

EXAMPLE 75

Preparation of Potassium 4-Chloro-3,5-dinitro-o-toluene sulfonate m-Chlorotoluene (166 grams, 1.31 moles) is added to a mixture of 1000 ml. of concentrated sulfuric acid and 170 ml. of 23% fuming sulfuric acid and heated to 100° C. The solution is then cooled to 25° C. and potassium nitrate (400 grams) carefully added at 35° C. to 45° C. After the addition is complete, the reaction is stirred for one hour at 40° C. to 45° C. and then slowly heated to 100° C. and held between 100° C. and 110° C. for 1.5 hours. Finally, the reaction mixture is cooled and poured into 12,000 ml. of ice and the precipitated solid collected. The product is washed with water and then recrystallized from 5 liters of water. The crude yield of potassium salt is 305 grams.

EXAMPLE 76

Preparation of 4-Chloro-3,5-dinitro-o-toluenesulfonyl Chloride

Sixty grams of potassium 4-chloro-3,5-dinitro-o-toluenesulfonate, 70 grams of phosphorus pentachloride and 120 ml of phosphorus oxychloride are mixed and refluxed for 3 hours. The mixture is filtered to remove some insoluble solid. The filtrate is carefully poured into water at 20° C. to 30° C. The precipitated solid is collected and dissolved in 500 ml. of benzene. The benzene solution is washed with water and then dried over MgSO₄. After removing the magnesium sulfate, the benzene is concentrated to 100 ml. and 400 ml. of hexane added. The precipitated solid is collected and recrystallized from 300 ml. hexane and 100 ml. of benzene to yield 50 grams of solid with melting point 105° C. to 107° C.

EXAMPLE 77

Preparation of 4-Chloro-3,5-dinitro-o-toluenesulfonamide

4-Chloro-3,5-dinitro-o-toluenesulfonyl chloride (10 grams, 0.0318 mole) is dissolved in 150 ml. of acetone and chilled to −15° C. Ammonia (1.08 grams, 0.064 mole) is condensed and then vaporized into the acetone solution. When the addition is complete, the reaction mixture is poured into an equal volume of water and the precipitated solid collected. The crude yield of white solid is 6.8 grams with melting point 205° C. to 215° C.

EXAMPLE 78

Preparation of 3-Methyl-2,6-dinitro-N¹,N¹-dipropylsulanilamide

A mixture of 3.4 grams of 4-chloro-3,5-dinitro-o-toluenesulfonamide, N,N-dipropylamine (3.4 grams) and 50 ml. of toluene are brought to reflux. At this point, everything is in solution. After refluxing 24 hours, the mixture is cooled, washed with water, dilute acid and finally water. The organic layer is then separated and dried over MgSO₄. Removal of the drying agent and solvent yields the desired product.

EXAMPLES 79 TO 87

Following the general procedure of Example 78, substituting the appropriate amine and dinitrosulfonamide for N,N-dipropylamine and 4-chloro-3,5-dinitro-o-toluenesulfonamide, respectively, yields the products having the following structure and properties set forth in Table IV below:

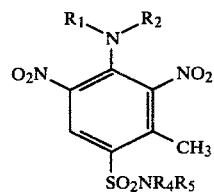

XIV

TABLE IV

| Example Number | Substituents R₁ | R₂ | R₄ | R₅ | Melting Point C. |
|---|---|---|---|---|---|
| 79 | H | C₄H₉-sec | H | H | 126–129.5 |
| 80 | H | C₃H₇-n | H | H | 108–109 |

TABLE IV-continued

| Example Number | Substituents | | | | Melting Point °C. |
|---|---|---|---|---|---|
| | R1 | R2 | R4 | R5 | |
| 81 | H | H | H | H | 226–228 |
| 82 | C3H7-n | C3H7-n | H | CH3 | 140–142 |
| 83 | C3H7-n | C3H7-n | CH3 | CH3 | 124–127 |
| 84 | C3H7-n | C3H7-n | H | —CH—C2H5<br>\|<br>CH3 | 132–134 |
| 85 | CH3 | H | H | CH3 | 206–208 |
| 86 | H | C4H7-sec | H | CH3 | 118–119 |
| 87 | H | C4H7-sec | H | C4H9-sec | 112–114 |

EXAMPLE 88

Preparation of N-sec-Butyl-3-methyl-2,6-dinitro-4-(trifluoromethyl)aniline

A nitration mixture, consisting of 16.1 ml. of H2SO4 (d 1.84) and 1.9 ml. of HNO3 (d 1.5), is heated to 55° C. and 3.5 grams of 5-chloro-2-(trifluoromethyl)toluene is slowly added. The mixture is heated for one hour at 55° C. followed by one hour at 110° C. The reaction mixture is cooled and poured onto ice to give 5-chloro-2-(trifluoromethyl)-4,5-dinitrotoluene as a cream-colored solid. The product is crystallized from cyclohexane to give 3.6 grams of cream-colored crystals, melting point 81° C. to 82° C. 1.8 Grams of 5-chloro-2-(trifluoromethyl)-4,6-dinitrotoluene is refluxed for 15 minutes with 3 ml. of mono-sec-butylamine and 30 ml. of benzene, cooled, filtered, washed with water until neutral, dried, and vacuum stripped to give 1.5 grams of N-sec-butyl-3-methyl-2,6-dinitro-4-(trifluoromethyl)aniline as a yellow solid, melting point 38° C. to 39° C.

EXAMPLES 89 TO 93

Following the general procedure of Example 88, substituting the amine for the mono-sec-butylamine used therein, yeilds compounds having the following structural formula and the properties set forth in Table V below:

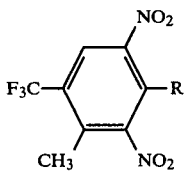

XV

TABLE V

| Example Number | Substituent R | Melting Point °C. |
|---|---|---|
| 89 | —N(C3H7)2 | 32–35 |
| 90 | —NHCH(CH3)2 | Yellow crystals 75–76 |
| 91 | —N(CH3)2 | Yellow crystals 107–108 |
| 92 | —N(C2H5)2 | Orange brown oil |
| 93 | —NHCH(C2H5)2 | 44–45 |

EXAMPLE 94

Preparation of 3,5-Dinitro-4-chloro-o-toluoyl Chloride

Ten grams of 3,5-dinitro-4-chloro-o-toluic acid is warmed on a water bath with 9.2 grams of phosphorus pentachloride and 30 ml. of benzene. After the solids dissolve, the benzene is distilled and the phosphorus oxychloride is removed under reduced pressure. The desired product as a residual oil solidifies on chilling.

EXAMPLE 95

Preparation of 3,5-Dinitro-4-chloro-o-toluamide 3,5-Dinitro-4-chloro-o-toluoyl chloride is treated with two equivalents of ammonia in cold acetone. The mixture is poured into water and the desired product as a precipitated solid collected by filtration.

EXAMPLE 96

Preparation of 3,5-Dinitro-4-chloro-o-toluonitrile

A finely powdered mixture of 15.5 grams (0.051 mole) of 3,5-dinitro-4-chloro-o-toluamide is heated with 12 grams (0.084 mole) of phosphorus pentoxide for 15 minutes at 300° C. to 350° C. The resulting nitrile is distilled from the reaction flask. Recrystallization of the solidified product from methanol gives the desired product as an analytically pure material.

EXAMPLES 97 TO 98

Preparation of 4-Cyano-3-methyl-2,6-dinitro-N,N-dipropylaniline

A mixture of 4.82 grams of 3,5-dinitro-4-chloro-o-toluonitrile and 3 grams of di-n-propylamine in 25 ml. of toluene is refluxed 8 hours. The cooled mixture is then washed with water, dilute acid, and finally water. The organic layer is separated and dried over MgSO4. Removal of the drying agent by filtration and concentration of the filtrate in vacuo leaves a residual oil which when crystallized gives the product with melting point 97° C. to 99° C.

N-sec-butyl-4-cyano-3-methyl-2,6-dinitroaniline is prepared by the above procedure substituting sec-butylamine for the di-n-propylamine. The desired product possessed a melting point of 102° C. to 103° C.

EXAMPLE 99

Preparation of (—)-N-sec-Butyl-2,6-dinitro-3,4-xylidine (—)-sec-Butylamine [prepared according to L. Verbit and P. J. Heffron, Journal of Organic Chemistry 32, 3199 (1967)] was reacted with 4-chloro-3,5-dinitro-o-xylene as by the general procedure of Example 5 to give a yellow-orange solid with melting point 37° C. to 38.5° C., $[\alpha]_D^{25°} = -51.38°$ (c 2.071, ethanol). Concentrations, abbreviated c herein, are measured in grams per 100 ml. of solution.

EXAMPLE 100

Preparation of (—)-N-[1-(Methoxymethyl)propyl]-2,6-dinitro-3,4-xylidine (—)-2-Amino-1-butanol [100 grams, prepared according to D. Pitre and E. B. Grabitz, Chimia 23, 399 (1969)] was added in a dropwise manner to a stirred solution of tert-butanol (800 ml.) containing potassium tert-butoxide (126 grams). After warming this mixture to 70° C. to 80° C. for 2 hours, methyl iodide (175 grams) was added slowly at temperatures below 50° C. The suspension which formed was then stirred with refluxing overnight. After removal of the solid phase by filtration, the filtrate was fractionally distilled to give (—)-1-(methoxymethyl)propylamine contaminated with traces of tert-butanol, boiling point 125° C. to 147° C./760 mm. This amine was then allowed to react with 4-chloro-3,5-dinitro-o-xylene, as described earlier, to give the desired product as a bright yellow solid with melting point 42.5° to 44° C., $[\alpha]_D^{25°} = 137.6°$ (c 2.504, chloroform).

EXAMPLES 101 to 106

The following optical isomers were also prepared using the appropriate optically active amine and following essentially the procedure of Example 100 above:

TABLE V

| Example Number | Compound Name | Melting Point °C. | $[\alpha]_D^{25°}$ |
|---|---|---|---|
| 101 | (+)-N-sec-butyl-2,6-dinitro-3,4-xylidine | 38–38.5 | +50.18 (c 2.217, ethanol) |
| 102 | (+)-N-[1-(methoxymethyl)-propyl]-2,6-dinitro-3,4-xylidine | 43–44 | +132.2 (c 2.504, chloroform) |
| 103 | (−)-N(1-methylbutyl)-2,6-dinitro-3,4-xylidine | 59–61 | −58.0 (c 2.449, ethanol) |
| 104 | (−)-N-sec-butyl-4-chloro-2,6-dinitro-m-toluidine | oil | −42.3 (c 2.550, ethanol) |
| 105 | (−)-4-chloro-N-[1-methoxymethyl)-propyl]-2,6-dinitro-m-toluidine | 40–42 | −107 (c 2.466, CHCl$_3$) |
| 106 | (−)-4-chloro-N-(1-methylbutyl)-2,6-dinitro-m-toluidine | oil | −57.2 (c 3.263, ethanol) |

EXAMPLE 107

Preparation of Methyl 2-methyl-5-nitrobenzyl ether

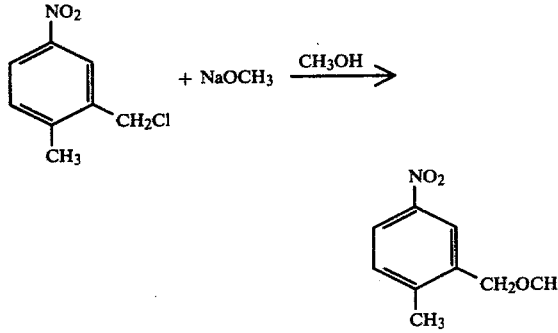

2-Methyl-5-nitrobenzyl chloride (16.2 g) was dissolved in methanol (180 ml) and then sodium methoxide (5.4 g) was added and the mixture refluxed. The reaction was followed by tlc (75/25 v/v, hexane/benzene) and additional quantities of sodium methoxide added and heating continued until the reaction was complete. Finally, the mixture was cooled and filtered. The filtrate was concentrated in vacuo and the residue taken up in methylene chloride, washed with water, then the organic layer was separated and dried over magnesium sulfate. Removal of the drying agent by filtration and concentration of the filtrate in vacuo left 15.8 g, which was recrystallized from 150 ml of hexane to give 11.5 g of white solid with m.p. 45°–49° C. Another run gave a solid which after recrystallization from hexane gave a solid with m.p. 50°–52° C.

Calculated for C$_9$H$_{11}$NO$_3$: C, 59.66; H, 6.12; N, 7.73.
Found: C, 59.65; H, 6.17; N, 7.64.

EXAMPLE 108

Preparation of 3-(Methoxymethyl)-p-toluidine

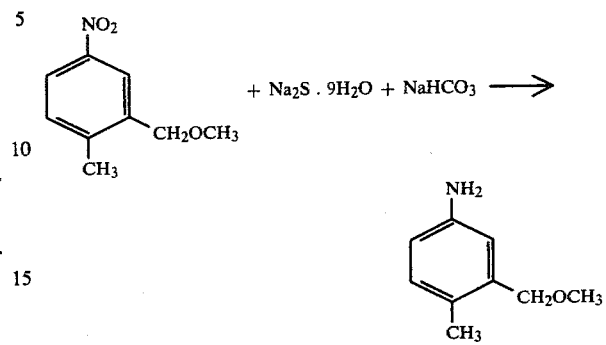

Methyl 2-methyl-5-nitrobenzyl ether (11.5 g) was dissolved in 125 ml of absolute ethanol. To this was added a solution of sodium sulfide monohydrate (48.3 g) and sodium bicarbonate (16.7 g) in 75 ml of water. The resulting mixture was refluxed until tlc indicated all the starting material was gone. The mixture was then concentrated in vacuo to an oily solid. Methylene chloride was added and the mixture filtered. The methylene chloride layer was separated and dried. After removal of the drying agent, the solvent was concentrated in vacuo to give 9.3 g of a mobile orange liquid.

EXAMPLE 109

Preparation of N-(1-Ethylpropyl)-3-(methoxymethyl)-p-toluidine; also named (1-ethylpropyl)-3-(methoxymethyl)-4-methyl-2,6-dinitroaniline

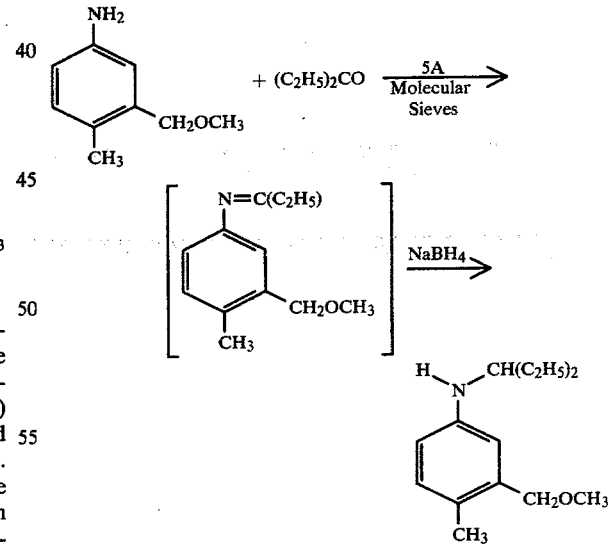

A slurry of 3-(methoxymethyl)-p-toluidine (9.3 g) in 40 ml of diethyl ketone and 5A molecular sieves (19 g) was stirred at room temperature for 15 hours. The mixture was then filtered and the filtrate treated with more diethyl ketone (10–15 ml) and fresh molecular sieves (10 g). After 40 minutes at 40°–50° C., the mixture was filtered and concentrated in vacuo. The crude product (9.0 g) was dissolved in 50 ml of methanol and cooled to 10° C. Then sodium borohydride (3.7 g) was added in small portions. During the addition more methanol (25 ml) was added. Thirty minutes after the addition was complete, the mixture was made acidic with 10% hydrochloric acid and ice. The mixture was extracted with ether and the ether extract discarded. The aqueous extract was then made basic and extracted with ether. After drying the ether extract over magnesium sulfate, the drying agent was removed and the ether concentrated to an orange oil (8.1 g) which by glc was >97% one component. Fractional distillation gave a sample with 120°–125° C./0.4–0.5 mm.

Calculated for $C_{14}H_{23}NO$: C, 75.97; H, 10.47; N, 6.33. Found: C, 75.87; H, 10.62; N, 6.24.

EXAMPLE 110

Preparation of N-(1-Ethylpropyl)-3-(methoxymethyl)-2,6-dinitro-p-toluidine; also named (1-ethylpropyl)-3-(methoxymethyl)-4-methyl-2,6-dinitroaniline.

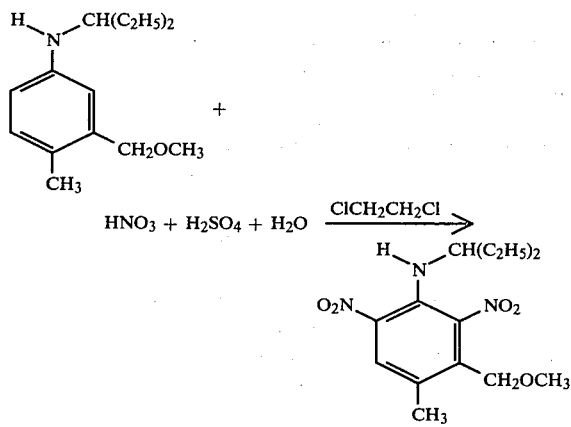

A solution of N-(1-ethylpropyl)-3-(methoxymethyl)-p-toluidine in 10 ml of dichloroethane was prepared and treated with a nitrating mixture consisting of 3.78 g of nitric acid, 3.0 g of concentrated sulfuric acid, and 1.4 g of water. The addition was carried out at 30° C.±3° C. and then held there for 3 hours. The crude product was poured into water and extracted with methylene chloride. The methylene chloride layer was separated and dried over magnesium sulfate. Removal of the drying agent by filtration and concentration of the filtrate in vacuo left a residue of 3.2 g. The crude product was purified by column chromatography on silca gel with benzene as the eluting agent. All fractions consisting of the same compound by tlc were combined to give 1.3 g of orange solid with m.p. 55°–57° C. A sample recrystallized for analysis from hexane had m.p. 56°–57° C.

Calculated: $C_{14}H_{21}N_3O_5$: C, 54.01; H, 6.80; N, 13.50. Found: C, 54.00; H, 6.69; N, 13.44.

EXAMPLE 111

Preparation of 4-Ethyl-N-(1-ethylpropyl)-α-methoxy-2,6-dinitro-m-toluidine

A solution of 13.0 g. of concentrated nitric acid, 10.75 g. of concentrated sulfuric acid, and 4.88 grams of water was added dropwise over a 2.3 hour period to a stirred solution of 7.75 g. of 4-ethyl-N-(1-ethylpropyl)-α-methoxy-m-toluidine in 35 ml. of 1,2-dichloroethane. The temperature of the mixture was maintained between 18° C. and 21° C. during the addition and for an additional 44 hours. The mixture was poured onto 30 g. of ice and then extracted with methylene chloride. The extracts were combined with the dichloroethane layer, the combined organic layers washed with 2.5% aqueous sodium hydroxide and water and stirred over magnesium sulfate. The filtered solution was concentrated under vacuum to yield 10.86 g. of a dark brown solid. Purification by chromatography yielded yellow-orange crystals with m.p. 28° C. to 29° C.

EXAMPLE 112

Preparation of 4-Ethyl-α-methoxy-2,6-dinitro-m-toluidine

The amine (100 g.) was slowly added to 2 l. of 50% sulfuric acid with stirring and then warmed to 70° C. for 22 hours. The reaction mixture was diluted with ice water, extracted with benzene and the benzene layer concentrated to an oily residue. The residue was taken up in $CCl_4$ (100 ml.) and poured with stirring into hexane (1.2 l.). The resulting solid after drying weighed 74 g. (94% yield) and had m.p. 71°–73°.

EXAMPLE 113

Preparation of 3-Chloro-6-ethyl-2,4-dinitrobenzyl methyl ether

A solution of the aniline (40 g. in 750 ml. acetic acid) was added slowly with stirring to a solution of $NaNO_2$ (17 g.) in 136 ml. sulfuric acid at 10°–15° C. After 30 minutes this reaction mixture was added to a solution of CuCl (37.8 g.) in 480 ml. hydrochloric acid with stirring. The product (25.0 g.) precipitated from the cooled reaction mixture in 58% yield with m.p. 81°–82°. The filtrate upon dilution yielded another 10 g. of product.

EXAMPLE 114

Preparation of 4-Ethyl-α-methoxy-N-[1-(methoxymethyl)-propyl]-2,6-dinitro-m-toluidine The benzyl ether (5 g.) and 1-(methoxymethyl)-propylamine (4.1 g.) were dissolved in toluene (100 ml.) and heated to reflux. After 20 hours the reaction mixture was cooled, washed with dilute hydrochloric acid, water and then dried. After passing the solution through a column of neutral alumina, the toluene was removed in vacuo leaving 3.7 g. of an orange oil which upon standing crystallized. Recrystallization from methane gave the pure product, m.p. 54°–55° C.

The following examples can be prepared as shown in Examples 107 to 110 by converting the appropriate 4-alkylnitrobenzene to a methyl 2-alkyl-5-nitrobenzyl ether followed by reductive alkylation with the appropriate ketones and then dinitration or alternatively following the Examples 111 to 114 and Example 3 on page 13.

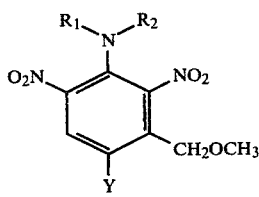

| Ex. No. | R$_1$ | R$_2$ | Y | MP °C. |
|---|---|---|---|---|
| 115 | H | C$_3$H$_7$-n | CH$_3$ | 67.5–69° |
| 116 | H | C$_3$H$_7$-i | " | orange oil |
| 117 | H | C$_4$H$_9$-n | " | 48.5–50° |
| 118 | H | C$_4$H$_9$-sec | " | orange oil |
| 119 | H | C$_4$H$_9$-i | " | 41.5–43.5° |
| 120 | H | CH(CH$_3$)C$_3$H$_7$-n | " | 31.5–32.5 |
| 121 | H | CH(CH$_3$)C$_3$H$_7$-i | " | orange oil |
| 122 | H | CH(CH$_3$)C$_4$H$_9$-n | " | orange oil |
| 123 | H | CH(C$_2$H$_5$)C$_3$H$_7$-n | " | orange oil |
| 124 | H | CH(CH$_3$)CH$_2$C$_3$H$_7$-i | " | 61–62° |
| 125 | H | CH(C$_3$H$_7$-n)$_2$ | " | orange oil |
| 126 | H | CH$_2$C(CH$_3$)=CH$_2$ | " | 43.5–45° |
| 127 | H | CH(CH$_3$)CH$_2$Cl | " | 55–56.5° |
| 128 | H | CH(C$_2$H$_5$)CH$_2$Cl | " | red oil |
| 129 | H | CH(CH$_3$)CHClCH$_3$ | " | 93–97° |
| 130 | C$_3$H$_7$-n | C$_3$H$_7$-n | CH$_3$ | red oil |
| 131 | H | C$_3$H$_7$-n | C$_2$H$_5$ | 45–46° |
| 132 | H | C$_3$H$_7$-i | " | orange oil |
| 133 | H | C$_4$H$_9$-sec | " | yellow-orange oil |
| 134 | H | C$_4$H$_9$-i | " | orange oil |
| 135 | H | CH(CH$_3$)C$_3$H$_7$-n | " | orange oil |

In a manner similar to that shown in Examples 107 to 110, the appropriate 4-alkyl nitrobenzene can be converted to a methyl 2-alkyl-5-nitrobenzyl ether followed by reductive alkylation with the appropriate ketone and then dinitration to give the following examples:

| Ex. No. | R$_1$ | R$_2$ | Y | MP °C. |
|---|---|---|---|---|
| 136 | H | C$_3$H$_7$-n | CH$_3$ | 67.5–69° |
| 137 | H | C$_3$H$_7$-i | " | orange oil |
| 138 | H | C$_4$H$_9$-n | " | 48.5–50° |
| 139 | H | C$_4$H$_9$-sec | " | orange oil |
| 140 | H | C$_4$H$_9$-i | " | 41.5–43.5° |
| 141 | H | CH(CH$_3$)C$_3$H$_7$-n | " | 31.5–32.5 |
| 142 | H | CH(CH$_3$)C$_3$H$_7$-i | " | orange oil |
| 143 | H | CH(CH$_3$)C$_4$H$_9$-n | " | orange oil |
| 144 | H | CH(C$_2$H$_5$)C$_3$H$_7$-n | " | orange oil |
| 145 | H | CH(CH$_3$)CH$_2$C$_3$H$_7$-i | " | 61–62° |
| 146 | H | CH(C$_3$H$_7$-n)$_2$ | " | orange oil |
| 147 | H | CH$_2$C(CH$_3$)=CH$_2$ | " | 43.5–45° |
| 148 | H | CH(CH$_3$)CH$_2$Cl | " | 55–56.5° |
| 149 | H | CH(C$_2$H$_5$)CH$_2$Cl | " | red oil |
| 150 | H | CH(CH$_3$)CHClCH$_3$ | " | 93–97° |
| 151 | C$_2$H$_7$-n | C$_3$H$_7$-n | CH$_3$ | red oil |
| 152 | H | C$_3$H$_7$-n | C$_2$H$_5$ | 45–46° |
| 153 | H | C$_3$H$_7$-i | " | orange oil |
| 154 | H | C$_4$H$_9$-sec | " | yellow-orange oil |
| 155 | H | C$_4$H$_9$-i | " | orange oil |
| 156 | H | CH(CH$_3$)C$_3$H$_7$-n | " | orange oil |
| 157 | H | CH(C$_2$H$_5$)$_2$ | C$_2$H$_5$ | 27.5–29° |
| 158 | H | CH(C$_2$H$_5$)C$_3$H$_6$-n | " | orange oil |
| 159 | H | CH(CH$_3$)CH$_2$C$_3$H$_7$-i | " | orange oil |
| 160 | H | CH(C$_3$H$_7$-n)$_2$ | " | orange oil |
| 161 | H | CH$_2$CH=CH$_2$ | " | 58–60° |
| 162 | H | CH(CH$_3$)CH$_2$Cl | " | 38–40° |
| 163 | H | CH(C$_2$H$_5$)CH$_2$Cl | " | yellow oil |
| 164 | H | CH(CH$_3$)CH$_2$CH$_2$Cl | " | 62–63° |
| 165 | H | C$_3$H$_7$-n | C$_3$H$_7$-i | 45.5–48.5° |
| 166 | H | C$_3$H$_7$-i | " | red-orange oil |
| 167 | H | C$_4$H$_9$-n | " | red oil |
| 168 | H | C$_4$H$_9$-sec | " | red oil |
| 169 | H | C$_4$H$_9$-i | " | red oil |
| 170 | H | CH(CH$_3$)C$_3$H$_7$-n | " | red oil |
| 171 | H | CH(C$_2$H$_5$)$_2$ | " | red-orange oil |
| 172 | H | CH(CH$_3$)C$_4$H$_9$-n | " | red oil |
| 173 | H | CH(C$_2$H$_5$)C$_3$H$_7$-n | " | red oil |
| 174 | H | CH(C$_2$H$_5$)CH$_2$Cl | " | red oil |
| 175 | H | CH(CH$_3$)CHClCH$_3$ | " | red oil |
| 176 | C$_3$H$_7$-n | C$_3$H$_7$-n | C$_3$H$_7$-i | 55–60 |
| 177 | H | C$_3$H$_7$-i | C$_3$H$_7$-n | orange oil |
| 178 | H | C$_4$H$_9$-sec | " | orange oil |
| 179 | H | C$_H$(C$_2$H$_5$)$_2$ | " | 42–43° |
| 180 | H | C$_3$H$_7$-i | C$_4$H$_9$-n | orange oil |
| 181 | H | CH(C$_2$H$_5$)$_2$ | " | orange oil |
| 182 | H | C$_3$H$_7$-i | C$_4$H$_9$-sec | orange oil |
| 183 | H | CH(C$_2$H$_5$)$_2$ | " | red-orange oil |
| 184 | H | CH(C$_2$H$_5$)$_2$ | C$_4$H$_9$-i | orange oil |
| 185 | | C$_4$H$_9$-sec | Cl | 44–47° |
| 186 | | CH(CH$_3$)C$_3$H$_7$-n | " | orange oil |
| 187 | | CH(C$_2$H$_5$)$_2$ | " | 70–72 |
| 188 | C$_2$H$_5$ | C$_2$H$_5$ | " | 38–41° |

EXAMPLE 189

Preparation of N-(1-Ethylpropyl)-3-(1-methoxyethyl)-2,6-dinitro-p-toluidine

Preparation of 2'-methyl-5'-nitro-acetophenone

To 120 ml of concentrated sulfuric acid is added 53.6 g of o-methylacetophenone, while cooling at −10°. To this cold, stirred solution is added a mixture of 32 ml of 70% nitric acid and 48 ml of concentrated sulfuric acid. The reaction solution is stirred for 2½ hours between −9° and 0° and then poured over 800 g of ice. The mixture is extracted with ether and the organic phase washed with water, saturated Na$_2$CO$_3$ solutions, water and finally brine. The ether solution is dried over MgSO$_4$ and evaporated to dryness to give 56.2 g of a pale yellow oil. The oil is crystallized from 95% ethanol to give 25.4 g of product, mp about 50° C. Recrystallization from hexane afforded product mp 53°–55° C.

EXAMPLE 190

Preparation of 1-(2'-Methyl-5'-nitrophenyl)ethanol

To a stirred mixture of 23.5 g of 2'-methyl-5'-nitroacetophenone and 350 ml of ethanol is added NaBH$_4$ in one portion and the solution stirred at room temperature for 1¾ hours. Water and 2 N HCl is added to give pH 5 and the solution concentrated to remove ethanol. The mixture is extracted with ether and the organic phase washed with water and brine. The solution is dried over MgSO$_4$ and evaporated to give 23.12 g of a yellow oil. Hexane (150 ml) is added and the resulting solid collected and washed with hexane affording 22.7 g of crude product, mp 79°–85° C. Recrystallization from chloroform and hexane gives pure product, mp 85°–88° C.

EXAMPLE 191

Preparation of α,2-Dimethyl-5-nitrobenzyl methyl ether 1-(2′-methyl-5′-nitropenyl)ethanol (0.9 g) is dissolved in 5 ml of benzene and 0.8 g of 50% aqueous sodium hydroxide, ca 10 mg of tetrabutylammonium chloride, 5 ml of ether and 1.25 ml of methyl iodide is added. The reaction mixture is stirred at room temperature for 2 hours and heated at 30°–35° for 4 hours. An additional 1.0 ml of methyl iodide is added and the mixture stirred at room temperature for 22 hours. Thin layer chromatography indicates starting material remaining therefore 0.52 ml of 50% NaOH solution and 2.0 ml of methyl iodide are added and the mixture stirred at room temperature for 5 days. Water is added and the mixture extracted with ether. The organic layer is washed with water and brine. The solution is evaporated to dryness giving 0.97 g of oil which is purified by column chromatography to give pure material, mp 35°–37° C.

EXAMPLE 192

Preparation of N-(1-Ethylpropyl)-3-(1-methoxyethyl)-p-toluidine

A mixture of 14.6 g of α,2-dimethyl-5-nitrobenzyl methyl ether, 100 ml of diethyl ketone, 1.0 g of β-naphthalene sulfonic acid and 1.5 g of 5% Pt/C is hydrogenated using a Parr Hydrogenation Apparatus. After 22 hours the reaction mixture is filtered, the filtrate evaporated to dryness and water and ether added. This mixture is basified to pH 11 with 1 N NaOH and the organic phase separated and washed with water and brine. The ether solution after drying over $MgSO_4$ and evaporation to dryness afforded 17.8 g of an orange oil. Purification by column chromatography gave pure product as orange liquid.

EXAMPLE 193

N-(1-Ethylpropyl)-3-(1-methoxyethyl)-2,6-dinitro-p-toluidine

To a stirred solution of 28 g of 70% $H_2SO_4$ and 10.1 ml of 70% $HNO_3$ is added a solution of 9.41 g of N-(1-ethylpropyl)-3-(1-methoxyethyl)-p-toluidine in 30 ml of ethylenedichloride. The solution is accomplished at 25° to 32° over a period of 45 minutes. The reaction mixture is stirred at room temperature for 2¼ hours and warmed at 35°–40° for 2¼ hours. After stirring overnight at room temperature, the organic layer is separated and washed with water and brine. The EDC solution is mixed with 6 g of $NH_2SO_3H$ and 25 ml of concentrated HCl and the mixture is stirred and heated at reflux for 5½ hours. The reaction mixture is diluted with water and the organic layer separated and washed with water, saturated $Na_2CO_3$ solution, water and brine. The EDC solution after drying over $MgSO_4$ and evaporation to dryness gives 9.35 g of crude product as a red oil. Column chromatography afforded 6.27 g of pure product.

EXAMPLE 194

Preparation of N-Isopropyl-4,6-dinitro-o-Cymen-5-amine

Preparation of o-Cymen-5-amine hydrochloride

Hydrogenation of 2-isopropyl-5-nitrobenzylchloride (16.0 gms.) in 95% ethanol (100 ml) with 10% palladium on carbon catalyst (0.5 g) at 18°–36° C. and 35-15 psi of hydrogen afforded 12.9 g (93.5%) of o-cymen-5-amine, hydrochloride after concentration of the filtered reaction solution. Recrystallization of the crude product from a mixture of 2-propanol and ethyl acetate gave the pure compound, mp 212°–222° C. Anal. Calcd. for $C_{10}H_{16}NCl$: C, 64.68; H, 8.69; N, 7.54. Found: C, 64.77; H, 8.64; N, 7.48.

EXAMPLE 195

Preparation of N-(1-Ethylpropyl)-o-Cymen-5-Amine o-Cymen-5-amine (8.8 g., 0.064 mole, prepared by neutralization of cymene-5-amine hydrochloride with aqueous NaOH) is dissolved in 3-pentanone (43 g, 0.5 mole) and 5 A molecular sieve (40 g) is added. The mixture is shaken for 16 hours. Then the used 5 A molecular sieve is removed by filtration and 40 g more 5 A molecular sieve is added. After 24 hours of agitation the mixture is filtered and the filtrate is concentrated to leave an oil (11.4 g). A solution of the oil in absolute ethanol (60 ml.) is added rapidly to a cooled (12° C.), stirred, mixture of sodium borohydride (partially dissolved) in absolute ethanol (100 ml.). Following the addition, the mixture is stirred for 1.5 hours at 25°–27° C. The resulting solution is treated with 6 N HCl (30 ml, to give pH 1) and then with 50% aqueous NaOH to give pH 10. The resulting mixture is filtered to remove inorganic solids, which are washed with ether. The ether washes are combined with the filtrate and the solution is concentrated to leave an oil which is dissolved in ether. The ether solution is washed with saturated aqueous sodium chloride, dried over $MgSO_4$, and concentrated to leave 11.6 g (87.2%) of N-(1-ethylpropyl)-cymen-5-amine, a red liquid. Analysis by glc showed 99.6 area % purity.

EXAMPLE 196

Preparation of N-(1-ethylpropyl)-o-Cymen-5-Amine

A solution of o-cymen-5-amine (33.6 g, 0.24 mole) in 3-pentanone (300 ml.) is mixed with a catalyst consisting of 50% water-wet 5% platinum on carbon (5.9 g.) and 2-naphthalenesulfonic acid (1.1 g.) and subjected to 42.5–18.3 psi of hydrogen at 44° for ca 16 hr. The mixture is cooled and filtered, and the filtrate is concentrated to leave a red liquid which is dissolved in ether. The ether solution is washed with 10% sodium hydroxide solution, dried over magnesium sulfate and concentrated to leave 45.1 g. (88.6%) of N-(1-ethylpropyl)-o-cymen-5-amine of 99.3 area % purity by glc analysis.

EXAMPLE 197

Preparation of N-(1-Ethylpropyl)-4,6-dinitro-o-Cymen-5-amine

A solution of N-(1-ethylpropyl)-o-cymen-5-amine (7.0 g, 0.034 mole) in ethylene dichloride (70 ml.) is cooled in ice during the successive addition of 70% sulfuric acid (16.8 g of 70%, 0.12 mole) and 70% nitric acid (14.0 g of conc. nitric acid, 0.156 mole). The ice bath is then removed and the reaction mixture is stirred at 30°-32° C. for 16 hours. The mixture is then poured on top and the organic layer (diluted with chloroform) is separated, washed with aqueous sodium bicarbonate solution, dried over MgSO4, and concentrated in a rotary evaporator to leave 8.3 g of a red liquid which is twice chromatographed on silica gel dry column once with a 2:1 mixture of hexane and benzene and once with straight hexane, to afford 4.3 g. (41%) of the pure product.

EXAMPLE 198

Preparation of 4,6-Dinitro-o-Cymen-5-Amine

A mixture of 4,6-dinitro-N-(1-ethylpropyl)-o-cymen-5-amine (55 g, 0.18 mole) aqueous sulfuric acid (from conc. sulfuric acid (680 ml.) and water (680 ml.) are stirred and heated at 70°-75° C. for several hrs. The mixture is then diluted with ice and water and extracted with chloroform to give 37.7 g of crude 4,6-dinitro-o-cymen-5-amine, a liquid which crystallized, and which was determined to be 83 area % pure by glc analysis.

EXAMPLE 199

Preparation of 5-Chloro-4,6-Dinitro-o-Cymene

A solution of the amine (3.0 g, 0.012 mole) in acetic acid (60 ml.) is added to a cooled (10°-15° C.), stirred solution of sodium nitrite (1.35 g) in conc. sulfuric acid (10.5 ml). The resulting mixture is stirred for 10 minutes at 10°-15° C. and is then added slowly to a solution of cuprous chloride (1.5 g) in conc. hydrochloric acid (40 ml). The resulting mixture is stirred at 22° C. for 2 hours and the precipitated solid product is then filtered off from the cooled reaction mixture, washed with water, and dried in vacuo.

By the same procedure, 3-chloro-2,4-dinitro-6-propyltoluene, mp 63°-65°, is prepared from 2,6-dinitro-4-propyl-m-toluidine.

EXAMPLE 200

Preparation of N-Isopropyl-4,6-dinitro-o-Cymen-5-amine

A mixture of 5-chloro-4,6-dinitro-o-cymene (4.0 g, 0.0155 mole) and isopropylamine (3.2 g, 0.054 mole) in toluene is heated in a bomb at 100° C. for 4 hours. The cooled mixture is washed with aqueous bicarbonate solution, dried over magnesium sulfate, and concentrated to leave the crude product which is purified by dry column chromatography to yield 3.2 g of product with mp 54°-55° C. By using one of the aforementioned procedures for the dinitration of the appropriate N-alkyl-4-alkyl-m-toluidines or by reacting the appropriate amine with the desired 3-chloro-2,4-dinitro-6-alkyltoluene the following compounds are prepared.

By the same procedure, 3-chloro-2,4-dinitro-6-propyltoluene, mp 63°-65°, is prepared from 2,6-dinitro-4-propyl-m-toluidine.

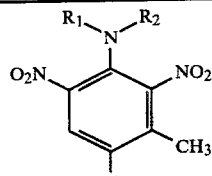

| Ex. No. | R1 | R2 | Y | MP° C. |
|---|---|---|---|---|
| 201 | H | C3H7-i | C2H5 | 46–46.5 |
| 202 | H | C4H9-sec | " | 37.5–38 |
| 203 | H | CH(C2H5)2 | " | 51–53 |
| 204 | H | C3H7-i | C3H7-n | 55 |
| 205 | H | CH(C2H5)2 | " | orange oil |
| 206 | H | C3H7-i | C3H7-i | 54–55 |
| 207 | H | C3H7-n | " | orange-red oil |
| 208 | H | C4H9-sec | " | orange oil |
| 209 | H | CH(C2H5)2 | " | red oil |
| 210 | H | CH(C2H5)2 | C4H9-n | 47.5–50 |
| 211 | H | CH(C2H5)2 | C4H9-sec | orange oil |

EXAMPLE 212

Preparation of 4,6-Dinitro-N,N-Dipropyl-o-Cymen-5-Amine

Preparation of 4'-Isopropyl-2',6'-dinitro-N-propyl-m-propionotoluidide

A solution of 4,6-dinitro-N-propyl-o-cymen-5-amine (2.7 g, 0.0096 mole), propionic anhydride (4.9 g, 0.038 mole) and conc. sulfuric acid (2 drops) is heated at 90° C. for 4 hours. The cooled reaction solution is then diluted with aqueous sodium bicarbonate solution and stirred at 25° C. for 0.5 hour. The resulting mixture is extracted with chloroform. The dried (MgSO4) chloroform solution is concentrated to leave the crude product which is purified by dry column chromatography (silica gel, 1:1 benzenehexane) to give 2.0 g (62%) of 4'-isopropyl-2',6'-dinitro-N-propyl-m-propionotoluidine, mp 78°–80°.

EXAMPLE 213

Preparation of 4,6-Dinitro-N,N-dipropyl-o-Cymen-5-Amine

A solution of 4'-isopropyl-2',6'-dinitro-N-propyl-m-propionotoluidide (1.5 g, 0.005 mole) and borane (9.9 ml. of 1 M solution in tetrahydrofuran) in tetrahydrofuran (10 ml.) is heated at reflux for 4 hours. The solution is then cooled in ice and 3 N aqueous hydrochloric acid (4 ml.) is slowly added with stirring. The resulting mixture is extracted with ether, and the ether extract is washed with aqueous bicarbonate solution, dried over MgSO4, and concentrated to leave 4,6-dinitro-N,N-dipropyl-o-cymen-5-amine, mp. 48.5°–49°, an orange solid.

EXAMPLE 214

Preparation of α-chloro-2-ethyl-5-nitrotoluene

Paraformaldehyde (105.1 g) is added portionwise to a stirred solution of 620 ml. of concentrated sulfuric acid and 720 ml. of fuming sulfuric acid at 3° C. to 10° C. Anhydrous calcium chloride (252.5 g) is then added portionwise maintaining the temperature of the mixture between 4° C. and 11° C. The mixture is stirred in an ice bath for 1.5 hours and then treated dropwise with 260.0 g of 4-ethylnitrobenzene to maintain the reaction temperature between 6° C. and 9° C. The mixture is stirred between 9° C. and 18° C. for 13 hours and then between 18° C. and 20° C. for 123 hours. The mixture is poured into a slurry of ice and water and the crude product is extracted with chloroform. The chloroform layer is partially concentrated, shaken with 100 ml. of potassium bicarbonate, water, and stirred over magnesium sulfate. The filtered solution is concentrated under vacuum to yield 317.6 g. of an amber liquid. The crude product is fractionated by vacuum distillation to yield a light yellow liquid with boiling point 114° C. to 118° C. at 0.2 mm. HG.

EXAMPLE 215

Preparation of 2-ethyl-5-nitrobenzyl methyl ether

Sodium methoxide is added portionwise to a solution of 150.0 g of α-chloro-2-ethyl-5-nitrotoluene in 1.15 l. of methanol maintained between 18° C. and 30° C. The mixture is refluxed for 2 hours, cooled to 3° C., and filtered. The filtrate is concentrated under vacuum and the resulting slurry shaken with saturated aqueous sodium chloride and methylene chloride. The methylene chloride layer is washed, filtered through sodium sulfate, and stirred over magnesium sulfate. The filtered solution is concentrated under vacuum to yield 133.89 g. of a dark brown liquid. The crude product is fractionated by vacuum distillation to yield a yellow liquid with boiling point 113° C. to 115° C. at 0.35 mm Hg which solidifies to light yellow prisms with mp 21.5° C. to 23.5° C.

EXAMPLE 216

Preparation of 4-ethyl-N-(1-ethylpropyl)-α-methoxy-m-toluidine

A mixture of 10 g. of 2-ethyl-5-nitro benzyl methyl ether, 10.38 g. of 3-pentanone, 0.23 g. of 2-naphthalene sulfonic acid, and 0.60 g. of 5% platinum on carbon catalyst is shaken under hydrogen for 2 hours at room temperature and for 4 hours at 48° C. to 60° C. The mixture is diluted with 200 ml of ether, filtered and the filtrate shaken with 2.5% aqueous sodium hydroxide, washed with water, filtered through sodium sulfate and stirred over magnesium sulfate. The filtered solution is concentrated under vacuum to yield 10.76 g of an amber liquid, pure by glc and tlc analyses.

EXAMPLE 217

Preparation of 4-Ethyl-N-(1-ethylpropyl)-α-methoxy-2,6-dinitro-m-toluidine

A solution of 13.0 g of concentrated nitric acid, 10.75 g of concentrated sulfuric acid, and 4.88 g of water is added dropwise over a 2.3 hour period to a stirred solution of 7.75 g of 4-ethyl-N-(1-ethylpropyl)-α-methoxy-m-toluidine in 35 ml. of 1,2-dichloroethane. The temperature of the mixture is maintained between 18° C. and 21° C. during the addition and for an additional 44 hours. The mixture is poured onto 30 g of ice and then extracted with methylene chloride. The extracts are combined with the dichloroethane layer, the combined organic layers washed with 2.5% aqueous sodium hydroxide and water and stirred over magnesium sulfate. The filtered solution is concentrated under vacuum to yield 10.86 g of a dark brown solid. Purification by chromatography yields yellow-orange crystals with mp 28° C. to 29° C.

EXAMPLE 218

Preparation of 4-ethyl-α-methoxy-2,6-dinitro-m-toluidine

The amine (100 g) is slowly added to 2 l. of 50% sulfuric acid with stirring and then warmed to 70° C. for 22 hours. The reaction mixture is diluted with ice water, extracted with benzene and the benzene layer concentrated to an oily residue. The residue is taken up in CCl$_4$(100 ml) and poured with stirring into hexane (1.2 l.). The resulting solid after drying weighs 74 g (94% yield) and has mp 71°–73°.

EXAMPLE 219

Preparation of 3-chloro-6-ethyl-2,4-dinitrobenzyl methyl ether

A solution of the aniline (40 g in 750 ml acetic acid) is added slowly with stirring to a solution of NaNO$_2$ (17 g) in 136 ml. sulfuric acid at 10°–15° C. After 30 minutes this reaction mixture is added to a solution of CuCl (37.8 g) in 480 ml hydrochloric acid with stirring. The product (25.0 g) precipitates from the cooled reaction mixture in 58% yield with mp 81°–82°. The filtrate upon dilution yields another 10 g of product.

EXAMPLE 220

Preparation of 4-(4-Ethyl-α-methoxy-2,6-dinitro-m-tolyl)-2,5-dimethylmorpholine

The benzyl ether (5 g) and 2,6-dimethylmorpholine (6.7 ml) are dissolved in toluene and heated under reflux for 24 hours. The reaction mixture is washed with dilute hydrochloric acid, water and dried. After concentration the solid residue (4.9 g) is purified by chromatography on silica gel to give the product as a yellow solid with mp 84°–86° C.

EXAMPLE 221

Preparation of 1-(4-Ethyl-α-methoxy-2,6-dinitro-m-tolyl)-pyrrolidine

In a similar manner the subject compound is prepared using pyrrolidine in place of 2,6-dimethylmorpholine. The product is isolated as an orange solid with mp 49°–50° C.

EXAMPLES 222 AND 223

Preparation of 4-Cyano-3-methyl-2,6-dinitro-N,N-dipropylaniline

A mixture of 4.82 grams of 3,5-dinitro-4-chloro-o-toluonitrile and 3 grams of di-n-propylamine in 25 ml. of toluene is refluxed 8 hours. The cooled mixture is then washed with water, dilute acid, and finally water. The organic layer is separated and dried over MgSO$_4$. Removal of the drying agent by filtration and concentration of the filtrate in vacuo leaves a residual oil when crystallized gives the product with melting point 97° C. to 99° C.

N-sec-butyl-4-cyano-3-methyl-2,6-dinitroaniline is prepared by the above procedure substituting sec-butylamine for the di-n-propylamine. The desired product possessed a melting point of 102° C. to 103° C.

Examples 224 to 231 illustrate the preparation of the compound 4-cyano-N-(1-ethylpropyl)-α-methoxy-2,6-dinitro-m-toluidine.

EXAMPLE 224

Methyl-4-chloro-α-methoxy-o-toluate

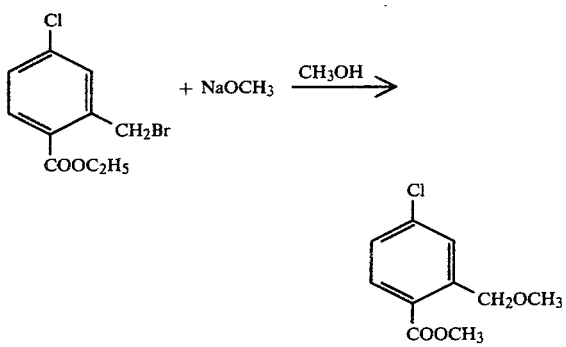

Ethyl α-Bromo-4-chloro-o-toluate (26.4 g.) is added to a solution (10°) of sodium methoxide (5.4 g.) in 110 ml. of methanol. When the addition is complete, the mixture is refluxed for two hours, then cooled and concentrated in vacuo. The oily residue is partioned between ether-water. The ether layer is separated and dried. Removal of the drying agent and concentration of the filtrate in vacuo leaves 17.3 g. of a white solid. A sample of the product recrystallized from methanol had mp 44°–45°.

EXAMPLE 225

Methyl 4-chloro-α-methoxy-5-nitro-o-toluate

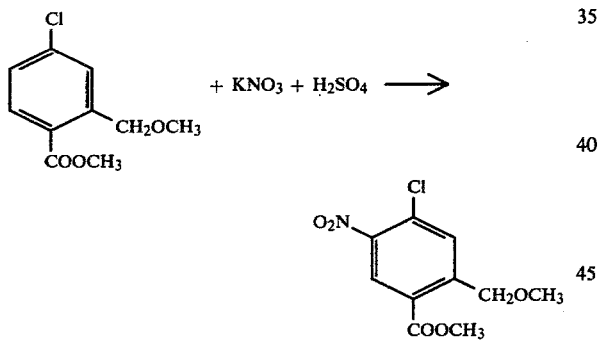

A sample of methyl 4-chloro-α-methoxy-o-toluate (10 g.) is added in small portions at 15°–20° to a solution of potassium nitrate (4.9 g.) in concentrated sulfuric acid. When the addition is complete, the mixture is stirred for 1 hour at 10°–15°, then poured onto ice and the precipitated solid (12.8 g.) collected by filtration. A sample of the damp product is recrystallized from 90% ethanol. After recrystallization, the solid mp is 77°–81°.

EXAMPLE 226

4-Chloro-α-methoxy-5-nitro-o-toluic acid

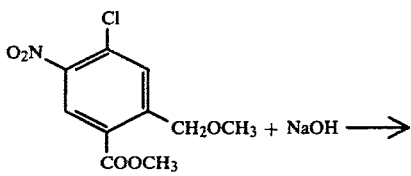

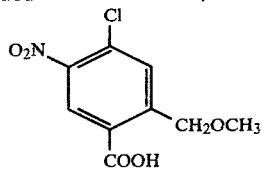

A slurry of methyl 4-chloro-α-methoxy-5-nitro-o-toluate (7.0 g.) in dilute sodium hydroxide (35 ml of 1N) is stirred about 30 hours. The yellow slurry is then diluted with 50 ml. of water resulting in a clear yellow solution. The solution is extracted with ether, then the aqueous layer is separated and acidified to give 5.7 g. of an off-white solid. A sample recrystallized from benzene has a mp 155°–157°.

EXAMPLE 227

4-Chloro-α-methoxy-5-nitro-o-toluoyl chloride

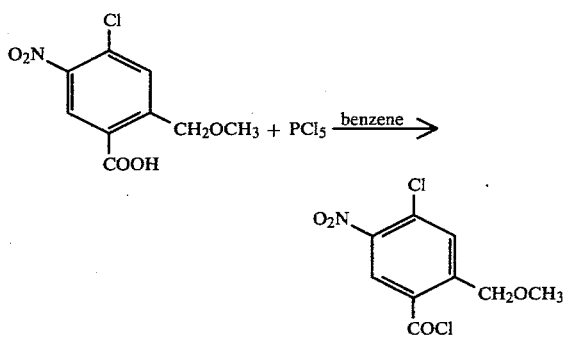

A mixture of 4-chloro-α-methoxy-5-nitro-o-toluic acid (3.6 g.) and phosphorus pentachloride (3.0 g.) in 120 ml of benzene is refluxed for thirty minutes. The mixture is then concentrated in vacuo and the residue boiled with 200 ml of hexane and filtered hot. The filtrate is partially concentrated and chilled to give 2.5 g. of white solid with mp 63°–65°.

EXAMPLE 228

4-Chloro-α-methoxy-5-nitro-o-toluamide

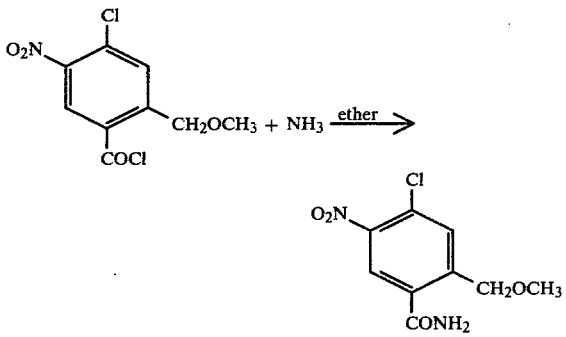

A sample of 4-chloro-α-methoxy-5-nitro-o-toluoyl chloride (1.5 g.) is added to 100 ml of ether saturated with ammonia. During the addition and for 15 minutes thereafter, the reaction temperature is kept below 20°. The precipitate solid is collected and washed well with water. The crude product (0.9) has an infrared compatible with the desired structure.

EXAMPLE 229

4-Chloro-α-methoxy-5-nitro-o-tolunitrile

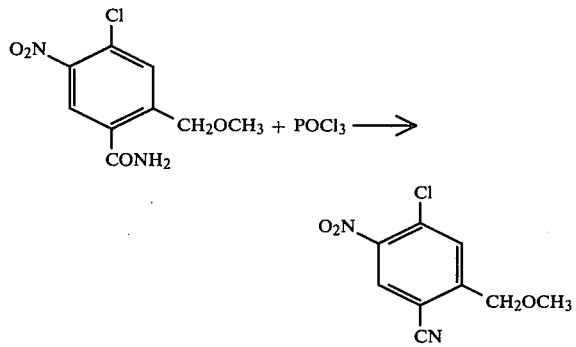

A sample of 4-chloro-α-methoxy-5-nitro-o-toluamide (0.8 g) is added to phosphorus oxychloride (10 ml) and the slurry gradually heated to reflux. After about 10 minutes at reflux, all the solid has dissolved giving a clear yellow solution. The solution is concentrated in vacuo and the crude residue is portioned between ether and water. The ether layer is separated and dried. Removal of the drying agent and concentration of the filtrate in vacuo leaves a crude solid (0.7 g.) with mp 57°–59°.

EXAMPLE 230

4-Cyano-N-(1-ethylpropyl)-α-methoxy-6-nitro-m-toluidine

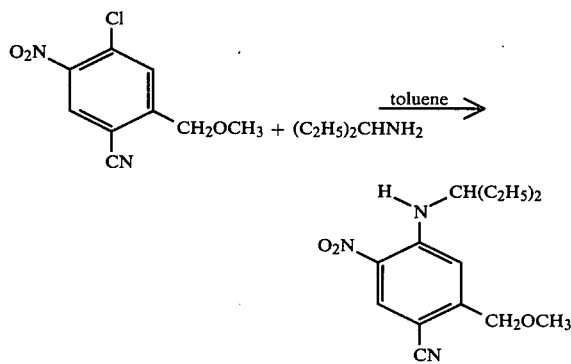

4-Chloro-α-methoxy-5-nitro-o-tolunitrile (0.7 g.) is added to 10 ml. of toluene and the resulting solution refluxed for 1 hour and then stirred overnight at room temperature. Since glc indicated the reaction was incomplete, it was refluxed an additional 30 minutes. The mixture is then cooled, washed with water, dilute hydrochloric acid, and finally saturated sodium chloride solution. The organic layer is separated and dried. Removal of the drying agent and concentration of the filtrate in vacuo leaves an

EXAMPLE 231

4-Cyano-N-(1-ethylpropyl)-α-methoxy-2,6-dinitro-m-toluidine

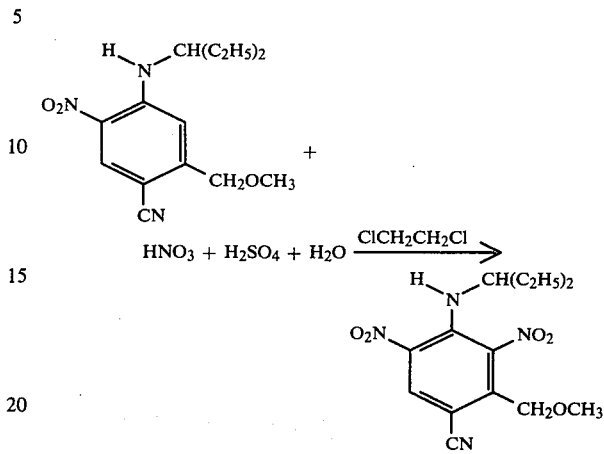

A sample of 4-cyano-N-(1-ethylpropyl)-α-methoxy-6-m-toluidine (0.4 g) in 10 ml. of 1,2-dichloroethane is treated with a nitrating mixture consisting of water (0.15 g), sulfuric acid (0.33 g) and nitric acid (1.7 g) are added and stirring continued at 35° until tlc (benzene-silica gel) indicates no more starting material. After the usual work-up, 0.4 g. of dark oil is chromatographed on 10 g. of silica gel and developed using hexane and hexane-benzene mixtures. The major spot by tlc is isolated as a yellow solid (0.2 g) with mp 46°–49°. The IR and nmr are in agreement for the desired structure.

The remaining compounds of the invention are prepared in a similar manner.

EXAMPLE 232

Preparation of α$^3$-methoxy-N-(2-methoxy-1-methylethyl)-3,4-Xylidine

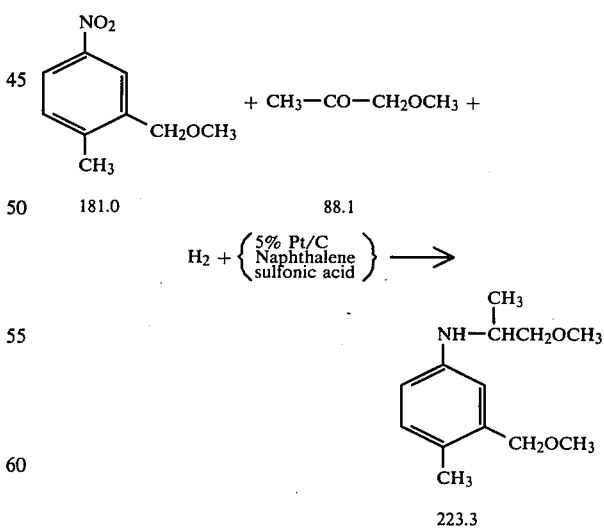

A mixture of methyl 2-methyl-5-nitrobenzyl ether (12 g, 0.066 M), methoxyacetone [20 g (used as solvent)], 2-naphthalenesulfonic acid (0.3 g) and 5% Pt/C (0.7 g) is shaken on a Parr hydrogenator maintaining the temperature below 40° with external cooling. The theoretical amount of hydrogen (0.26 M) is consumed and further uptake ceases after 2 hours.

The reaction mixture is filtered and the excess methoxyacetone removed in vacuo to yield a red oil. This oil is purified on a silica gel column, eluting with benzene, yielding 7.6 g (52%) of a colorless oil. Analysis calculated: C-69.91%; H-9.48%; N-6.26%; Found: C-69.88%; H-9.19%; N-6.36%.

EXAMPLE 233

Preparation of α³-Methoxy-N-(2-Methoxy-1-Methylethyl)-2,6-dinitro-3,4-Xylidine

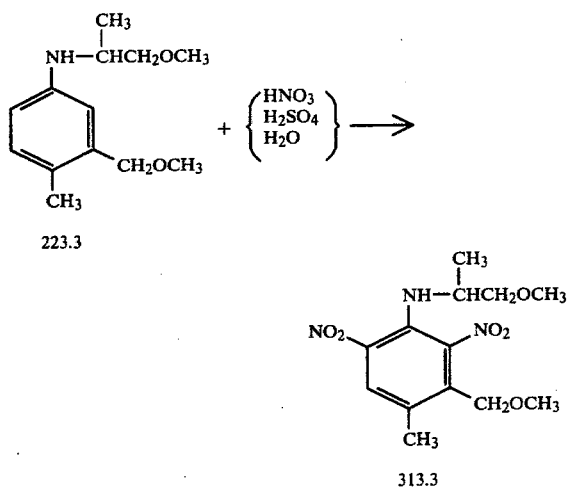

A nitration mixture consisting of conc. sulfuric acid (1.4 g), water (0.7 g) and 70% nitric acid (1.8 g) is added at 25° to a solution of α³-methoxy-N-(2-methoxy-1-methylethyl)-3,4-xylidine (1.0 g, 0.004 M) in 10 ml of dichloroethane. After stirring at 25° for 1 hour, then at 40° for 1 hour, the reaction mixture is cooled and poured onto ice. The desired product is obtained by extraction with chloroform and isolated as an orange oil, which is purified using a silica gel column, eluting with hexane/benzene (90/10). The resulting solid is crystallized from a small amount of methanol yielding 0.8 g. (64%) of light yellow crystals melting at 54.5°–56°. Analysis calculated: C-49.83%; H-6.11%; N-13.41%; Found: C-49.77%; H-5.90%; N-13.24%.

In a similar manner to Examples 20 and 21 the appropriate α3-methoxy-3,4-xylidine or 4-chloro-α-methoxy-m-toluidine is nitrated to give the following compounds:

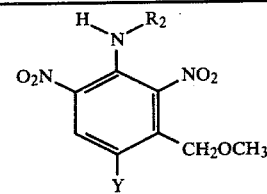

| Ex | $R_2$ | Y | mp° C. |
|---|---|---|---|
| 234 | $CH(CH_3)CH_2OCH_3$ | $C_3H_7i$ | Orange oil |
| 235 | $CH(CH_3)CH_2CH_2OCH_3$ | $C_3H_7i$ | Orange oil |
| 236 | $CH(CH_3)CH_2CH_2OCH_3$ | Cl | Orange oil |
| 237 | $CH(CH_3)CH_2OCH_3$ | Cl | 31–34 |

The selective preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous-acetone solution containing test compound in sufficient quantity to provide the equivalent of about 0.03 to 4 pounds per acre of test compound per cup. The treated cups are then placed on greenhouse benches, watered and cared for in accordance with conventional greenhouse procedures. Three or four weeks after treatment, the tests are terminated and each cup is examined and rated according to the rating system set forth below. The herbicidal proficiency of the active ingredients of the present invention is evident from the test results which are reported in the tables below.

| RATING SYSTEM | |
|---|---|
| Rating System | % Difference in Growth from the Check* |
| 0 - no effect | 0 |
| 1 - possible effect | 1–10 |
| 2 - slight effect | 11–25 |
| 3 - moderate effect | 26–40 |
| 5 - definite injury | 41–60 |
| 6 - herbicidal effect | 61–75 |
| 7 - good herbicidal effect | 76–90 |
| 8 - approaching complete kill | 91–99 |
| 9 - complete kill | 100 |

4 - abnormal growth, i.e., a definite physiological malformation but with an over-all effect less than a 5 on the rating scale.
*Based on visual determination of stand, size, vigor, chlorosis, growth malformation and over-all plant appearance.

PLANT ABBREVIATIONS

| | |
|---|---|
| CR - Crabgrass | BA - Barnyard grass |
| VEL - Velvet leaf | FOX - Green foxtail |
| PI - Pigweed | MG - Annual Morning-glow |
| LA - Lambsquarters | COT - Cotton |
| COR - Corn | SB - Sugarbeets |
| WO - Wild oats | SOY - Soybean |

TABLE VI

XVI

| | | | | Species - Greenhouse Soil | | | | | | | | | | |
|---|---|---|---|---|---|---|---|---|---|---|---|---|---|---|
| Z | $R_1$ | $R_2$ | Rate lb./acre | CR | VEL | PI | LA | COR | WO | BA | FOX | MG | COT | SB | SOY |
| $CH_3$ | $CH_3$ | $CH_3$ | 4 | 7 | 0 | 8 | 5 | 0 | 1 | 8 | 9 | 0 | 0 | 0 | 0 |
| | | | 2 | 6 | 0 | 8 | 2 | 0 | 0 | 6 | 8 | 0 | 0 | 0 | 0 |

TABLE VI-continued

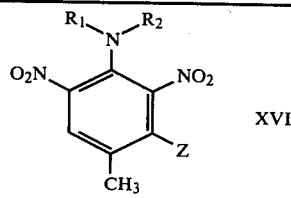
XVI

| Z | $R_1$ | $R_2$ | Rate lb./acre | CR | VEL | PI | LA | COR | WO | BA | FOX | MG | COT | SB | SOY |
|---|---|---|---|---|---|---|---|---|---|---|---|---|---|---|---|
| $CH_3$ | $CH_2CH=CH_2$ | $CH_2CH=CH_2$ | 4 | 9 | 0 | 9 | 6 | 1 | 0 | 9 | 9 | 0 | 0 | 0 | 0 |
| | | | 2 | 6 | 0 | 2 | 5 | 1 | 0 | 7 | 7 | 0 | 0 | 0 | 0 |
| | | | 1 | 7 | 0 | 0 | 0 | 0 | 0 | 5 | 3 | 0 | 0 | 0 | 0 |
| $CH_3$ | $CH_3$ | cyclohexyl | 4 | 9 | 0 | 7 | 6 | 0 | 0 | 8 | 9 | 0 | 0 | 0 | 0 |
| | | | 2 | 8 | 0 | 0 | 0 | 0 | 0 | 3 | 3 | 0 | 0 | 0 | 0 |
| | | | 1 | 3 | 0 | 0 | 0 | 0 | 0 | 1 | 1 | 0 | 0 | 0 | 0 |
| $CH_3$ | H | $CH_2CH=CH_2$ | 4 | 9 | 0 | 8 | 7 | 3 | 0 | 9 | 9 | 0 | 3 | 1 | 0 |
| | | | 2 | 9 | 0 | 8 | 5 | 0 | 0 | 7 | 8 | 0 | 0 | 0 | 0 |
| | | | 1 | 8 | 0 | 5 | 5 | 0 | 0 | 6 | 5 | 0 | 0 | 0 | 0 |
| $CH_3$ | H | $C_4H_9$-i | 4 | 9 | 0 | 8 | 6 | 3 | 0 | 8 | 9 | 0 | 0 | 2 | 0 |
| | | | 2 | 9 | 1 | 6 | 0 | 0 | 2 | 5 | 8 | 0 | 0 | 0 | 0 |
| | | | 1 | 7 | 0 | 0 | 0 | 0 | 0 | 3 | 5 | 0 | 0 | 0 | 0 |
| $CH_3$ | H | $C_4H_9$-tert | 4 | 7 | 0 | 7 | 8 | 0 | 0 | 6 | 7 | 0 | 0 | 2 | 0 |
| | | | 2 | 6 | 0 | 3 | 2 | 1 | 0 | 2 | 5 | 0 | 0 | 1 | 2 |
| $CH_3$ | H | $CH(CH_2CH_2CH_3)_2$ | 4 | 9 | 6 | 9 | 8 | 0 | 0 | 7 | 9 | 2 | — | 7 | 3 |
| | | | 2 | 9 | 2 | 8 | 8 | 0 | 0 | 7 | 8 | 0 | 0 | 6 | 0 |
| | | | 1 | 8 | 0 | 8 | 6 | 0 | 0 | 5 | 7 | 0 | 0 | 7 | 0 |
| $CH_3$ | H | $CH_3CH(CH_2)_4CH_3$ | 4 | 2 | 0 | 0 | 0 | 0 | 0 | 0 | 3 | 0 | 0 | 3 | 0 |
| $CH_3$ | H | $C_2H_5CHCH_2CH_2CH_3$ | 4 | 9 | 7 | 9 | 8 | 5 | 5 | 9 | 9 | 6 | 0 | 8 | 0 |
| | | | 2 | 9 | 7 | 8 | 8 | 0 | 3 | 8 | 9 | 2 | 0 | 8 | 0 |
| | | | 1 | 9 | 5 | 8 | 8 | 0 | 1 | 8 | 9 | 0 | 0 | 6 | 0 |
| | | | ½ | 9 | 2 | 6 | 8 | 0 | 1 | 6 | 8 | 0 | 0 | 2 | 0 |
| | | | ¼ | 8 | 0 | 5 | 7 | 0 | 0 | 5 | 6 | 0 | 0 | 0 | 0 |
| $CH_3$ | H | $CH_2C(CH_3)_3$ | 4 | 5 | 0 | 2 | 0 | 0 | 0 | 2 | 7 | 0 | 0 | 0 | 0 |
| $CH_3$ | $C_2H_5$ | $C_2H_5$ | 4 | 9 | 0 | 8 | 7 | 2 | 5 | 9 | 9 | 0 | 0 | 0 | 0 |
| | | | 2 | 9 | 0 | 8 | 3 | 3 | 2 | 9 | 9 | 0 | 1 | 3 | 0 |
| | | | 1 | 9 | 0 | 7 | 3 | 0 | 1 | 9 | 9 | 0 | 0 | 0 | 0 |
| $CH_3$ | H | $C_4H_9$-n | 4 | 9 | 0 | 7 | 6 | 3 | 1 | 8 | 9 | 1 | 0 | 0 | 0 |
| | | | 2 | 7 | 0 | 0 | 0 | 0 | 0 | 1 | 9 | 1 | 0 | 0 | 0 |
| | | | 1 | 7 | 0 | 0 | 0 | 0 | 0 | 0 | 0 | 0 | 0 | 0 | 0 |
| $CH_3$ | H | $CH_3CH-CH_2CH_3$ | 4 | 9 | 8 | 8 | 8 | 3 | 2 | 9 | 9 | 2 | 0 | 8 | 3 |
| | | | 2 | 9 | 8 | 8 | 8 | 3 | 0 | 9 | 9 | 0 | 0 | 8 | 0 |
| | | | 1 | 9 | 5 | 7 | 8 | 0 | 0 | 9 | 9 | 0 | 0 | 7 | 0 |
| | | | ½ | 9 | 0 | 3 | 7 | 0 | 0 | 7 | 9 | 0 | 0 | 0 | 0 |
| | | | ¼ | 8 | 0 | 0 | 5 | 0 | 0 | 5 | 5 | 0 | 0 | 0 | 0 |
| $CH_3$ | $C_4H_9$-n | $C_4H_9$-n | 4 | 8 | 1 | 5 | 2 | 2 | 0 | 2 | 8 | 0 | 7 | 0 | 0 |
| | | | 2 | 8 | 0 | 1 | 0 | 0 | 0 | 1 | 5 | 0 | 1 | 2 | 0 |
| $CH_3$ | H | $C_3H_7$-i | 4 | 9 | 3 | 9 | 8 | 0 | 2 | 9 | 9 | 0 | 0 | 7 | 0 |
| | | | 2 | 9 | 1 | 8 | 8 | 1 | 1 | 9 | 9 | 0 | 0 | 5 | 0 |
| | | | 1 | 9 | 1 | 7 | 7 | 0 | 0 | 9 | 9 | 0 | 0 | 0 | 0 |
| | | | ½ | 9 | 0 | 2 | 2 | 1 | 0 | 7 | 9 | 0 | 0 | 0 | 0 |
| $CH_3$ | $C_3H_7$-n | $C_3H_7$-n | 4 | 9 | 3 | 9 | 7 | 0 | 2 | 9 | 9 | 4 | 1 | 0 | 0 |
| | | | 2 | 9 | 1 | 9 | 7 | 0 | 0 | 8 | 9 | 0 | 0 | 0 | 0 |
| | | | 1 | 9 | 0 | 8 | 3 | 0 | 0 | 7 | 9 | 0 | 0 | 0 | 0 |
| | | | ½ | 8 | 0 | 6 | 2 | 0 | 0 | 5 | 9 | 0 | 0 | 0 | 0 |
| $CH_3$ | $C_2H_5$ | $C_4H_9$-n | 4 | 9 | 0 | 9 | 7 | 0 | 0 | 9 | 9 | 0 | 0 | 0 | 0 |
| | | | 2 | 8 | 0 | 8 | 6 | 1 | 0 | 8 | 9 | 0 | 0 | 0 | 0 |
| | | | 1 | 3 | 0 | 6 | 1 | 0 | 0 | 6 | 8 | 0 | 0 | 0 | 0 |
| | | | ½ | 3 | 0 | 2 | 0 | 0 | 0 | 1 | 6 | 0 | 0 | 0 | 0 |
| $CH_3$ | H | $C_3H_7$-n | 4 | 9 | 0 | 8 | 8 | 0 | 7 | 9 | 3 | 0 | 0 | 0 | 2 |
| | | | 2 | 9 | 0 | 8 | 7 | 0 | 2 | 8 | 8 | 0 | 0 | 0 | 0 |
| | | | 1 | 9 | 0 | 7 | 1 | 0 | 0 | 6 | 8 | 0 | 0 | 0 | 0 |
| $CH_3$ | | tetrahydropyranyl | 4 | 7 | 0 | 8 | 7 | 0 | 0 | 9 | 5 | 0 | 0 | 0 | 0 |
| | | | 2 | 2 | 0 | 7 | 0 | 0 | 0 | 6 | 3 | 0 | 0 | 0 | 0 |
| | | | 1 | 1 | 0 | 0 | 0 | 0 | 0 | 3 | 0 | 0 | 5 | 0 | 0 |
| $CH_3$ | H | $CH_3CHCH_2CH(CH_3)_2$ | 4 | 9 | 3 | 8 | 7 | 0 | 0 | 9 | 9 | 0 | 0 | 1 | 0 |
| | | | 2 | 9 | 2 | 7 | 7 | 0 | 0 | 8 | 9 | 2 | 0 | 1 | 0 |
| | | | 1 | 9 | 0 | 7 | 7 | 0 | 0 | 6 | 9 | 0 | 5 | 1 | 0 |
| | | | ½ | 8 | 0 | 6 | 6 | 0 | 0 | 3 | 7 | 0 | 0 | 0 | 0 |
| | | | ¼ | 6 | 0 | 2 | 5 | 0 | 0 | 0 | 0 | 0 | 0 | 0 | 0 |
| $CH_3$ | $C_2H_5$ | $C_3H_7$-n | 4 | 9 | 0 | 6 | 7 | 0 | 2 | 9 | 9 | 0 | 0 | 0 | 0 |
| | | | 2 | 9 | 0 | 7 | 7 | 0 | 2 | 9 | 9 | 0 | 0 | 0 | 0 |
| | | | 1 | 8 | 0 | 0 | 3 | 0 | 0 | 9 | 9 | 0 | 0 | 0 | 0 |
| | | | ½ | 6 | 0 | 0 | 0 | 0 | 0 | 6 | 7 | 0 | 0 | 0 | 0 |
| | | | ¼ | 2 | 2 | 0 | 2 | 0 | 0 | 2 | 8 | 0 | 0 | 0 | 0 |
| $CH_3$ | H | $C_2H_5CHC_2H_5$ | 4 | 9 | 7 | 8 | 8 | 7 | 5 | 9 | 9 | 7 | 5 | 5 | 3 |
| | | | 2 | 9 | 7 | 8 | 8 | 6 | 2 | 9 | 9 | 7 | 2 | 5 | 2 |
| | | | 1 | 9 | 6 | 7 | 8 | 2 | 0 | 7 | 9 | 6 | 1 | 2 | 1 |

TABLE VI-continued

XVI

| Z | R₁ | R₂ | Rate lb./acre | CR | VEL | PI | LA | COR | WO | BA | FOX | MG | COT | SB | SOY |
|---|----|----|---------------|----|----|----|----|----|----|----|----|----|----|----|----|
| | | | ½ | 9 | 5 | 6 | 8 | 1 | 0 | 8 | 9 | 3 | 0 | 1 | 0 |
| | | | ¼ | 9 | 5 | 6 | 7 | — | 0 | 5 | 9 | 1 | 0 | 0 | 0 |
| $CH_3$ | H | $CH_3CHC_3H_7$ | 4 | 9 | 7 | 8 | 8 | 8 | 3 | 9 | 9 | 5 | 0 | 6 | 0 |
| | | | 2 | 9 | 2 | 8 | 8 | 2 | 2 | 9 | 9 | 6 | 0 | 5 | 0 |
| | | | 1 | 9 | 2 | 8 | 8 | 0 | 0 | 8 | 9 | 5 | 9 | 2 | 0 |
| | | | ½ | 9 | 0 | 5 | 7 | 0 | 0 | 3 | 8 | 2 | 0 | 0 | 0 |
| | | | ¼ | 9 | 1 | 2 | 6 | 0 | 0 | 2 | 5 | 0 | 0 | 0 | 0 |
| $CH_3$ | H | $CH_2CH_2CH(CH_3)_2$ | 4 | 9 | 0 | 6 | 6 | 0 | 0 | 6 | 5 | 0 | 0 | 0 | 0 |
| | | | 2 | 7 | 0 | 0 | 2 | 0 | 0 | 3 | 3 | 0 | 0 | 0 | 0 |
| $CH_3$ | | (cyclohexyl) | 4 | 9 | 1 | 5 | 7 | 7 | 0 | 6 | 8 | 2 | 0 | 0 | 0 |
| | | | 2 | 8 | 0 | 2 | 6 | 2 | 0 | 2 | 7 | 0 | 0 | 0 | 0 |
| | | | 1 | 7 | 0 | 0 | 2 | 3 | 0 | 0 | 5 | 0 | 0 | 0 | 0 |
| $CH_3$ | | (cyclopentyl) | 4 | 9 | 2 | 5 | 8 | 0 | 0 | 9 | 9 | 2 | 0 | 0 | 1 |
| | | | 2 | 9 | 0 | 3 | 7 | 0 | 0 | 5 | 8 | 0 | 0 | 0 | 0 |
| | | | 1 | 7 | 0 | 0 | 3 | 0 | 0 | 2 | 7 | 0 | 0 | 0 | 0 |
| $CH_3$ | H | $CH_3CHCH(CH_3)_2$ | 4 | 9 | 7 | 8 | 8 | 1 | 3 | 8 | 9 | 3 | 0 | 6 | 0 |
| | | | 2 | 9 | 5 | 7 | 8 | 0 | 0 | 7 | 9 | 2 | 0 | 3 | 0 |
| | | | 1 | 9 | 3 | 6 | 8 | 0 | 0 | 3 | 7 | 0 | 0 | 1 | 0 |
| | | | ½ | 8 | 0 | 2 | 7 | — | 0 | 2 | 5 | 0 | 1 | 0 | 0 |
| | | | ¼ | 7 | 0 | 2 | 3 | 1 | 0 | 1 | 1 | 0 | 0 | 0 | 0 |
| $CH_3$ | H | $CH_3CHCH_2CH_2CH(CH_3)_2$ | 4 | 5 | 0 | 0 | 0 | 0 | 0 | 0 | 2 | 0 | 0 | 0 | 0 |
| $CH_3$ | H | $CH_3CHC_4H_9$-t | 4 | 5 | 0 | 2 | 0 | 0 | 8 | 3 | 0 | 0 | 0 | 0 | 0 |
| $CH_3$ | H | (tetrahydropyranyl dimethyl) | 4 | 9 | 0 | 0 | 0 | 0 | 0 | 8 | 8 | 3 | 0 | 2 | 0 |
| | | | 2 | 8 | 0 | 0 | 0 | 0 | 0 | 5 | 7 | 3 | 0 | 0 | 0 |
| | | | 1 | 6 | 0 | 0 | 0 | 0 | 0 | 0 | 2 | 3 | 0 | 0 | 0 |
| $CH_3$ | H | $C_4H_9CHCH_3$ | 4 | 9 | 2 | 7 | 8 | 0 | 1 | 8 | 9 | 0 | 0 | 2 | 0 |
| | | | 2 | 9 | 0 | 6 | 6 | 0 | 0 | 7 | 8 | 0 | 0 | 0 | 0 |
| | | | 1 | 8 | 0 | 3 | 3 | 0 | 0 | 5 | 6 | 0 | 0 | 0 | 0 |
| | | | ½ | 7 | 0 | 0 | 2 | 0 | 0 | 0 | 0 | 0 | 0 | 0 | 0 |

TABLE VII

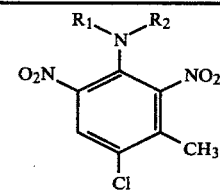

XVII

| R₁ | R₂ | Rate lb./acre | CR | VEL | PI | LA | COR | WO | BA | FOX | MG | COT | CB | SOY |
|----|----|---------------|----|----|----|----|----|----|----|----|----|----|----|----|
| H | $C_3H_7$-n | 4 | 9 | 0 | 8 | 8 | 3 | 0 | 8 | 8 | 0 | 0 | 3 | 0 |
| | | 2 | 9 | 0 | 7 | 7 | 0 | 0 | 6 | 6 | 0 | 0 | 0 | 0 |
| | | 1 | 5 | 0 | 6 | 3 | 5 | 0 | 3 | 3 | 0 | 0 | 0 | 0 |
| $C_3H_7$-n | $C_3H_7$-n | 4 | 9 | 3 | 8 | 8 | 0 | 0 | 9 | 9 | 0 | 0 | 1 | 1 |
| | | 2 | 9 | 0 | 7 | 7 | 0 | 0 | 8 | 9 | 0 | 0 | 0 | 0 |
| | | 1 | 9 | 0 | 7 | 6 | 0 | 0 | 6 | 8 | 0 | 0 | 0 | 0 |
| H | $C_6H_{13}$-n | 2 | 3 | | | | | | 0 | 0 | | | | |
| | | 1 | 3 | | | | | | 0 | 0 | | | | |
| H | $CH_2CH=CH_2$ | 2 | 8 | | | | | | 1 | 7 | | | | |
| H | $C_3H_7$-i | 2 | 9 | | | | | | 8 | 9 | | | | |
| | | 1 | 8 | | | | | | 7 | 6 | | | | |
| | | ½ | 5 | | | | | | 3 | 3 | | | | |
| $CH_2CH=CH_2$ | $CH_2CH=CH_2$ | 2 | 9 | | | | | | 8 | 9 | | | | |
| | | 1 | 7 | | | | | | 6 | 5 | | | | |
| | | ½ | 6 | | | | | | 5 | 2 | | | | |
| | | ¼ | 6 | | | | | | 3 | 3 | | | | |
| H | $CH_3CHC_2H_5$ | 2 | 9 | | | | | | 9 | 9 | | | | |
| | | 1 | 9 | | | | | | 8 | 9 | | | | |

TABLE VII-continued

XVII

Structure: Benzene ring with $R_1R_2N-$ group, two $NO_2$ groups (positions 2,6), $CH_3$ and $Cl$ substituents.

| $R_1$ | $R_2$ | Rate lb./acre | CR | VEL | PI | LA | COR | WO | BA | FOX | MG | COT | CB | SOY |
|---|---|---|---|---|---|---|---|---|---|---|---|---|---|---|
| $C_2H_5$ | $C_2H_5$ | 1/2 | 9 | | | | | | 7 | 7 | | | | |
| | | 1/4 | 8 | | | | | | 6 | 8 | | | | |
| | | 2 | 9 | | | | | | 9 | 9 | | | | |
| | | 1 | 8 | | | | | | 8 | 7 | | | | |
| | | 1/2 | 3 | | | | | | 5 | 6 | | | | |
| | | 1/4 | 0 | | | | | | 3 | 1 | | | | |
| H | tetrahydropyranyl (O-containing ring) | 4 | 5 | 1 | 0 | 5 | 5 | 0 | 0 | 0 | 3 | 0 | 0 | 0 |
| H | $CH_3CHCH_2CH(CH_3)_2$ | 4 | 9 | 3 | 9 | 7 | 0 | 0 | 7 | 9 | 3 | 0 | 5 | 1 |
| | | 2 | 9 | 2 | 8 | 6 | 0 | 0 | 3 | 9 | 2 | 0 | 3 | 0 |
| | | 1 | 9 | 0 | 8 | 6 | 0 | 0 | 5 | 8 | 0 | 0 | 1 | 0 |
| H | cyclohexyl | 4 | 9 | 0 | 5 | 2 | 0 | 0 | 2 | 3 | 2 | 0 | 0 | 1 |
| | | 2 | 7 | 1 | 1 | 1 | 0 | 0 | 1 | 2 | 5 | 0 | 0 | 1 |
| H | $C(CH_3)_3$ | 4 | 5 | 2 | 2 | 0 | 0 | 0 | 0 | 3 | 0 | 0 | 1 | 0 |
| | | 2 | 2 | 0 | 0 | 0 | 0 | 0 | 0 | 0 | 0 | 0 | 1 | 0 |
| H | $CH_2CH(CH_3)_2$ | 4 | 8 | 2 | 3 | 0 | 0 | 0 | 6 | 7 | 0 | 0 | 0 | 0 |
| | | 2 | 6 | 0 | 0 | 0 | 0 | 0 | 3 | 5 | 0 | 0 | 0 | 0 |
| H | $C_2H_5CHC_2H_5$ | 4 | 9 | 7 | 9 | 8 | 0 | 2 | 9 | 9 | 5 | 0 | 8 | 0 |
| | | 2 | 9 | 6 | 8 | 7 | 0 | 2 | 7 | 9 | 5 | 0 | 7 | 0 |
| | | 1 | 9 | 5 | 7 | 7 | 0 | 1 | 5 | 9 | 6 | 0 | 6 | 0 |
| | | 1/2 | 9 | 3 | 6 | 6 | 0 | 0 | 1 | 9 | 2 | 0 | 3 | 0 |
| | | 1/4 | 7 | 0 | 2 | 5 | 0 | 0 | 2 | 5 | 0 | 0 | 0 | 0 |
| $CH_3$ | $CH_3$ | 4 | 3 | 0 | 0 | 5 | 0 | 1 | 2 | 5 | 0 | 0 | 0 | 0 |
| H | $CH_3CHC_3H_7$-n | 4 | 9 | 6 | 8 | 8 | 3 | 0 | 9 | 9 | 0 | 0 | 8 | 0 |
| | | 2 | 9 | 5 | 8 | 8 | 2 | 0 | 7 | 9 | 0 | 0 | 7 | 0 |
| | | 1 | 9 | 2 | 7 | 7 | 0 | 0 | 7 | 7 | 0 | 0 | 5 | 0 |
| | | 1/2 | 8 | 2 | 5 | 5 | 0 | 0 | 6 | 6 | 0 | 0 | 2 | 0 |
| | | 1/4 | 8 | 0 | 0 | 0 | 0 | 0 | 3 | 2 | 0 | 0 | 0 | 0 |

TABLE VIII

XVIII

Structure: Benzene ring with $R_1R_2N-$ group, two $NO_2$ groups, $CH_3$ and $CF_3$ substituents.

| $R_1$ | $R_2$ | Rate lb./acre | CR | VEL | PI | LA | COR | WO | BA | FOX | MG | COT | SB | SOY |
|---|---|---|---|---|---|---|---|---|---|---|---|---|---|---|
| $C_3H_7$-n | $C_3H_7$-n | 4 | 9 | 3 | 8 | 7 | 3 | 2 | 9 | 9 | 3 | 0 | 0 | 3 |
| | | 2 | 9 | 0 | 8 | 6 | 2 | 3 | 8 | 9 | 0 | 0 | 0 | 3 |
| | | 1 | 9 | 0 | 6 | 6 | 0 | 2 | 8 | 9 | 0 | 0 | 0 | 0 |
| | | 1/2 | 7 | 0 | 3 | 3 | 0 | 2 | 6 | 7 | 0 | 0 | 0 | 0 |
| H | $CH_3CHC_2H_5$ | 4 | 9 | 7 | 8 | 8 | 5 | 3 | 9 | 9 | 7 | 5 | 7 | 7 |
| | | 2 | 9 | 7 | 8 | 8 | 5 | 2 | 9 | 9 | 7 | 0 | 6 | 5 |
| | | 1 | 9 | 6 | 7 | 7 | 3 | 2 | 9 | 9 | 6 | 0 | 5 | 2 |
| | | 1/2 | 9 | 2 | 6 | 7 | 0 | 0 | 8 | 9 | 0 | 0 | 3 | 0 |
| | | 1/4 | 7 | 2 | 3 | 5 | 0 | 0 | 7 | 7 | 0 | 0 | 2 | 0 |
| H | $C_3H_7$-i | 4 | 9 | 5 | 7 | 7 | 0 | 1 | 9 | 9 | 0 | 0 | 3 | 0 |
| | | 2 | 9 | 0 | 6 | 6 | 0 | 0 | 8 | 9 | 0 | 0 | 0 | 0 |
| | | 1 | 0 | 3 | 0 | 0 | 0 | 7 | 8 | 0 | 0 | 1 | 0 | |
| | | 1/2 | 7 | 0 | 0 | 1 | 0 | 0 | 3 | 6 | 0 | 0 | 0 | 0 |
| $CH_3$ | $CH_3$ | 4 | 3 | 0 | 0 | 2 | 6 | 0 | 3 | 3 | 0 | 0 | 0 | 0 |
| $C_2H_5$ | $C_2H_5$ | 4 | 9 | 0 | 8 | 7 | 2 | 3 | 9 | 9 | 2 | 0 | 3 | 0 |
| | | 2 | 9 | 0 | 7 | 5 | 1 | 0 | 8 | 9 | 2 | 0 | 2 | 0 |
| | | 1 | 8 | 0 | 3 | 2 | 0 | 0 | 8 | 8 | 1 | 0 | 1 | 0 |
| | | 1/2 | 7 | 0 | 0 | 0 | 0 | 0 | 6 | 5 | 3 | 0 | 0 | 0 |
| H | $C_2H_5CHC_2H_5$ | 4 | 9 | 8 | 9 | 9 | 5 | 5 | 9 | 9 | 7 | 7 | 8 | 7 |
| | | 2 | 9 | 8 | 8 | 8 | 3 | 3 | 9 | 9 | 7 | 5 | 9 | 7 |
| | | 1 | 9 | 7 | 8 | 8 | 3 | 2 | 9 | 9 | 6 | — | 7 | 5 |

TABLE VIII-continued

XVIII

Structure: 2,6-dinitro-3-methyl-4-trifluoromethyl-N,N-disubstituted aniline with $R_1, R_2$ on N, $O_2N$ and $NO_2$ at ortho positions, $CH_3$ and $CF_3$ on ring.

| $R_1$ | $R_2$ | Rate lb./acre | CR | VEL | PI | LA | COR | WO | BA | FOX | MG | COT | SB | SOY |
|---|---|---|---|---|---|---|---|---|---|---|---|---|---|---|
|  |  | ½ | 9 | 5 | 7 | 8 | 0 | 1 | 8 | 9 | 5 | 0 | 5 | 0 |
|  |  | ¼ | 9 | 5 | 7 | 7 | 0 | 0 | 7 | 8 | 2 | 0 | 2 | 0 |

TABLE IX

XX

Structure: aniline with $NR_1R_2$, $O_2N$, $NO_2$, Y, Z substituents.

| Y | Z | $R_1$ | $R_2$ | Rate lb./acre | CR | VEL | PI | LA | COR | WO | BA | FOX | MG | COT | SB | SOY |
|---|---|---|---|---|---|---|---|---|---|---|---|---|---|---|---|---|
| $CH_3$ | $CH_3$ | H | —CH(CH$_3$)CH$_2$OCH$_3$ | 4 | 9 | 7 | 9 | 9 | 0 | 5 | 9 | 9 | 5 | 0 | 8 | 5 |
|  |  |  |  | 2 | 9 | 6 | 8 | 8 | 0 | 0 | 8 | 9 | 3 | 0 | 8 | 0 |
|  |  |  |  | 1 | 9 | 3 | 7 | 8 | 0 | 0 | 8 | 7 | 0 | 0 | 6 | 0 |
| $CH_3$ | $CH_3$ | $CH_3$ | $CH_2CH_2Cl$ | 4 | 9 | 0 | 6 | 7 | 0 | 0 | 8 | 8 | 1 | 0 | 6 | 0 |
|  |  |  |  | 2 | 9 | 0 | 3 | 3 | 0 | 0 | 7 | 7 | 0 | 0 | 3 | 0 |
| $CH_3$ | $CH_3$ | H | $CH_2CH(OCH_3)_2$ | 4 | 9 | 0 | 5 | 7 | 0 | 0 | 8 | 7 | 5 | 0 | 3 | 0 |
|  |  |  |  | 2 | 8 | 0 | 3 | 5 | 0 | 0 | 6 | 3 | 3 | 0 | 0 | 0 |
|  |  |  |  | 1 | 7 | 0 | 0 | 3 | 0 | 0 | 2 | 0 | 0 | 0 | 0 | 0 |
| $CH_3$ | $CH_3$ | H | $CH(C_2H_5)CH_2OCH_3$ | 4 | 9 | 7 | 9 | 8 | 5 | 5 | 9 | 9 | 7 | 0 | 8 | 0 |
|  |  |  |  | 2 | 9 | 7 | 8 | 8 | 0 | 3 | 9 | 9 | 3 | 0 | 7 | 0 |
|  |  |  |  | 1 | 9 | 2 | 8 | 8 | 0 | 0 | 9 | 9 | 0 | 0 | 6 | 0 |
| $CH_3$ | $CH_3$ | H | $CH_3(CH_3)CH_2Cl$ | 4 | 9 | 2 | 5 | 8 | 0 | 0 | 8 | 9 | 0 | 0 | 6 | 0 |
|  |  |  |  | 2 | 9 | 0 | 3 | 8 | 0 | 0 | 7 | 9 | 0 | 0 | 0 | 0 |
|  |  |  |  | 1 | 9 | 0 | 0 | 7 | 0 | 0 | 3 | 9 | 0 | 0 | 0 | 0 |
| $CH_3$ | $CH_3$ | H | $CH(C_2H_5)CH_2Cl$ | 4 | 9 | 7 | 7 | 8 | 3 | 3 | 9 | 9 | 3 | 0 | 7 | 0 |
|  |  |  |  | 2 | 9 | 7 | 5 | 8 | 0 | 0 | 8 | 9 | 0 | 0 | 7 | 0 |
|  |  |  |  | 1 | 9 | 3 | 3 | 8 | 0 | 0 | 8 | 9 | 0 | 0 | 5 | 0 |
| $CH_3$ | $CH_3$ | H | $CH_2CH_2CH_2OCH_3$ | 4 | 9 | 1 | 5 | 3 | 0 | 0 | 5 | 3 | 2 | 0 | 0 | 0 |
|  |  |  |  | 2 | 7 | 0 | 0 | 2 | 0 | 0 | 2 | 0 | 1 | 0 | 0 | 0 |
| Cl | $CH_3$ | H | $CH_2CH_2CH_2OCH_3$ | 4 | 9 | 6 | 8 | 8 | 0 | 0 | 8 | 8 | 2 | 0 | 7 | 3 |
|  |  |  |  | 2 | 9 | 7 | 7 | 8 | 0 | 0 | 7 | 6 | 0 | 0 | 7 | 2 |
|  |  |  |  | 1 | 9 | 3 | 6 | 8 | 0 | 0 | 7 | 2 | 0 | 0 | 5 | 0 |

The herbicidal activity of various compounds of the present invention is demonstrated by the following tests, wherein seeds of monocotyledonous and dicotyledonous plants are planted in the top half-inch of soil in small plastic pots and sprayed with a solution of test compound. All spray applications are made to a dry soil surface through nozzles designed to deliver 86 gallons per acre of spray solution. Immediately after treatment, the pots are labeled, moved to a greenhouse, and watered. Three weeks after treatment, the herbicide activity is recorded using the Herbicidal Activity rating system reported below.

From the data reported in the table below, it can be seen that (1) the racemic compounds are highly active herbicidal agents; (2) the dextrorotatory (+) isomers are less active than the racemic compounds, but still effective as herbicidal agents at higher rates of application; and (3) the levorotatory (−) isomers are much more effective as herbicidal agents than either the corresponding racemic compound or the corresponding dextrorotatory (+) isomer.

SPECIES LIST

| Code | Common Name | Scientific Name |
|---|---|---|
| LA | Lambsquarters | *Chenopodium album* |
| PI | Pigweed | *Amaranthus retroflexus* |
| MG | Morning-glory | *Ipomoea hederacea* |
| BA | Barnyard grass | *Echinochloa crusgalli* |
| CR | Crab grass | *Digitairia sanguinalis* |
| FO | Green foxtail | *Setaria viridis* |
| WO | Wild oat | *Avena fatua* |
| CN | Corn | *Zea mays* |
| CO | Cotton | *Gossypium hirsutum* |
| SY | Soybean | *Glycine max* |
| SB | Sugar beet | *Beta vulgaris* |
| VL | Velvet leaf | *Abutilon Theophrasti* |

HERBICIDAL ACTIVITY INDEX

| Rating Scale | Observation | *% Difference in Growth from Checks |
|---|---|---|
| 9 | Complete kill | 100 |
| 8 | Approaching complete kill | 91–99 |
| 7 | Good herbicidal effect | 76–90 |
| 6 | Herbicidal effect | 61–75 |

| -continued | | |
|---|---|---|
| HERBICIDAL ACTIVITY INDEX | | |
| Rating Scale | Observation | *% Difference in Growth from Checks |
| 5 | Definite injury | 41–60 |
| 4 | (See Below) | — |
| 3 | Moderate effect | 26–40 |
| 2 | Slight effect | 11–25 |
| 1 | Possible effect | 1–10 |

| -continued | | |
|---|---|---|
| HERBICIDAL ACTIVITY INDEX | | |
| Rating Scale | Observation | *% Difference in Growth from Checks |
| 0 | No effect | 0 |

4 - Reserved for abnormal plant growth, i.e., a definite physiological malformation but with an over-all effect of less than 5 on the rating scale.
*Based on visual determination of stand, size, vigor, chlorosis.

TABLE X

Herbicidal Activity of Optically Active and Racemic Dinitroaniline Compounds

| Compound | Rate lb./Acre | LA | PI | MG | BA | CR | FO | WO | CN | CO | SY | SB | VL |
|---|---|---|---|---|---|---|---|---|---|---|---|---|---|
| NH—CH(C$_2$H$_5$)—CH$_2$—OCH$_3$ on 2,6-dinitro-3,4-dimethylaniline (−) | 4 | 8 | 9 | 8 | 9 | 9 | 9 | 0 | 5 | 0 | — | 8 | 8 |
|  | 2 | 8 | 9 | 6 | 9 | 9 | 9 | 0 | 5 | 0 | 2 | 8 | 2 |
|  | 1 | 8 | 8 | 3 | 9 | 9 | 9 | 0 | 0 | 0 | 0 | 6 | 7 |
|  | 1/2 | 8 | 7 | 0 | 8 | 9 | 9 | 0 | 0 | 0 | 0 | 0 | 2 |
|  | 1/4 | 7 | 3 | 0 | 6 | 9 | 7 | 0 | 0 | 0 | 0 | 0 | 0 |
|  | 1/8 | 5 | 1 | 0 | 2 | 9 | 3 | 0 | 0 | 0 | 0 | 0 | 0 |
|  | 1/16 | 0 | 0 | 0 | 0 | 8 | 1 | 0 | 0 | 0 | 0 | 0 | 0 |
| NH—CH(C$_2$H$_5$)—CH$_2$—OCH$_3$ on 2,6-dinitro-3,4-dimethylaniline (±) | 2 | 8 | 8 | 0 | 9 | 9 | 9 | 0 | 0 | 0 | 0 | 8 | 7 |
|  | 1 | 8 | 7 | 0 | 7 | 9 | 9 | 0 | 0 | 0 | 0 | 0 | 0 |
|  | 1/2 | 8 | 6 | 0 | 5 | 9 | 8 | 0 | 0 | 0 | 0 | 0 | 0 |
|  | 1/4 | 7 | 0 | 0 | 0 | 9 | 5 | 0 | 0 | 0 | 0 | 0 | 0 |
|  | 1/8 | 2 | 0 | 0 | 0 | 6 | 2 | 0 | 0 | 0 | 0 | 0 | 0 |
|  | 1/16 | 0 | 0 | 0 | 0 | 1 | 3 | 0 | 0 | 0 | 0 | 0 | 0 |
| NH—CH(C$_2$H$_5$)—CH$_2$—OCH$_3$ on 2,6-dinitro-3,4-dimethylaniline (+) | 4 | 8 | 8 | 6 | 9 | 9 | 9 | 0 | 0 | 0 | 0 | 7 | 6 |
|  | 2 | 8 | 7 | 0 | 9 | 9 | 8 | 0 | 0 | 0 | 0 | 6 | 5 |
|  | 1 | 8 | 3 | 0 | 7 | 8 | 7 | 0 | 0 | 0 | 0 | 2 | 0 |
|  | 1/2 | 7 | 1 | 0 | 5 | 7 | 5 | 0 | 0 | 0 | 0 | 0 | 0 |
|  | 1/4 | 2 | 0 | 0 | 0 | 1 | 0 | 0 | 0 | 0 | 0 | 0 | 0 |
|  | 1/8 | 0 | 0 | 0 | 0 | 0 | 0 | 0 | 0 | 0 | 0 | 0 | 0 |
|  | 1/16 | 0 | 0 | 0 | 0 | 0 | 0 | 0 | 0 | 0 | 0 | 0 | 0 |
| NH—CH(CH$_3$)—C$_2$H$_5$ on 2,6-dinitro-3,4-dimethylaniline (−) | 1 | 8 | 8 | 0 | 8 | 9 | 9 | 0 | 0 | 2 | 3 | 3 | 7 |
|  | 1/2 | 8 | 7 | 0 | 8 | 8 | 9 | 0 | 0 | 0 | 0 | 3 | 6 |
|  | 1/4 | 7 | 6 | 0 | 2 | 8 | 8 | 0 | 0 | 0 | 0 | 0 | 0 |
|  | 1/8 | 5 | 5 | 0 | 6 | 6 | 8 | 0 | 0 | 0 | 0 | 0 | 0 |
|  | 1/16 | 3 | 1 | 0 | 2 | 0 | 7 | 0 | 0 | 0 | 0 | 0 | 0 |
| NH—CH(CH$_3$)—C$_2$H$_5$ on 2,6-dinitro-3,4-dimethylaniline (±) | 1 | 8 | 7 | 0 | 8 | 9 | 9 | 0 | 0 | 3 | 2 | 0 | 0 |
|  | 1/2 | 8 | 7 | 0 | 9 | 9 | 9 | 0 | 0 | 0 | 0 | 0 | 0 |
|  | 1/4 | 7 | 6 | 0 | 2 | 8 | 8 | 0 | 0 | 0 | 0 | 0 | 0 |
|  | 1/8 | 0 | 0 | 0 | 0 | 6 | 8 | 3 | 0 | 0 | 0 | 0 | 0 |
|  | 1/16 | 0 | 0 | 0 | 0 | 3 | 7 | 0 | 0 | 0 | 0 | 0 | 0 |
| NH—CH(CH$_3$)—C$_2$H$_5$ on 2,6-dinitro-3,4-dimethylaniline (+) | 1 | 3 | 5 | 0 | 8 | 8 | 8 | 0 | 3 | 2 | 0 | 0 | 0 |
|  | 1/2 | 3 | 0 | 0 | 7 | 2 | 8 | 0 | 0 | 0 | 3 | 0 | 0 |
|  | 1/4 | 1 | 0 | 0 | 7 | 0 | 7 | 0 | 0 | 0 | 0 | 0 | 0 |
|  | 1/8 | 0 | 0 | 0 | 3 | 0 | 1 | 0 | 0 | 0 | 0 | 0 | 0 |
|  | 1/16 | 0 | 0 | 0 | 0 | 0 | 0 | 0 | 0 | 0 | 0 | 0 | 0 |

TABLE X-continued
Herbicidal Activity of Optically Active and Racemic Dinitroaniline Compounds

| Compound | Rate lb./Acre | LA | PI | MG | BA | CR | FO | WO | CN | CO | SY | SB | VL |
|---|---|---|---|---|---|---|---|---|---|---|---|---|---|
| 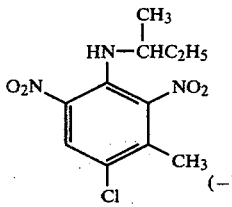 (−) | 2 | 8 | 8 | 5 | 8 | 9 | 8 | 6 | 7 | 0 | 0 | 6 | 7 |
|  | 1 | 8 | 8 | 0 | 8 | 9 | 8 | 3 | 3 | 0 | 0 | 5 | 5 |
|  | ½ | 7 | 7 | 0 | 8 | 8 | 8 | 0 | 0 | 0 | 0 | 3 | 3 |
|  | ¼ | 6 | 6 | 0 | 7 | 8 | 7 | 0 | 0 | 0 | 0 | 2 | 2 |
|  | ⅛ | 6 | 5 | 0 | 5 | 8 | 7 | 0 | 0 | 0 | 0 | 0 | 0 |
| 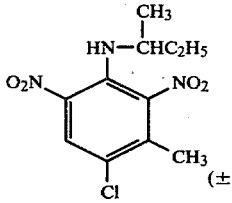 (±) | 2 | 8 | 8 | 2 | 8 | 9 | 8 | 6 | 6 | 0 | 0 | 6 | 6 |
|  | 1 | 8 | 8 | 0 | 8 | 9 | 8 | 0 | 6 | 0 | 0 | 3 | 5 |
|  | ½ | 7 | 7 | 0 | 8 | 8 | 8 | 0 | 0 | 0 | 0 | 0 | 0 |
|  | ¼ | 5 | 5 | 0 | 5 | 8 | 8 | 0 | 0 | 0 | 0 | 0 | 0 |
|  | ⅛ | 0 | 0 | 0 | 0 | 6 | 6 | 0 | 0 | 0 | 0 | 0 | 0 |
| 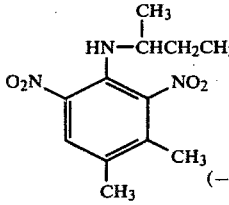 (−) | 2 | 8 | 9 | 2 | 9 | 9 | 8 | 2 | 3 | 0 | 0 | 7 | 6 |
|  | 1 | 8 | 8 | 3 | 8 | 9 | 8 | 3 | 2 | 0 | 0 | 3 | 5 |
|  | ½ | 8 | 8 | 0 | 8 | 9 | 8 | 0 | 0 | 0 | 0 | 0 | 0 |
|  | ¼ | 7 | 7 | 0 | 8 | 9 | 8 | 0 | 0 | 0 | 0 | 0 | 0 |
|  | ⅛ | 5 | 5 | 0 | 7 | 8 | 7 | 0 | 0 | 0 | 0 | 0 | 0 |
| 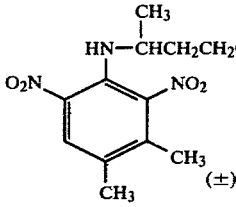 (±) | 2 | 8 | 8 | 0 | 8 | 9 | 7 | 7 | 4 | 0 | 0 | 7 | 6 |
|  | 1 | 8 | 8 | 0 | 8 | 9 | 9 | 5 | 0 | 0 | 0 | 3 | 5 |
|  | ½ | 7 | 7 | 0 | 8 | 8 | 8 | 3 | 0 | 0 | 0 | 0 | 0 |
|  | ¼ | 7 | 5 | 0 | 7 | 8 | 8 | 0 | 0 | 0 | 0 | 0 | 0 |
|  | ⅛ | 3 | 3 | 0 | 3 | 8 | 5 | 0 | 0 | 0 | 0 | 0 | 0 |

EXAMPLE

Following the procedure of the Examples of Tables VI through X, above, and using the rating system described therein and the following species of plants: Sesbania, Mustard, Pigweed, Ragweed, Morningglory, Barnyardgrass, Crabgrass, Green foxtail, Teaweed, Corn, Cotton, Soybeans, Rice and Velvetleaf, test compound is applied as a spray to cups planted with seeds of the above-named plant species. Applications are sufficient to provide from 0.03 lb to 1.0 lb per acre of test compound. The selective preemergence herbicidal activity of the test compound is provided in Table XI below, where it can be seen that (1-ethylpropyl)-3-methoxymethyl)-4-methyl-2,6-dinitroaniline and other compounds are highly selective for controlling undesirable broadleaf weeds and grasses in the presence of monocotyledonous and dicotyledonous crops.

PLANT ABBREVIATIONS

SE-Sesbania (*Sesbania exaltata*)
MU-Mustard (*Brassica kaber*)
PI-Pigweed (*Amaranthus retroflexus*)
RW-Ragweed (*Ambrosia artemisiifolia*)
MG-Morningglory (*Ipomoea purpurea*)
BA-Barnyardgrass (*Echinochloa crusgalli*)
CR-Crabgrass (*Digitaria sanguinalis*)
FO-Green foxtial (*Setaria viridis*)
TW-Teaweed (*Sida spinosa*)
VL-Velvetleaf (*Abutilon theophrasti*)
CN-Corn (*Zea mays*)
CO-Cotton (*Gossypium hirsulum*)
SY-Soybean (*Glycine max*)
RI-Rice (*Oryza sativa*)

4,251,264

TABLE XI
Preemergence Herbicidal Evaluation of

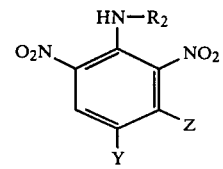

| Structure | | | Rate | Plant Species | | | | | | | | | | | | | | | |
|---|---|---|---|---|---|---|---|---|---|---|---|---|---|---|---|---|---|---|---|
| R₂ | Z | Y | lb/Acre | SE | MU | PI | RG | MG | TW | VL | BA | CR | GF | WO | CN | CO | SY | SB | RI |
| *CH(C₂H₅)₂ | CH₂OCH₃ | CH₃ | 1.0 | 7.6 | 7.5 | 8.7 | 3.6 | 4.3 | 8.5 | 8.3 | 9 | 9 | 9 | 2.4 | 3.0 | .60 | .9 | | |
| | | | 0.50 | 5.3 | 8.5 | 8.5 | 0 | 2.5 | 8.3 | 7.5 | 9 | 9 | 9 | 0.9 | 1.3 | 0 | 0 | | |
| | | | 0.25 | 2.4 | 7.6 | 8.1 | 0 | 0.7 | 7.6 | 5.9 | 8.8 | 9 | 9 | 0.7 | 0 | 0 | 0 | | |
| | | | 0.13 | 1.0 | 5.4 | 5.8 | 0 | 0 | 6.8 | 3.2 | 8.7 | 8.9 | 9 | 0 | 0 | 0 | 0 | | |
| | | | 0.06 | 0 | 2.1 | 3.8 | 0 | 0 | 3.9 | 1.1 | 6.5 | 8.9 | 8.5 | 0 | 0 | 0 | 0 | | |
| | | | 0.03 | 0 | 0 | 1.1 | 0 | 0 | 0.8 | 0 | 4.6 | 8.2 | 6.1 | 0 | 0 | 0 | 0 | | |
| **C₄H₉-sec | CH₂OCH₃ | CH₃ | 1.0 | 6.0 | 7.3 | 8.3 | 2 | 1 | 8 | 7.7 | 9 | 9 | 9 | 1 | 1 | 0 | 0.7 | | |
| | | | 0.50 | 3.5 | 5.3 | 7 | 0 | 0.7 | 7.7 | 5.7 | 9 | 9 | 9 | 0 | 1.7 | 0 | 0 | | |
| | | | 0.25 | 0 | 3 | 4.5 | 0 | 0 | 6 | 2 | 8.3 | 9 | 9 | 0 | 0 | 0 | 0 | | |
| | | | 0.13 | 0 | 0 | 1 | 0 | 0 | 2.3 | 0.7 | 8 | 9 | 9 | 0 | 0 | 0 | 0 | | |
| | | | 0.06 | 0 | 0 | 0 | 0 | 0 | 1 | 0 | 7 | 9 | 7.7 | 0 | 0 | 0 | 0 | | |
| | | | 0.03 | 0 | 0 | 0 | 0 | 0 | 0 | 0 | 6.7 | 8.3 | 6.7 | 0 | 0 | 0 | 0 | | |
| CH(C₂H₅)₂ | CH₂OCH₃ | C₃H₇-i | 1.0 | 7.7 | 8 | 8.3 | 6 | 7.7 | 8.3 | 8 | 9 | 9 | 9 | 5 | 2.7 | 0 | 0 | | 6 |
| | | | 0.50 | 7.7 | 8 | 8 | 4.7 | 4.3 | 8.3 | 8 | 9 | 9 | 9 | 3 | 2.3 | 0 | 0 | | 3 |
| | | | 0.25 | 6.7 | 8 | 8 | 2.7 | 6 | 8 | 6.3 | 9 | 9 | 9 | 1 | 1.7 | 0 | 0 | | 0 |
| | | | 0.13 | 5.3 | 8 | 7.6 | 0.7 | 2 | 7.3 | 3 | 8.7 | 9 | 9 | 0.3 | 1.7 | 0 | 0 | | 0 |
| | | | 0.06 | 0 | 3.5 | 7 | 0 | 0.3 | 6 | 1.7 | 7.6 | 9 | 9 | 0.3 | 0 | 0 | 0 | | 0 |
| | | | 0.03 | 1 | 1 | 1.7 | 0 | 0.3 | 1.3 | 0 | 3.8 | 8.7 | 8.3 | 0.3 | 0 | 0 | 0 | | 0 |
| ++C₃H₇-n | CH₂OCH₃ | C₃H₇-i | 1.0 | 7 | 6 | 7 | 0 | 0 | 7 | 1 | 9 | 9 | 9 | 2 | 0 | 0 | 0 | | |
| | | | 0.50 | 6 | 1 | 6 | 0 | 0 | 5 | 1 | 9 | 9 | 9 | 1 | 0 | 0 | 0 | | |
| | | | 0.25 | 1 | 0 | 2 | 0 | 0 | 1 | 0 | 7 | 9 | 7 | 0 | 0 | 0 | | | |
| | | | 0.13 | 0 | 0 | 0 | 0 | 0 | 0 | 0 | 3 | 7 | 6 | 0 | 0 | 0 | | | |
| | | | 0.60 | 0 | 0 | 0 | 0 | 0 | 0 | 0 | 1 | 6 | 5 | 0 | 0 | 0 | 0 | | |
| | | | 0.03 | 0 | 0 | 0 | 0 | 0 | 0 | 0 | 0 | 3 | 3 | 0 | 0 | 0 | 0 | | |
| C₃H₇-i | CH₂OCH₃ | CH₃ | 1.0 | 3.5 | 1.5 | 6.5 | 1.5 | 0 | 7 | 2.5 | 9 | 9 | 9 | 0 | 0 | 0 | 0 | | |
| | | | 0.50 | 1 | 1 | 4 | 0 | 0 | 3.5 | 1.5 | 9 | 9 | 9 | 0 | 0 | 0 | 0 | | |
| | | | 0.25 | 0 | 0 | 2.5 | 0 | 0 | 1.5 | 0 | 9 | 9 | 9 | 0 | 0 | 0 | 0 | | |
| | | | 0.13 | 0 | 0 | 0 | 0 | 0 | 0.5 | 0 | 4.5 | 7.5 | 7.5 | 0 | 0 | 0 | 0 | | |
| | | | 0.06 | 0 | 0 | 0 | 0 | 0 | 0 | 0 | 0.5 | 6.5 | 6.5 | 0 | 0 | 0 | 0 | | |
| | | | 0.03 | 0 | 0 | 0 | 0 | 0 | 0 | 0 | 0 | 0.5 | 1.5 | 0 | 0 | 0 | 0 | | |
| ++C₃H₇-n | CH₂OCH₃ | C₂H₅ | 1.0 | 0 | 9 | 9 | 0 | 0 | 7 | 2 | 8 | 9 | 9 | 1 | 0 | 0 | 0 | | |
| | | | 0.50 | 0 | 5 | 0 | 0 | 0 | 2 | 0 | 6 | 9 | 9 | 0 | 0 | 0 | 0 | | |
| | | | 0.25 | 0 | 0 | 0 | 0 | 0 | 0 | 0 | 7 | 8 | 7 | 0 | 0 | 0 | 0 | | |
| | | | 0.13 | 0 | 0 | 0 | 0 | 0 | 0 | 0 | 5 | 6 | 7 | 0 | 0 | 0 | 0 | | |
| | | | 0.06 | 0 | 0 | 0 | 0 | 0 | 0 | 0 | 0 | 5 | 5 | 0 | 0 | 0 | 0 | | |
| | | | 0.03 | 0 | 0 | 0 | 0 | 0 | 0 | 0 | 0 | 0 | 0 | 0 | 0 | 0 | 0 | | |
| ***CH(C₂H₅)₂ | CH₂OCH₃ | Cl | 1.0 | 2.5 | 9 | 8.5 | 1.5 | 3 | 8 | 8 | 9 | 9 | 9 | 2 | 0 | 0 | 0 | | |
| | | | 0.50 | 0 | 7.5 | 6.5 | 0 | 1 | 7.5 | 5 | 9 | 9 | 9 | 1.5 | 0 | 0 | 0 | | |
| | | | 0.25 | 0 | +9 | 6.5 | 0 | 0.5 | 4.5 | 2 | 8.5 | 9 | 8 | 0.5 | 0 | 0 | 0 | | |
| | | | 0.13 | 0 | +5 | 4 | 0 | 0 | 1.5 | 0.5 | 2 | 9 | 7.5 | 0 | 0 | 0 | 0 | | |
| | | | 0.06 | 0 | 0 | 0 | 0 | 0 | 1 | 0 | 2 | 8.5 | 2 | 0 | 0 | 0 | 0 | | |
| | | | 0.03 | 0 | 0 | 0 | 0 | 0 | 0 | 0 | 1 | 6.5 | 2 | 0 | 0 | | 0 | | |
| CH(CH₃)C₃H₇-n | CH₂OCH₃ | Cl | 1.0 | 0 | 9 | 8 | 0 | 0 | 5 | 0 | 7 | 9 | 9 | 0 | 0 | 0 | | | |
| | | | 0.50 | 0 | 7 | 5 | 0 | 0 | 0 | 0 | 7 | 9 | 9 | 0 | 0 | 0 | | | |
| | | | 0.25 | 0 | 8 | 0 | 0 | 0 | 0 | 0 | 7 | 8 | 9 | 0 | 0 | 0 | 0 | | |
| | | | 0.13 | 0 | 0 | 0 | 0 | 0 | 0 | 0 | 0 | 7 | 7 | 0 | 0 | 0 | 0 | | |
| | | | 0.06 | 0 | 0 | 0 | 0 | 0 | 0 | 0 | 0 | 6 | 0 | 0 | 0 | 0 | 0 | | |
| | | | 0.03 | 0 | 0 | 0 | 0 | 0 | 0 | 0 | 0 | 0 | 0 | 0 | 0 | 0 | 0 | | |
| CH(C₂H₅)₂ | CH₂OCH₃ | C₂H₅ | 1.0 | 8 | 8.3 | 8.3 | 5 | 6 | 8.3 | 8 | 9 | 9 | 9 | 5 | 4 | 4.7 | 0 | | 5 |
| | | | 0.50 | 4.7 | 8.3 | 8 | 2.3 | 4 | 8 | 8 | 9 | 9 | 9 | 1.3 | 1.7 | 0 | 0 | | 5 |
| | | | 0.25 | 2 | 8 | 8 | 1 | 1.7 | 8 | 5.3 | 9 | 9 | 9 | 1.5 | 1 | 0 | 0 | | 2 |
| | | | 0.13 | 2 | 4.3 | 5.3 | 0 | 0.3 | 8 | 2.7 | 8.7 | 9 | 9 | 1 | 0 | 0 | 0 | | 0 |
| | | | 0.06 | 2.5 | 3 | 2 | 0 | 0 | 7 | 1 | 8 | 9 | 9 | 0.5 | 0 | 0 | 0 | | 0 |
| | | | 0.03 | 0 | 0 | 1.7 | 0 | 0 | 3.3 | 0 | 5 | 8.3 | 7 | 0.5 | 0 | 0 | 0 | | 0 |
| C₃H₇-i | CH₂OCH₃ | C₂H₅ | 1.0 | 2 | 9 | 9 | 0 | 0 | 8 | 7 | 9 | 9 | 9 | 0 | 0 | 0 | 0 | | |
| | | | 0.50 | 0 | 0 | 7 | 0 | 0 | 8 | 6 | 9 | 9 | 9 | 0 | 0 | 0 | 0 | | |
| | | | 0.25 | 0 | 0 | 3 | 0 | 0 | 7 | 3 | 9 | 9 | 9 | 0 | 0 | 0 | 0 | | |
| | | | 0.13 | 0 | | 0 | 0 | 0 | 2 | 0 | 3 | 9 | 9 | 0 | 0 | 0 | 0 | | |
| | | | 0.06 | 0 | 0 | 0 | 0 | 0 | 0 | 0 | 3 | 9 | 9 | 0 | 0 | 0 | 0 | | |
| | | | 0.03 | 0 | | 0 | 0 | 0 | 0 | 0 | 0 | 9 | 7 | 0 | 0 | 0 | 0 | | |
| CH(CH₃)C₃H₇-n | CH₂OCH₃ | C₂H₅ | 1.0 | 6 | 9 | 9 | 3 | 0 | 8 | 7 | 9 | 9 | 9 | 2 | 0 | 0 | 0 | | |
| | | | 0.25 | 0 | 9 | 7 | 0 | 0 | 6 | 2 | 9 | 9 | 9 | 0 | 0 | | 0 | | |
| | | | 0.13 | 0 | 9 | 6 | 0 | 0 | 3 | 2 | 3 | 9 | 9 | 0 | 0 | 0 | 0 | | |
| | | | 0.06 | 0 | 0 | 2 | 0 | 0 | 2 | 0 | 1 | 9 | 9 | 0 | 0 | 0 | 0 | | |
| | | | 0.03 | 0 | 0 | 1 | 0 | 0 | 0 | 0 | 0 | 8 | 6 | 0 | 0 | 0 | 0 | | |
| CH(C₂H₅)C₃H₇-n | CH₂OCH₃ | C₂H₅ | 1.0 | 8 | 9 | 9 | 7 | 3 | 8 | 9 | 9 | 9 | 9 | 1 | 0 | 0 | 0 | | |
| | | | 0.50 | 0 | 9 | 9 | 0 | 0 | 8 | 6 | 9 | 9 | 9 | 0 | 0 | 0 | 0 | | |
| | | | 0.25 | 0 | 7 | 9 | 0 | 0 | 7 | 5 | 7 | 9 | 9 | 0 | 0 | 0 | 0 | | |
| | | | 0.13 | 0 | 0 | 7 | 0 | 0 | 3 | 2 | 5 | 9 | 9 | 0 | 0 | 0 | 0 | | |

TABLE XI-continued

Preemergence Herbicidal Evaluation of

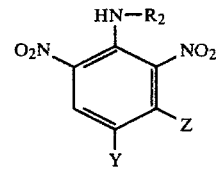

| Structure | | | Rate | Plant Species | | | | | | | | | | | | | | |
|---|---|---|---|---|---|---|---|---|---|---|---|---|---|---|---|---|---|---|
| R₂ | Z | Y | lb/Acre | SE | MU | PI | RG | MG | TW | VL | BA | CR | GF | WO | CN | CO | SY | SB | RI |
|  |  |  | 0.06 | 0 |  | 5 | 0 | 0 | 0 | 0 | 1 | 9 | 6 | 0 | 0 | 0 | 0 |  |  |
|  |  |  | 0.03 | 0 | 0 | 5 | 0 | 0 | 0 | 0 | 0 | 7 | 3 | 0 | 0 | 0 | 0 |  |  |
|  |  |  | 1.0 | 2 | 8 | 9 | 0 | 0 | 7 | 7 | 9 | 9 | 9 | 1 | 5 | 0 | 0 |  |  |
|  |  |  | 0.50 | 0 | 9 | 9 | 0 | 0 | 3 | 2 | 9 | 9 | 9 | 0 | 2 | 0 | 0 |  |  |
| CH(C₃H₇-n)₂ | CH₂OCH₃ | C₂H₅ | 0.25 | 0 | 3 | 9 | 0 | 0 | 2 | 0 | 9 | 9 | 9 | 0 | 2 | 0 | 0 |  |  |
|  |  |  | 0.13 | 0 | 0 | 5 | 0 | 0 | 0 | 0 | 2 | 9 | 8 | 0 | 0 | 0 | 0 |  |  |
|  |  |  | 0.06 | 0 | 0 | 3 | 0 | 0 | 0 | 0 | 0 | 7 | 0 | 0 | 0 | 0 | 0 |  |  |
|  |  |  | 0.03 | 0 | 0 | 0 | 0 | 0 | 0 | 0 | 0 | 5 | 0 | 0 | 0 | 0 | 0 |  |  |
|  |  |  | 1.0 | 0 | 9 | 6 | 0 | 0 | 3 | 3 | 9 | 9 | 9 | 0 | 2 | 0 | 0 |  |  |
|  |  |  | 0.50 | 0 | 0 | 6 | 0 | 0 | 0 | 0 | 8 | 9 | 8 | 0 | 2 | 0 | 0 |  |  |
| ++C₄H₉-i | CH₂OCH₃ | C₂H₅ | 0.25 | 0 |  | 3 | 0 | 0 | 0 | 0 | 3 | 9 | 6 | 0 | 0 | 0 | 0 |  |  |
|  |  |  | 0.13 | 0 | 0 | 0 | 0 | 0 | 0 | 0 | 0 | 7 | 0 | 0 | 0 | 0 | 0 |  |  |
|  |  |  | 0.06 | 0 | 0 | 0 | 0 | 0 | 0 | 0 | 0 | 3 | 0 | 0 | 0 | 0 | 0 |  |  |
|  |  |  | 0.03 | 0 | 0 | 0 | 0 | 0 | 0 | 0 | 0 | 0 | 0 | 0 | 0 | 0 | 0 |  |  |
|  |  |  | 1.0 | 5 | 9 | 9 | 2 | 0 | 8 | 7 | 9 | 9 | 9 | 2 | 5 | 2 | 3 |  |  |
|  |  |  | 0.50 | 0 | 7 | 9 | 0 | 0 | 8 | 3 | 9 | 9 | 9 | 0 | 3 | 0 | 0 |  |  |
| CH(CH₃)CH₂C₃H₇-i | CH₂OCH₃ | C₂H₅ | 0.25 | 0 | 7 | 8 | 0 | 0 | 3 | 1 | 9 | 9 | 9 | 0 | 0 | 0 | 0 |  |  |
|  |  |  | 0.13 | 0 | 0 | 7 | 0 | 0 | 0 | 0 | 9 | 9 | 9 | 0 | 0 | 0 | 0 |  |  |
|  |  |  | 0.06 | 0 | 0 | 5 | 0 | 0 | 0 | 0 | 5 | 9 | 9 | 0 | 0 | 0 | 0 |  |  |
|  |  |  | 0.03 | 0 | 0 | 0 | 0 | 0 | 0 | 0 | 0 | 9 | 3 | 0 | 0 | 0 | 0 |  |  |
|  |  |  | 1.0 | 8 | 9 | 9 | 0 | 8 | 8 | 8 | 9 | 9 | 9 | 2 | 2 | 2 | 2 |  |  |
|  |  |  | 0.50 | 7 | 9 | 8 | 0 | 8 | 8 | 7 | 9 | 9 | 9 | 0 | 2 | 0 | 0 |  |  |
| C₃H₇-i | CH₂OCH₃ | C₃H₇-i | 0.25 | 2 | 9 | 8 | 0 | 2 | 7 | 3 | 9 | 9 | 9 | 0 | 0 | 0 | 0 |  |  |
|  |  |  | 0.13 | 2 | 2 | 2 | 0 | 0 | 2 | 1 | 9 | 9 | 9 | 0 | 0 | 0 | 0 |  |  |
|  |  |  | 0.06 | 0 |  | 0 | 0 | 0 | 1 | 0 | 9 | 9 | 9 | 0 | 0 | 0 |  |  |  |
|  |  |  | 0.03 | 0 | 0 | 0 | 0 | 0 | 0 | 0 | 2 | 9 | 9 | 0 | 0 | 0 | 0 |  |  |
|  |  |  | 1.0 | 0 |  | 5 | 0 | 0 | 5 | 1 | 9 | 9 | 9 | 0 | 0 | 0 | 0 |  |  |
|  |  |  | 0.50 | 0 |  | 0 | 0 | 0 | 5 | 0 | 8 | 9 | 9 | 0 | 0 | 0 | 0 |  |  |
| ++CH₂CH=CH₂ | CH₂OCH₃ | C₂H₅ | 0.25 | 0 | 0 | 0 | 0 | 0 | 0 | 0 | 2 | 9 | 9 | 0 | 0 | 0 | 0 |  |  |
|  |  |  | 0.13 | 0 | 0 | 0 | 0 | 0 | 0 | 0 | 0 | 7 | 5 | 0 | 0 | 0 | 0 |  |  |
|  |  |  | 0.06 | 0 | 0 | 0 | 0 | 0 | 0 | 0 | 0 | 2 | 0 | 0 | 0 | 0 | 0 |  |  |
|  |  |  | 0.03 | 0 | 0 | 0 | 0 | 0 | 0 | 0 | 0 | 0 | 0 | 0 | 0 | 0 | 0 |  |  |
|  |  |  | 1.0 | 0 | 0 | 8 | 0 | 0 | 5 | 2 | 9 | 9 | 9 | 0 | 0 | 0 | 2 |  |  |
|  |  |  | 0.50 | 0 | 0 | 3 | 0 | 0 | 0 | 0 | 9 | 9 | 9 | 0 | 0 | 0 | 0 |  |  |
| CH(C₃H₇-n)₂ | CH₂OCH₃ | CH₃ | 0.25 | 0 | 0 | 0 | 0 | 0 | 0 | 0 | 3 | 9 | 5 | 0 | 0 | 0 | 0 |  |  |
|  |  |  | 0.13 | 0 | 0 | 0 | 0 | 0 | 0 | 0 | 3 | 6 | 1 | 0 | 0 | 0 | 0 |  |  |
|  |  |  | 0.06 | 0 | 0 | 0 | 0 | 0 | 0 | 0 | 0 | 3 | 0 | 0 | 0 | 0 | 0 |  |  |
|  |  |  | 0.03 | 0 | 0 | 0 | 0 | 0 | 0 | 0 | 0 | 0 | 0 | 0 | 0 | 0 | 0 |  |  |
|  |  |  | 1.0 | 0 | 9 | 7 | 0 | 0 | 0 | 0 | 8 | 9 | 9 | 1 | 0 | 0 | 0 |  |  |
| CH(CH₃)C₄H₉-n | CH₂OCH₃ | CH₃ | 0.50 | 0 | 9 | 6 | 0 | 0 | 0 | 0 | 6 | 8 | 6 | 0 | 0 | 0 | 0 |  |  |
|  |  |  | 0.25 | 0 | 9 | 0 | 0 | 0 | 0 | 0 | 0 | 6 | 3 | 0 | 0 | 0 | 0 |  |  |
|  |  |  | 0.13 | 0 | 0 | 0 | 0 | 0 | 0 | 0 | 0 | 0 | 0 | 0 | 0 | 0 | 0 |  |  |
|  |  |  | 1.0 | 7 | 7 | 9 | 5 | 7 | 7 | 7 | 9 | 9 | 9 | 3 | 6 | 0 | 0 |  |  |
|  |  |  | 0.5 | 7 | 7 | 7 | 3 | 5 | 7 | 6 | 9 | 9 | 9 | 2 | 1 | 0 | 0 |  |  |
| C₄H₉-sec | CH₂OCH₃ | C₂H₅ | 0.25 | 5 |  | 7 | 0 | 1 | 7 | 3 | 9 | 9 | 9 | 1 | 0 | 0 | 0 |  |  |
|  |  |  | 0.13 | 3 | 0 | 6 | 0 | 0 | 7 | 3 | 9 | 9 | 9 | 1 | 0 |  | 0 |  |  |
|  |  |  | 0.06 | 0 | 0 | 3 | 0 | 0 | 5 | 0 | 7 | 8 | 8 | 0 | 0 | 0 | 0 |  |  |
|  |  |  | 0.03 | 0 |  | 2 | 0 | 0 | 3 | 0 | 6 | 8 | 8 | 0 | 0 | 0 | 0 |  |  |
|  |  |  | 1.0 | 0 | 9 | 9 | 0 | 0 | 8 | 8 | 9 | 9 | 9 | 1 | 0 | 0 | 0 |  |  |
|  |  |  | 0.50 | 0 | 6 | 6 | 0 | 0 | 7 | 6 | 9 | 9 | 9 | 0 | 0 | 0 | 0 |  |  |
| CH(CH₃)C₃H₇-n | CH₂OCH₃ | CH₃ | 0.25 | 0 | 6 | 6 | 0 | 0 | 6 | 1 | 7 | 9 | 9 | 0 | 0 | 0 | 0 |  |  |
|  |  |  | 0.13 | 0 | 0 | 2 | 0 | 0 | 3 | 0 | 2 | 9 | 5 | 0 | 0 | 0 | 0 |  |  |
|  |  |  | 0.06 | 0 |  | 0 | 0 | 0 | 0 | 0 | 2 | 9 | 3 | 0 | 0 | 0 | 0 |  |  |
|  |  |  | 0.03 | 0 |  | 0 | 0 | 0 | 0 | 0 | 0 | 6 | 0 | 0 | 0 | 0 | 0 |  |  |
|  |  |  | 1.0 | 0 | 8 | 9 | 0 | 3 | 8 | 5 | 9 | 9 | 9 | 1 | 0 | 0 | 0 |  |  |
|  |  |  | 0.50 | 0 | 8 | 8 | 0 | 0 | .6 | 3 | 9 | 9 | 9 | 0 | 0 | 0 | 0 |  |  |
| CH(C₂H₅)C₃H₇-n | CH₂OCH₃ | CH₃ | 0.25 | 0 | 9 | 7 | 0 | 0 | 2 | 2 | 9 | 9 | 9 | 0 | 0 | 0 | 0 |  |  |
|  |  |  | 0.13 | 0 | 0 | 0 | 0 | 0 | 0 | 0 | 8 | 9 | 9 | 0 | 0 | 0 | 0 |  |  |
|  |  |  | 0.06 | 0 | 0 | 0 | 0 | 0 | 0 | 0 | 0 | 7 | 5 | 0 | 0 | 0 | 0 |  |  |
|  |  |  | 0.03 | 0 | 0 | 0 | 0 | 0 | 0 | 0 | 0 | 3 | 0 | 0 | 0 | 0 | 0 |  |  |
|  |  |  | 1.0 | 0 | 8 | 7 | 0 | 0 | 2 | 2 | 9 | 9 | 9 | 0 | 1 | 0 | 0 |  |  |
|  |  |  | 0.50 | 0 | 9 | 6 | 0 | 0 | 0 | 0 | 9 | 9 | 9 | 0 | 0 | 0 | 0 |  |  |
| CH(CH₃)C₃H₇-i | CH₂OCH₃ | CH₃ | 0.25 | 0 | 0 | 2 | 0 | 0 | 0 | 0 | 8 | 9 | 9 | 0 | 0 | 0 | 0 |  |  |
|  |  |  | 0.13 | 0 |  | 0 | 0 | 0 | 0 | 0 | 6 | 8 | 5 | 0 | 0 | 0 | 0 |  |  |
|  |  |  | 0.06 | 0 |  | 0 | 0 | 0 | 0 | 0 | 2 | 5 | 0 | 0 | 0 | 0 | 0 |  |  |
|  |  |  | 0.03 | 0 | 0 | 0 | 0 | 0 | 0 | 0 | 0 | 0 | 0 | 0 | 0 | 0 | 0 |  |  |
|  |  |  | 1.0 | 2 | 9 | 8 | 6 | 0 | 8 | 0 | 9 | 9 | 9 |  | 0 | 0 | 0 | 0 |  |
|  |  |  | 0.50 | 0 | 9 | 6 | 0 | 0 | 2 | 0 | 9 | 9 | 9 |  | 0 | 0 | 0 | 0 |  |
| *** C₄H₉-sec | CH₂OCH₃ | Cl | 0.25 | 0 | 0 | 3 | 0 | 0 | 0 | 0 | 9 | 9 | 9 |  | 0 | 0 | 0 | 0 |  |

TABLE XI-continued

Preemergence Herbicidal Evaluation of

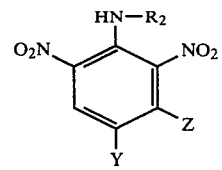

| Structure | | | Rate | Plant Species | | | | | | | | | | | | | | | |
|---|---|---|---|---|---|---|---|---|---|---|---|---|---|---|---|---|---|---|---|
| R$_2$ | Z | Y | lb/Acre | SE | MU | PI | RG | MG | TW | VL | BA | CR | GF | WO | CN | CO | SY | SB | RI |
| | | | 0.13 | 0 | — | 0 | 0 | 0 | 0 | 0 | 5 | 9 | 9 | | 0 | 0 | 0 | | 0 |
| | | | 0.06 | 0 | 0 | 0 | 0 | 0 | 0 | 0 | 2 | 7 | 2 | | 0 | 0 | 0 | | 0 |
| | | | 0.03 | 0 | 0 | 0 | 0 | 0 | 0 | 0 | 0 | 2 | 0 | | 0 | 0 | 0 | | 0 |
| | | | 1.0 | 0 | 8 | 9 | 0 | 0 | 8 | 2 | 9 | 9 | 9 | | 3 | 0 | 0 | | 0 |
| CH(CH$_3$)CH$_2$Cl | CH$_2$OCH$_3$ | C$_2$H$_5$ | 0.05 | 0 | 9 | 8 | 0 | 0 | 7 | 1 | 9 | 9 | 9 | | 1 | 0 | 0 | | 0 |
| | | | 0.25 | | | 7 | 0 | 0 | 2 | 0 | 9 | 9 | 9 | | 0 | | 0 | | 0 |
| | | | 0.13 | 0 | | 0 | 0 | 0 | 0 | 0 | 9 | 9 | 9 | | 0 | | 0 | | 0 |
| | | | 0.06 | 0 | 0 | 0 | 0 | 0 | 0 | 0 | 2 | 8 | 9 | | 0 | 0 | 0 | | 0 |
| | | | 0.03 | 0 | 0 | 0 | 0 | 0 | 0 | 0 | 0 | 5 | 1 | | 0 | 0 | 0 | | 0 |
| | | | 1.0 | 0 | 9 | 7 | 0 | 0 | 7 | 2 | 9 | 9 | 9 | | 1 | 0 | 0 | | 0 |
| | | | 0.50 | 0 | 9 | 8 | 0 | 0 | 2 | 0 | 9 | 9 | 9 | | 0 | 0 | 0 | | 0 |
| CH(C$_2$H$_5$)CH$_2$Cl | CH$_2$OCH$_3$ | CH$_3$ | 0.25 | 0 | 2 | 2 | 0 | 0 | 0 | 0 | 8 | 9 | 9 | | 0 | 0 | 0 | | 0 |
| | | | 0.13 | 0 | | 0 | 0 | 0 | 0 | 0 | 5 | 9 | 8 | | 0 | | 0 | | 0 |
| | | | 0.06 | 0 | | 0 | 0 | 0 | 0 | 0 | 2 | 7 | 2 | | 0 | 0 | 0 | | 0 |
| | | | 0.03 | 0 | | 0 | 0 | 0 | 0 | 0 | 0 | 3 | 0 | | 0 | 0 | 0 | | 0 |
| | | | 1.0 | 0 | 8 | 8 | 0 | 0 | 2 | 2 | 2 | 9 | 9 | | 2 | 0 | 0 | | 2 |
| | | | 0.50 | 0 | 0 | 0 | 0 | 0 | 0 | 0 | 0 | 9 | 9 | | 0 | | 0 | | |
| ++C$_3$H$_7$-n | CH$_2$OCH$_3$ | CH$_3$ | 0.25 | 0 | | 0 | 0 | 0 | 0 | 0 | 0 | 8 | 2 | | 0 | 0 | 0 | | 0 |
| | | | 0.13 | 0 | 0 | 0 | 0 | 0 | 0 | 0 | 0 | 3 | 0 | | 0 | 0 | 0 | | 0 |
| | | | 0.06 | 0 | 0 | 0 | 0 | 0 | 0 | 0 | 0 | 0 | 0 | | 0 | 0 | 0 | | 0 |
| | | | 1.0 | 0 | 9 | 7 | 0 | 0 | 3 | 0 | 8 | 9 | 9 | | 0 | 0 | 0 | | 0 |
| | | | 0.50 | 0 | 7 | 2 | 0 | 0 | 0 | 0 | 7 | 9 | 9 | | 0 | | 0 | | 0 |
| ++C$_4$H$_9$-n | CH$_2$OCH$_3$ | C$_3$H$_7$-i | 0.25 | 0 | | 0 | 0 | 0 | 0 | 0 | 3 | 6 | 9 | | 0 | 0 | 0 | | 0 |
| | | | 0.13 | 0 | 0 | 0 | 0 | 0 | 0 | 0 | 1 | | 6 | | 0 | 0 | 0 | | 0 |
| | | | 0.06 | 0 | 0 | 0 | 0 | 0 | 0 | 0 | 0 | 2 | 2 | | 0 | 0 | 0 | | 0 |
| | | | 0.03 | 0 | | 0 | 0 | 0 | 0 | 0 | 0 | 0 | 0 | 0 | | 0 | 0 | | 0 |
| | | | 1.0 | 7 | | 9 | 0 | 2 | 8 | 7 | 9 | 9 | 9 | 2 | 0 | 0 | 2 | | |
| | | | 0.50 | 2 | | 9 | 0 | 0 | 8 | 6 | 9 | 9 | 9 | 0 | 0 | 0 | 0 | | |
| CH(CH$_3$)C$_3$H$_7$-n | CH$_2$OCH$_3$ | C$_3$H$_7$-i | 0.25 | 0 | | 9 | 0 | 0 | 2 | 2 | 9 | 9 | 9 | 0 | 0 | 0 | 0 | | |
| | | | 0.13 | 0 | | 8 | 0 | 0 | 0 | 1 | 9 | 9 | 9 | 0 | 0 | 0 | 0 | | |
| | | | 0.06 | | | 5 | 0 | 0 | 0 | 1 | 7 | 9 | 9 | 0 | 0 | 0 | 0 | | |
| | | | 0.03 | 0 | | 0 | 0 | 0 | 0 | 0 | 2 | 9 | 7 | 0 | 0 | 0 | 0 | | |
| | | | 1.0 | 2 | 8 | 9 | 0 | 1 | 8 | 5 | 9 | 9 | 9 | | 0 | 0 | 0 | | 0 |
| | | | 0.50 | 0 | 0 | 8 | 0 | 0 | 7 | 2 | 9 | 9 | 9 | | 0 | 0 | 0 | | |
| CH(C$_2$H$_5$)CH$_2$Cl | CH$_2$OCH$_3$ | C$_2$H$_5$ | 0.25 | 0 | 0 | 6 | 0 | 0 | 7 | 0 | 9 | 9 | 9 | | 0 | 0 | 0 | | |
| | | | 0.13 | 0 | | 2 | 0 | 0 | 0 | 0 | 9 | 9 | 7 | | 0 | 0 | 0 | | 0 |
| | | | 0.06 | 0 | 0 | 0 | 0 | 0 | 0 | 0 | 8 | 9 | 6 | | 0 | 0 | 0 | | 0 |
| | | | 0.03 | 0 | | 0 | 0 | 0 | 0 | 0 | 2 | 9 | 3 | | 0 | 0 | 0 | | 0 |
| | | | 1.0 | 2 | 9 | 9 | 3 | 0 | 7 | 3 | 9 | 9 | 9 | | 0 | 0 | 0 | | 7 |
| | | | 0.50 | 0 | 9 | 7 | 0 | 0 | 3 | 0 | 8 | 9 | 9 | | 0 | 0 | 0 | | 3 |
| CH(C$_2$H$_5$)$_2$ | CH$_2$OCH$_3$ | C$_4$H$_9$-sec | 0.25 | 0 | 5 | 7 | 0 | 0 | 0 | 0 | 8 | 9 | 9 | | 0 | 0 | 0 | | 0 |
| | | | 0.13 | 0 | 0 | 3 | 0 | 0 | 0 | 0 | 7 | 9 | 9 | | 0 | 0 | 0 | | 0 |
| | | | 0.06 | 0 | | 0 | 0 | 0 | 0 | 0 | 0 | 8 | 8 | | 0 | 0 | 0 | | 0 |
| | | | 0.03 | 0 | | 0 | 0 | 0 | 0 | 0 | 0 | 8 | 5 | | 0 | 0 | 0 | | 0 |
| | | | 1.0 | 3 | 3 | 3 | 0 | 0 | 2 | 0 | 8 | 9 | 6 | | 0 | 0 | 0 | | 0 |
| ++C$_4$H$_9$-i | CH$_2$OCH$_3$ | CH$_3$ | 0.50 | 0 | 0 | 0 | 0 | 0 | 0 | 0 | 2 | 2 | 0 | | 0 | 0 | 0 | | 0 |
| | | | 0.25 | 0 | 0 | 0 | 0 | 0 | 0 | 0 | 0 | 0 | 0 | | 0 | 0 | 0 | | 0 |
| | | | 1.0 | 6 | 8 | 9 | 2 | 7 | 8 | 7 | 9 | 9 | 9 | | 0 | 0 | 0 | | 5 |
| | | | 0.50 | 0 | 9 | 9 | 0 | | 7 | 2 | 9 | 9 | 9 | | 0 | 0 | 0 | | 0 |
| CH(C$_2$H$_5$)CH$_2$Cl | CH$_2$OCH$_3$ | C$_3$H$_7$-i | 0.25 | 0 | 7 | 8 | 0 | 0 | 6 | 2 | 9 | 9 | 9 | | 0 | 0 | 0 | | 0 |
| | | | 0.13 | 0 | 0 | 7 | 0 | 0 | 0 | 0 | 9 | 9 | 9 | | 0 | 0 | 0 | | 0 |
| | | | 0.06 | 0 | | 0 | 0 | 0 | 0 | 0 | 8 | 9 | 8 | | 0 | 0 | 0 | | 0 |
| | | | 0.03 | 0 | 0 | | 0 | 0 | 0 | 0 | 0 | 9 | 0 | | 0 | 0 | 0 | | 0 |
| | | | 1.0 | 0 | | 3 | 0 | 0 | 7 | 2 | 9 | 9 | 9 | 0 | 0 | 0 | 0 | | |
| | | | 0.50 | 0 | | 0 | 0 | 0 | 3 | 0 | 9 | 9 | 9 | 0 | 0 | 0 | 0 | | |
| CH(CH$_3$)CHClCH$_3$ | CH$_2$OCH$_3$ | CH$_3$ | 0.25 | 0 | | 0 | 0 | 0 | 0 | 0 | 5 | 7 | 6 | 0 | 0 | 0 | 0 | | |
| | | | 0.13 | 0 | | 0 | 0 | 0 | 0 | 0 | 2 | 6 | 2 | 0 | 0 | 0 | 0 | | |
| | | | 0.06 | 0 | 0 | 0 | 0 | 0 | 0 | 0 | 0 | 2 | 0 | 0 | 0 | 0 | 0 | | |
| | | | 0.03 | 0 | 0 | 0 | 0 | 0 | 0 | 0 | 0 | 0 | 0 | 0 | 0 | 0 | 0 | | |
| | | | 1.0 | 0 | 8 | 9 | 0 | 0 | 8 | 0 | 9 | 9 | 9 | | 0 | 0 | 0 | | |
| | | | 0.50 | 0 | 8 | 8 | 0 | 0 | 2 | 0 | 8 | 9 | 9 | | 0 | 0 | 0 | | |
| CH(CH$_3$)CHClCH$_3$ | CH$_2$OCH$_3$ | C$_3$H$_7$-i | 0.25 | 0 | 0 | 6 | 0 | 0 | 0 | 0 | 3 | 9 | 9 | | 0 | 0 | 0 | | 0 |
| | | | 0.13 | 0 | | 0 | 0 | 0 | 0 | 0 | 0 | 9 | 7 | | 0 | 0 | 0 | | 0 |
| | | | 0.06 | 0 | 0 | 0 | 0 | 0 | 0 | 0 | 0 | 9 | 3 | | 0 | 0 | 0 | | 0 |
| | | | 0.03 | 0 | | 0 | 0 | 0 | 0 | 0 | 0 | 7 | 0 | | 0 | 0 | 0 | | 0 |
| | | | 1.0 | 0 | 9 | 8 | 0 | 0 | 2 | 0 | 8 | 9 | 9 | | 0 | 0 | 0 | | 0 |
| | | | 0.50 | 0 | 5 | 2 | 0 | 0 | 0 | 0 | 8 | 9 | 9 | | 0 | 0 | 0 | | 0 |
| CH(CH$_3$)C$_4$H$_9$-n | CH$_2$OCH$_3$ | C$_3$H$_7$-i | 0.25 | 0 | 0 | 0 | 0 | 0 | 0 | 0 | 2 | 9 | 9 | | 0 | 0 | | | 0 |
| | | | 0.13 | 0 | | 0 | 0 | 0 | 0 | 0 | 2 | 9 | 6 | | 0 | 0 | 0 | | 0 |

TABLE XI-continued
Preemergence Herbicidal Evaluation of

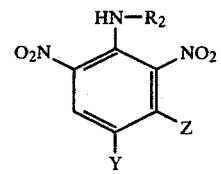

| Structure | | | Rate | Plant Species | | | | | | | | | | | | | | | |
|---|---|---|---|---|---|---|---|---|---|---|---|---|---|---|---|---|---|---|---|
| $R_2$ | Z | Y | lb/Acre | SE | MU | PI | RG | MG | TW | VL | BA | CR | GF | WO | CN | CO | SY | SB | RI |
| | | | 0.06 | 0 | 0 | 0 | 0 | 0 | 0 | 0 | 2 | 2 | 0 | | 0 | 0 | 0 | | 0 |
| | | | 0.03 | 0 | | 0 | 0 | 0 | 0 | 0 | 0 | 0 | 0 | | 0 | | 0 | | 0 |
| | | | 1.0 | 0 | 8 | 8 | 0 | 0 | 7 | 0 | 9 | 9 | 9 | | 0 | 0 | 0 | | 0 |
| | | | 0.50 | 0 | 0 | 5 | 0 | 0 | 2 | 0 | 8 | 9 | 9 | | 0 | 0 | 0 | | 0 |
| $CH(CH_3)CH_2C_3H_7$-i | $CH_2OCH_3$ | $CH_3$ | 0.25 | 0 | 0 | 0 | 0 | 0 | 0 | 0 | 8 | 9 | 9 | | 0 | 0 | 0 | | 0 |
| | | | 0.13 | 0 | | 0 | 0 | 0 | 0 | 0 | 8 | 7 | 3 | | 0 | 0 | 0 | | 0 |
| | | | 0.06 | 0 | | 0 | 0 | 0 | 0 | 0 | 3 | 6 | 2 | | 0 | 0 | 0 | | 0 |
| | | | 0.03 | 0 | 0 | 0 | 0 | 0 | 0 | 0 | 0 | 3 | 0 | | 0 | 0 | 0 | | 0 |
| | | | 1.0 | 0 | 9 | 9 | 0 | 0 | 8 | 2 | 9 | 9 | 9 | | 0 | 0 | 0 | | 3 |
| | | | 0.50 | | 9 | 7 | 0 | 0 | 6 | 0 | 9 | 9 | 9 | | 0 | 0 | 0 | | 3 |
| $CH(CH_3)CH_2CH_2Cl$ | $CH_2OCH_3$ | $C_2H_5$ | 0.25 | 0 | 9 | 0 | 0 | 0 | 0 | 0 | 9 | 9 | 9 | | 0 | 0 | 0 | | 0 |
| | | | 0.13 | 0 | 9 | 0 | 0 | 0 | 0 | 0 | 9 | 9 | 9 | | 0 | 0 | 0 | | 0 |
| | | | 0.06 | 0 | 8 | 0 | 0 | 0 | 0 | 0 | 9 | 9 | 6 | | 0 | 0 | 0 | | 0 |
| | | | 0.03 | 0 | 8 | 0 | 0 | 0 | 0 | 0 | 8 | 8 | 8 | | 0 | 0 | 0 | | 0 |
| | | | 1.0 | 2 | 9 | 8 | 8 | 2 | 8 | 8 | 9 | 9 | 9 | | 2 | 0 | 0 | | 0 |
| | | | 0.50 | 0 | 9 | 8 | 0 | 0 | 7 | 1 | 8 | 9 | 9 | | 0 | 0 | 0 | | 0 |
| $CH(C_2H_5)_2$ | $CH_2OCH_3$ | $C_3H_7$-n | 0.25 | 0 | 9 | 8 | 0 | | 2 | 0 | 8 | 9 | 9 | | 0 | 0 | 0 | | 0 |
| | | | 0.13 | 0 | | 0 | 0 | 0 | 0 | 0 | 8 | 9 | 9 | | 0 | 0 | 0 | | 0 |
| | | | 0.06 | 0 | | 0 | 0 | 0 | 0 | 0 | 5 | 8 | 7 | | 0 | 0 | 0 | | 0 |
| | | | 0.03 | 0 | | 0 | 0 | 0 | 0 | 0 | 0 | 5 | 5 | | 0 | 0 | 0 | | 0 |
| | | | 1.0 | 8 | | 9 | 9 | 3 | 9 | 8 | 9 | 9 | 9 | 4 | 0 | 0 | 0 | | |
| | | | 0.50 | 7 | | 9 | 3 | 2 | 9 | 8 | 9 | 9 | 9 | 1 | 0 | 0 | 0 | | |
| $C_4H_9$-sec | $CH_2OCH_3$ | $C_3H_7$-i | 0.25 | 3 | | 9 | 0 | 1 | 7 | 7 | 9 | 9 | 9 | 0 | 0 | 0 | 0 | | |
| | | | 0.13 | 0 | | 8 | 0 | 0 | 6 | 3 | 7 | 9 | 9 | 0 | 0 | 0 | 0 | | |
| | | | 0.06 | 0 | | 7 | 0 | 0 | 2 | 1 | 2 | 9 | 9 | 0 | 0 | 0 | 0 | | |
| | | | 0.03 | 0 | | | 0 | 0 | | 0 | 2 | 9 | 5 | 0 | 0 | 0 | 0 | | |
| | | | 1.0 | 8 | | 9 | 7 | 2 | 8 | 9 | 9 | 9 | 9 | 2 | 0 | 0 | 0 | | |
| | | | 0.50 | 7 | | 9 | 0 | 2 | 8 | 5 | 9 | 9 | 9 | 0 | 0 | 0 | 0 | | |
| $CH(C_2H_5)C_3H_7$-n | $CH_2OCH_3$ | $C_3H_7$-i | 0.25 | 2 | | 9 | 0 | 0 | 8 | 4 | 9 | 9 | 9 | 0 | 0 | 0 | 0 | | |
| | | | 0.13 | 0 | | 7 | 0 | 0 | 6 | 4 | 7 | 9 | 9 | 0 | 0 | 0 | 0 | | |
| | | | 0.06 | 0 | | 5 | 0 | 0 | 2 | 4 | 3 | 9 | 9 | 0 | 0 | 0 | 0 | | |
| | | | 0.03 | 0 | | 5 | 0 | 0 | 0 | 1 | 0 | 9 | 9 | 0 | 0 | 0 | 0 | | |
| | | | 1.0 | 0 | 9 | 0 | 0 | 0 | 0 | 0 | 9 | 9 | 9 | | 0 | 0 | 0 | | 0 |
| | | | 0.50 | 0 | 9 | 0 | 0 | 0 | 0 | 0 | 0 | 7 | 2 | | 0 | 0 | 0 | | 0 |
| ++$CH(C_2H_5)_2$ | $CH_2OCH_3$ | $C_4H_9$-n | 0.25 | 0 | 0 | 0 | 0 | 0 | 0 | 0 | 0 | 5 | 0 | | 0 | 0 | 0 | | 0 |
| | | | 0.13 | 0 | | 0 | 0 | 0 | 0 | 0 | 0 | 0 | 0 | | 0 | 0 | 0 | | 0 |
| | | | 1.0 | 1 | 0 | 4 | 1 | 0 | 6 | 2.5 | 7 | 9 | 9 | 0.5 | 0 | 0 | 1.5 | | |
| | | | 0.50 | 0.5 | 0.5 | 1 | 0 | 0 | 1.5 | 0.5 | 4 | 9 | 9 | 0 | 0 | 0 | 0 | | |
| ++$CH(C_2H_5)_2$ | $CH_2OC_2H_5$ | $CH_3$ | 0.25 | 0 | 0.5 | 1 | 0 | 0 | 1 | 0 | 2 | 8 | 7.5 | 0 | 0 | 0 | 0 | | |
| | | | 0.13 | 0 | 0 | 0 | 0 | 0 | 0 | 0 | 3.5 | 7 | 6.5 | 0 | 0 | 0 | 0 | | |
| | | | 0.06 | 0 | 0 | 0 | 0 | 0 | 0 | 0 | 0 | 4 | 5 | 0 | 0 | 0 | 0 | | |
| | | | 0.03 | 0 | 0 | 0 | 0 | 0 | 0 | 0 | 0 | 0 | 0 | 0 | 0 | 0 | 0 | | |
| | | | 1.0 | 0 | 8 | 8 | 0 | 0 | 2 | 0 | 9 | 9 | 9 | | 0 | 0 | 0 | | 3 |
| | | | 0.50 | 0 | 8 | 7 | 0 | 0 | 0 | 0 | 9 | 9 | 9 | | 0 | 0 | 0 | | 0 |
| ++$C_4H_9$-i | $CH_2OCH_3$ | $C_3H_7$-i | 0.25 | 0 | 0 | 2 | 0 | 0 | 0 | 0 | 8 | 9 | 8 | | 0 | 0 | 0 | | 0 |
| | | | 0.13 | 0 | 0 | 0 | 0 | 0 | 0 | 0 | 3 | 8 | 5 | | 0 | 0 | 0 | | 0 |
| | | | 0.06 | 0 | | 0 | 0 | 0 | 0 | 0 | 0 | 7 | 2 | | 0 | 0 | 0 | | 0 |
| | | | 0.03 | 0 | | 0 | 0 | 0 | 0 | 0 | 0 | 0 | 0 | | 0 | 0 | 0 | | 0 |
| | | | 1.0 | 2 | 9 | 8 | 0 | 0 | 7 | 0 | 9 | 9 | 9 | | 2 | 0 | 0 | | 0 |
| | | | 0.50 | 2 | 9 | 7 | 0 | 0 | 7 | 0 | 9 | 9 | 9 | | 2 | 0 | 0 | | 0 |
| $C_3H_7$-i | $CH_2OCH_3$ | $C_4H_9$-sec | 0.25 | 0 | 7 | 3 | 0 | 0 | 0 | 0 | 9 | 9 | 8 | | 0 | 0 | 0 | | 0 |
| | | | 0.13 | 0 | 0 | 2 | 0 | 0 | 0 | 0 | 9 | 8 | 7 | | 0 | 0 | 0 | | 0 |
| | | | 0.06 | 0 | 0 | 2 | 0 | 0 | 0 | 0 | 6 | 8 | 6 | | 0 | 0 | 0 | | 0 |
| | | | 0.03 | 0 | 0 | 0 | 0 | 0 | 0 | 0 | 3 | 7 | 2 | | 0 | 0 | 0 | | 0 |
| | | | 1.0 | 2 | 6 | 8 | 0 | 0 | 6 | 5 | 9 | 9 | 9 | | 3 | 0 | 0 | | 0 |
| | | | 0.50 | 0 | | 9 | 0 | 0 | 2 | 0 | 9 | 9 | 9 | | 0 | | 0 | | 0 |
| $CH(CH_3)CH_2Cl$ | $CH_2OCH_3$ | $CH_3$ | 0.25 | 0 | 0 | 3 | 0 | 0 | 0 | 0 | 9 | 9 | 9 | | 0 | 0 | 0 | | 0 |
| | | | 0.13 | 0 | 0 | 0 | 0 | 0 | 0 | 0 | 7 | 8 | 7 | | 0 | 0 | 0 | | 0 |
| | | | 0.06 | 0 | 0 | 0 | 0 | 0 | 0 | 0 | 6 | 6 | 6 | | 0 | 0 | 0 | | 0 |
| | | | 0.03 | 0 | | 0 | 0 | 0 | 0 | 0 | 6 | 3 | 0 | | 0 | 0 | 0 | | 0 |
| $CH(C_2H_5)_2$ | $CH_2OCH_3$ | $C_4H_9$-i | 1.0 | 2 | 9 | 6 | 0 | 0 | 7 | 6 | 9 | 9 | 9 | | 0 | 0 | 3 | | 0 |
| | | | 0.5 | 0 | 9 | 2 | 0 | 0 | 2 | 3 | 8 | 9 | 9 | | 0 | 0 | 0 | | |
| | | | 0.25 | 0 | | 0 | 0 | 0 | 0 | 2 | 8 | 9 | 8 | | 0 | 0 | 0 | | 0 |
| | | | 0.13 | 0 | 0 | 0 | 0 | 0 | 0 | 0 | 7 | 7 | 6 | | 0 | | 0 | | 0 |
| | | | 0.06 | 0 | 0 | 0 | 0 | 0 | 0 | 0 | 2 | 2 | 0 | | 0 | 0 | 0 | | 0 |
| | | | 0.03 | 0 | | 0 | 0 | 0 | 0 | 0 | 0 | 0 | 0 | | 0 | | 0 | | 0 |
| $CH(C_2H_5)_2$ | —CHOCH$_3$<br>\|<br>CH$_3$ | $CH_3$ | 1.0 | 6 | 5 | 8 | 0 | 2 | 8 | 6 | 9 | 9 | 9 | | 0 | | 0 | | 2 |

TABLE XI-continued

Preemergence Herbicidal Evaluation of

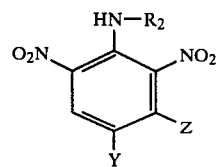

| Structure | | | Rate | Plant Species | | | | | | | | | | | | | | | |
|---|---|---|---|---|---|---|---|---|---|---|---|---|---|---|---|---|---|---|---|
| R₂ | Z | Y | lb/Acre | SE | MU | PI | RG | MG | TW | VL | BA | CR | GF | WO | CN | CO | SY | SB | RI |
| | | | 0.5 | 0 | | 6 | 0 | 0 | 7 | 5 | 9 | 9 | 9 | | 0 | 0 | 0 | | 2 |
| | | | 0.25 | 0 | | 5 | 0 | 0 | | 2 | 9 | 9 | 9 | | 0 | 0 | 0 | | 1 |
| | | | 0.13 | | | 2 | 0 | 0 | 1 | 0 | 8 | 9 | 8 | | 0 | | 0 | | 0 |
| | | | 0.06 | 0 | | 0 | 0 | 0 | 0 | 0 | 5 | 8 | 3 | | 0 | | 0 | | 0 |
| | | | 0.03 | 0 | | 0 | 0 | 0 | 0 | 0 | 3 | 3 | 0 | | 0 | | 0 | | 0 |
| —CH(CH₃)C₂H₅ | CH₂OCH₃ | C₃H₇-n | 1.0 | 2 | 8 | 8 | 0 | 0 | 8 | 5 | 9 | 9 | 9 | | 7 | 0 | 0 | | 0 |
| | | | 0.5 | 0 | 8 | 3 | 0 | 0 | 2 | 1 | 9 | 9 | 9 | | 0 | 0 | 0 | | 0 |
| | | | 0.25 | 0 | 9 | 7 | 0 | 0 | 0 | 0 | 9 | 9 | 9 | | 0 | 0 | 0 | | 0 |
| | | | 0.13 | 0 | | 0 | 0 | 0 | 0 | 0 | 9 | 9 | 9 | | 0 | 0 | 0 | | 0 |
| | | | 0.06 | 0 | | 0 | 0 | 0 | 0 | 0 | 7 | 7 | 9 | | 0 | 0 | 0 | | 0 |
| | | | 0.03 | 0 | 0 | 0 | 0 | 0 | 0 | 0 | 8 | 6 | 6 | | 0 | 0 | 0 | | 0 |
| —CH(CH₃)₂ | CH₂OCH₃ | C₃H₇-n | 1.0 | 0 | 0 | 7 | 0 | 0 | 8 | 2 | 9 | 9 | 9 | | 2 | 0 | | | 0 |
| | | | 0.5 | 0 | 0 | 6 | 0 | 0 | 7 | 0 | 9 | 9 | 9 | | 0 | 0 | 0 | | 0 |
| | | | 0.25 | 0 | 0 | | 0 | 0 | 2 | 0 | 9 | 9 | 9 | | 0 | 0 | 0 | | 0 |
| | | | 0.13 | 0 | | 0 | 0 | 0 | 0 | 0 | 8 | 8 | 8 | | 0 | | | | 0 |
| | | | 0.06 | 0 | | 0 | 0 | 0 | 0 | 0 | 8 | 8 | 7 | | 0 | 0 | 0 | | 0 |
| | | | 0.03 | 0 | | 0 | 0 | 0 | 0 | 0 | 5 | 3 | 3 | | 0 | 0 | 0 | | 0 |
| ++C₃H₇-i | CH₂OCH₃ | C₄H₉-n | 1.0 | 0 | 9 | 0 | 0 | 0 | 0 | 0 | 7 | 7 | 5 | | 1 | 0 | 0 | | 0 |
| | | | 0.50 | 0 | 0 | 0 | 0 | 0 | 0 | 0 | 2 | 0 | 0 | | 0 | | 0 | | 0 |
| | | | 0.25 | 0 | 0 | 0 | 0 | 0 | 0 | 0 | 0 | 0 | 0 | | 0 | | 0 | | 0 |
| CH(C₂H₅)₂ | CH₃ | C₄H₉-sec | 1.0 | 0 | 0 | 8 | 0 | 0 | 7 | 2 | 9 | 9 | 9 | | 0 | 0 | 0 | | 0 |
| | | | 0.50 | 0 | | 6 | 0 | | 0 | 0 | 8 | 9 | 8 | | 0 | 0 | 0 | | 0 |
| | | | 0.25 | 0 | 0 | 0 | 0 | 0 | 0 | 8 | 9 | 7 | | 0 | 0 | 0 | | 0 | |
| | | | 0.13 | 0 | | 0 | 0 | 0 | 0 | 0 | 0 | 7 | 2 | | 0 | 0 | 0 | | 0 |
| | | | 0.06 | 0 | 0 | 0 | 0 | 0 | 0 | 0 | 0 | 0 | 0 | | 0 | | 0 | | 0 |
| C₃H₇-i | CH₃ | C₃H₇-i | 1.0 | 7 | 9 | 7 | 0 | 0 | 7 | 5 | 9 | 9 | 9 | | 1 | 0 | 0 | | 0 |
| | | | 0.50 | 0 | 0 | 5 | 0 | 0 | 2 | 0 | 9 | 9 | 9 | | 0 | 0 | 0 | | 0 |
| | | | 0.25 | 0 | | 5 | 0 | 0 | 0 | 0 | 8 | 9 | 9 | | 0 | 0 | 0 | | 0 |
| | | | 0.13 | 0 | 0 | 0 | 0 | 0 | 0 | 0 | 8 | 9 | 8 | | 0 | 0 | 0 | | 0 |
| | | | 0.06 | 0 | 0 | 0 | 0 | 0 | 0 | 0 | 2 | 5 | 5 | | 0 | 0 | 0 | | 0 |
| | | | 0.03 | 0 | 0 | 0 | 0 | 0 | 0 | 0 | 0 | 2 | 2 | | 0 | 0 | 0 | | 0 |
| C₄H₉-sec | CH₃ | C₃H₇-i | 1.0 | 8 | 8 | 8 | 3 | 5 | 8 | 7 | 9 | 9 | 9 | | 5 | 0 | 0 | | 2 |
| | | | 0.50 | 7 | 8 | 7 | 0 | 3 | 8 | 2 | 9 | 9 | 9 | | 0 | 0 | 0 | | 0 |
| | | | 0.25 | 0 | 0 | 6 | 0 | 0 | 3 | 1 | 9 | 9 | 9 | | 0 | | 0 | | 0 |
| | | | 0.13 | 0 | 0 | 3 | 0 | 0 | 0 | 0 | 9 | 9 | 9 | | 0 | 0 | 0 | | 0 |
| | | | 0.06 | | | 0 | 0 | 0 | 0 | 0 | 9 | 9 | 6 | | 0 | 0 | 0 | | 0 |
| | | | 0.03 | 0 | 0 | 0 | 0 | 0 | 0 | 0 | 5 | 7 | 5 | | 0 | 0 | 0 | | 0 |
| +++CH(C₂H₅)₂ | CH₃ | C₂H₅ | 1.0 | 6.7 | 8.3 | 8 | 4.3 | 7.3 | 8 | 8.6 | 9 | 9 | 9 | 3.3 | 0.3 | 0 | 1 | | |
| | | | 0.5 | 4.6 | 7.3 | 8 | 1 | 5 | 7.6 | 7 | 9 | 9 | 9 | 1.3 | 0.3 | 0 | 0 | | |
| | | | 0.25 | 2.3 | 4.6 | 5.6 | 0 | 1.6 | 7.6 | 3.6 | 8.3 | 9 | 9 | 0.6 | 0 | 0 | 0 | | |
| | | | 0.13 | 1 | 4 | 4.3 | 0 | 0.6 | 5 | 1.3 | 6.6 | 9 | 7.6 | 0.3 | 0 | 0 | 0 | | |
| | | | 0.06 | 1 | 0 | 2.6 | 0 | 0.3 | 2.3 | 1 | 3 | 8 | 5.3 | 0 | 0 | 0 | 0 | | |
| | | | 0.03 | 0.6 | 0 | 1 | 0 | 0 | 1.6 | 0 | 1.6 | 7 | 3 | 0 | 0 | 0 | 0 | | |
| CH(CH₃)₂ | CH₃ | C₂H₅ | 1.0 | 6 | 9 | 7 | 7 | 0 | 8 | 2 | 9 | 9 | 9 | | 3 | 0 | | | 0 |
| | | | 0.5 | 0 | 9 | 2 | 0 | 0 | 3 | 0 | 9 | 9 | 9 | | 0 | | 0 | | 0 |
| | | | 0.25 | 0 | | 0 | 0 | 0 | 2 | 0 | 9 | 9 | 7 | | 0 | | 0 | | 0 |
| | | | 0.13 | 0 | | 0 | 0 | 0 | 0 | 0 | 9 | 9 | 7 | | 0 | 0 | 0 | | 0 |
| | | | 0.06 | 0 | 0 | 0 | 0 | 0 | 0 | 0 | 3 | 7 | 3 | | 0 | 0 | 0 | | 0 |
| | | | 0.03 | 0 | 0 | 0 | 0 | 0 | 0 | 0 | 0 | 3 | 0 | | 0 | | 0 | | 0 |
| CH(C₂H₅)CH₂Cl | CH₃ | Cl | 2.0 | | | | | | | | 9 | 9 | 9 | | | | | | |
| | | | 1.0 | | | | | | | | 8 | 9 | 9 | | | | | | |
| | | | 0.5 | | | | | | | | 9 | 9 | 9 | | | | | | |
| | | | 0.25 | | | | | | | | 7 | 9 | 6 | | | | | | |
| | | | 0.13 | | | | | | | | 6 | 7 | 5 | | | | | | |
| ***CH(C₂H₅)₂ | CH₃ | —CH(CH₃)₂ | 1.0 | 8.5 | 9 | 9 | 1.5 | 7 | 8.5 | 8 | 9 | 9 | 9 | 2 | 0 | 0 | 0 | | |
| | | | 0.5 | 5.5 | 8.5 | 9 | 0 | 4 | 7.5 | 5.5 | 9 | 9 | 9 | 1 | 0 | 0 | 0 | | |
| | | | 0.25 | 1 | 8 | 8 | 0 | 1 | 7.5 | 8.5 | 9 | 9 | 9 | 0 | 0 | 0 | 0 | | |
| | | | 0.13 | 0 | 5 | 5 | 0 | 1 | 3.5 | 1.5 | 6.5 | 9 | 7 | 0 | 0 | 0 | 0 | | |
| | | | 0.06 | 0 | 1 | 1.5 | 0 | 0 | 3.5 | 0.5 | 1 | 8 | 4 | 0 | 0 | 0 | 0 | | |
| | | | 0.03 | 0 | 0 | 0 | 0 | 0 | 0 | 0 | 0 | 6.5 | 2.5 | 0 | 0 | 0 | 0 | | |
| CH(C₂H₅)₂ | CH₃ | C₃H₇-n | 1.0 | 0 | 9 | 8 | 0 | 1 | 8 | 3 | 9 | 9 | 9 | | 0 | 0 | 0 | | 0 |
| | | | 0.5 | 0 | 9 | 7 | 0 | 0 | 6 | 0 | 9 | 9 | 9 | | 0 | 0 | 0 | | 0 |
| | | | 0.25 | 0 | 0 | 5 | 0 | 0 | 0 | 0 | 5 | 9 | 7 | | 0 | 0 | 0 | | 0 |
| | | | 0.13 | 0 | | 3 | 0 | 0 | 0 | 0 | 0 | 9 | 5 | | 0 | | 0 | | 0 |
| | | | 0.06 | 0 | 0 | 0 | 0 | 0 | 0 | 0 | 0 | 2 | 0 | | 0 | 0 | | | 0 |
| | | | 0.03 | 0 | | 0 | 0 | 0 | 0 | 0 | 0 | 3 | 0 | | 0 | 0 | | | 0 |
| CH(CH₃)C₂H₅ | CH₃ | C₂H₅ | 1.0 | 8 | 8 | 7 | 2 | 2 | 8 | 6 | 9 | 9 | 9 | | 2 | | 0 | | 5 |
| | | | 0.5 | 2 | 0 | 8 | 0 | 0 | 8 | 3 | 9 | 9 | 9 | | 0 | 0 | | | 0 |
| | | | 0.25 | 0 | | 5 | 0 | 0 | 7 | 0 | 9 | 9 | 9 | | 0 | 0 | 0 | | 0 |

TABLE XI-continued

Preemergence Herbicidal Evaluation of

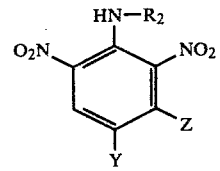

| Structure | | | Rate | Plant Species | | | | | | | | | | | | | | | |
|---|---|---|---|---|---|---|---|---|---|---|---|---|---|---|---|---|---|---|---|
| R₂ | Z | Y | lb/Acre | SE | MU | PI | RG | MG | TW | VL | BA | CR | GF | WO | CN | CO | SY | SB | RI |
| | | | 0.13 | 0 | 0 | 0 | 0 | 0 | 3 | 0 | 8 | 9 | 8 | | 0 | | 0 | | |
| | | | 0.06 | 0 | | | 0 | 0 | 0 | 0 | 6 | 9 | 0 | | 0 | | 0 | | 0 |
| | | | 0.03 | 0 | 0 | | 0 | 0 | 0 | 0 | 3 | 3 | 0 | | 0 | | 0 | | 0 |
| CH(CH₃)C₃H₇-n | CH₃ | Cl | 1.0 | | | 8 | | 4 | | 4 | 9 | 9 | 9 | 7 | 8 | 0 | 0 | | |
| | | | 0.5 | | | 8 | | 0 | | 2 | 9 | 9 | 8 | 7 | 8 | 0 | 0 | | |
| (−) | | | 0.25 | | | 7 | | 0 | | 0 | 7 | 9 | 8 | 4 | 0 | 0 | 0 | | |
| | | | 0.13 | | | 3 | | | | 0 | 5 | 8 | 8 | 4 | 0 | 0 | 0 | | |
| | | | 0.06 | | | 0 | | 0 | | 0 | 3 | 7 | 6 | 0 | 0 | 0 | 0 | | |
| CH(C₂H₅)C₄H₉-n | CH₃ | CH₃ | 4.0 | | | 8 | | 2 | | 3 | 8 | 9 | 8 | 0 | 0 | 0 | 0 | 5 | |
| | | | 2.0 | | | 7 | | 1 | | 1 | 7 | 9 | 2 | 0 | 0 | 0 | 0 | 5 | |
| | | | 1.0 | | | 6 | | 0 | | 0 | 7 | 8 | 0 | 0 | 0 | 0 | 0 | 2 | |
| | | | 0.5 | | | 5 | | 0 | | 0 | 5 | 6 | 0 | 0 | 0 | 0 | 0 | 0 | |
| | | | 0.25 | | | 0 | | 0 | | 0 | 3 | 2 | 0 | 0 | 0 | 0 | 0 | 0 | |

*Average of 10 to 15 tests
**Average of 2 to 3 Tests
***Average of two tests
+Single test
++Novel but not covered in proposed generic formula.
+++Average three tests

TABLE XII

Preemergence Herbicidal Evaluation of

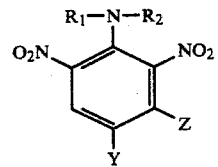

| Structure | | | | Rate lb/ | Plant Species | | | | | | | | | | | | | | |
|---|---|---|---|---|---|---|---|---|---|---|---|---|---|---|---|---|---|---|---|
| R₁ | R₂ | Z | Y | Acre | SE | MU | PI | RG | MG | TW | VL | BA | CR | GF | WO | CN | CO | SY | SB | RI |
| CH₃O | CH₃ | CH₂OCH₃ | C₂H₅ | 1.0 | 2 | 2 | 8 | 0 | 0 | 2 | 1 | 9 | 9 | 9 | | 3 | 0 | 0 | 6 |
| | | | | 0.50 | 0 | 2 | 2 | 0 | 0 | 1 | 0 | 9 | 9 | 9 | | 0 | 0 | 0 | 0 |
| | | | | 0.25 | 0 | | 0 | 0 | 0 | 0 | 0 | 8 | 9 | 9 | | 0 | 0 | 0 | 0 |
| | | | | 0.13 | | 0 | 0 | 0 | 0 | 0 | 0 | 5 | 9 | 5 | | 0 | 0 | 0 | 0 |
| | | | | 0.06 | 0 | 0 | 0 | 0 | 0 | 0 | 0 | 0 | 2 | 0 | | 0 | 0 | 0 | 0 |
| | | | | 0.03 | 0 | | 0 | 0 | 0 | 0 | 0 | 0 | 0 | 0 | | 0 | 0 | 0 | 0 |
| | | CH₂OCH₃ | C₂H₅ | 1.0 | 0 | | 0 | 0 | 0 | 0 | 0 | 9 | 9 | 9 | | 0 | 0 | 0 | 0 |
| | | | | 0.50 | 0 | | 0 | 0 | 0 | 0 | 0 | 8 | 9 | 9 | | 0 | 0 | 0 | 0 |
| | | | | 0.25 | 0 | | 0 | 0 | 0 | 0 | 0 | 7 | 9 | 8 | | 0 | 0 | 0 | 0 |
| | | | | 0.13 | 0 | 0 | 0 | 0 | 0 | 0 | 0 | 2 | 8 | 2 | | 0 | 0 | 0 | 0 |
| | | | | 0.06 | 0 | 0 | 0 | 0 | 0 | 0 | 0 | 0 | 6 | 0 | | 0 | 0 | 0 | 0 |
| | | | | 0.03 | 0 | 0 | 0 | 0 | 0 | 0 | 0 | 0 | 2 | 0 | | 0 | 0 | 0 | 0 |

TABLE XIII

Preemergence Herbicidal Evaluation of

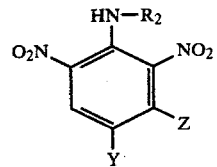

| Structure | | | Rate | Plant Species | | | | | | | | | | | | | | | |
|---|---|---|---|---|---|---|---|---|---|---|---|---|---|---|---|---|---|---|---|
| R₂ | Z | Y | lb/Acre | SE | MU | PI | RG | MG | TW | VL | BA | CR | GF | WO | CN | CO | SY | SB | RI |
| | | | 1.0 | 0 | 7 | 8 | 0 | 0 | 0 | 0 | 9 | 9 | 9 | | 0 | 0 | | | 6 |
| | | | 0.5 | 0 | 0 | 3 | 0 | 0 | 0 | 0 | 8 | 9 | 9 | | 0 | 0 | 0 | | 0 |
| CH(C₂H₅)₂ | CH₂OCH₃ | CN | 0.25 | 0 | | 0 | 0 | 0 | 0 | 0 | 2 | 9 | 8 | | 0 | 0 | 0 | | 0 |
| | | | 0.13 | 0 | 0 | 0 | 0 | 0 | 0 | 0 | 0 | 9 | 6 | | 0 | 0 | 0 | | 0 |
| | | | 0.06 | 0 | 0 | 0 | 0 | 0 | 0 | 0 | 0 | 9 | 0 | | 0 | 0 | 0 | | 0 |
| | | | 0.03 | 0 | | 0 | 0 | 0 | 0 | 0 | 0 | 2 | 0 | | 0 | 0 | 0 | | 0 |

TABLE XIV
Preemergence Herbicidal Evaluation of
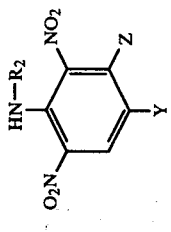
| Structure | | | Rate | Plant Species | | | | | | | | | | | | | | | | |
|---|---|---|---|---|---|---|---|---|---|---|---|---|---|---|---|---|---|---|---|---|
| $R_2$ | Z | Y | lb/Acre | SE | MU | PI | RG | MG | TW | VL | BA | CR | GF | WO | CN | CO | SY | SB | RI |
| $CH(C_2H_5)CH_2OCH_3$ | $CH_2OCH_3$ | $C_2H_5$ | 10.0 | 9 | 9 | 9 | 9 | 9 | 9 | 9 | 9 | 9 | 9 | 8 | 5 | 7 | 0 | | |
| | | | 1.0 | 7 | 8 | 9 | 0 | 2 | 9 | 9 | 9 | 9 | 9 | 5 | 8 | 0 | 0 | | |
| | | | 0.50 | 6 | 9 | 7 | 0 | 0 | 8 | 6 | 9 | 9 | 9 | 2 | 0 | 0 | 0 | | |
| | | | 0.25 | 2 | 3 | 6 | 0 | 0 | 7 | 3 | 9 | 9 | 9 | 0 | 0 | 0 | 0 | | |
| | | | 0.13 | 0 | 0 | 5 | 0 | 0 | 3 | 2 | 9 | 9 | 9 | 0 | 0 | 0 | 0 | | |
| | | | 0.06 | 0 | 0 | 9 | 9 | 8 | 0 | 9 | 9 | 9 | 9 | 9 | 7 | 0 | 2 | | |
| $CH(C_2H_5)CH_2OCH_3$ | $CH_2OCH_3$ | $CH_3$ | 10.0 | 9 | 9 | 9 | 9 | 2 | 9 | 9 | 9 | 9 | 9 | 2 | 3 | 0 | 0 | | |
| | | | 1.0 | 0 | 8 | 7 | 0 | 0 | 8 | 8 | 9 | 9 | 8 | 2 | 2 | 0 | 0 | | |
| | | | 0.50 | 0 | 0 | 5 | 0 | 0 | 2 | 2 | 2 | 2 | 7 | 2 | 2 | 0 | 0 | | |
| | | | 0.25 | 0 | 0 | 0 | 0 | 0 | 0 | 0 | 9 | 9 | 0 | 0 | 0 | 0 | 0 | | |
| | | | 0.13 | 0 | 0 | 0 | 0 | 0 | 0 | 0 | 9 | 9 | 0 | 0 | 0 | 0 | 0 | | |
| | | | 0.06 | 0 | 9 | 9 | 9 | 8 | 9 | 8 | 9 | 9 | 9 | 2 | 6 | 0 | 2 | | |
| $CH(CH_3)CH_2OCH_3$ | $CH_2OCH_3$ | $C_3H_7$-i | 10.0 | 9 | 9 | 9 | 7 | 7 | 7 | 8 | 9 | 9 | 9 | 2 | 0 | 0 | 2 | | |
| | | | 1.0 | 6 | 9 | 8 | 0 | 0 | 8 | 6 | 9 | 9 | 9 | 2 | 0 | 0 | 0 | | |
| | | | 0.50 | 6 | 5 | 6 | 0 | 0 | 7 | 5 | 9 | 9 | 8 | 1 | 0 | 0 | 0 | | |
| | | | 0.25 | 0 | 0 | 2 | 0 | 0 | 6 | 2 | 9 | 9 | 2 | 0 | 0 | 0 | 0 | | |
| | | | 0.13 | 0 | 0 | 1 | 0 | 0 | 5 | 0 | 7 | 7 | 1 | 0 | 0 | 0 | 0 | | |
| | | | 0.06 | 0 | 0 | 0 | 0 | 0 | 3 | 0 | 6 | 7 | 0 | 0 | 0 | 0 | 0 | | |
| $CH(CH_3)CH_2OCH_3$ | $CH_2OCH_3$ | $CH_3$ | 10.0 | 8 | 9 | 9 | 9 | 9 | 9 | 8 | 9 | 9 | 9 | 8 | 0 | 0 | 2 | | |
| | | | 1.0 | 6 | 3 | 7 | 0 | 0 | 7 | 6 | 9 | 9 | 9 | 2 | 0 | 0 | 2 | | |
| | | | 0.50 | 2 | 0 | 6 | 0 | 0 | 6 | 3 | 7 | 7 | 2 | 1 | 0 | 0 | 0 | | |
| | | | 0.25 | 2 | 0 | 1 | 0 | 0 | 5 | 1 | 6 | 6 | 1 | 0 | 0 | 0 | 0 | | |
| | | | 0.13 | 0 | 0 | 0 | 0 | 0 | 3 | 1 | 2 | 2 | 0 | 0 | 0 | 0 | 0 | | |
| | | | 0.06 | 0 | 0 | 0 | 0 | 0 | 1 | 0 | 0 | 0 | 0 | 0 | 0 | 0 | 0 | | |
| | | | 0.03 | 0 | 0 | 0 | 0 | 0 | 1 | 0 | 9 | 9 | 0 | 0 | 0 | 0 | 0 | | |
| $CH(CH_3)CH_2OCH_3$ | $CH_2OCH_3$ | $C_2H_5$ | 10.0 | 8 | 9 | 9 | 9 | 9 | 9 | 9 | 9 | 9 | 9 | 0 | 0 | 0 | 0 | | |
| | | | 1.0 | 2 | 9 | 9 | 0 | 8 | 8 | 8 | 9 | 9 | 8 | 0 | 0 | 0 | 0 | | |
| | | | 0.50 | 0 | 2 | 2 | 0 | 0 | 3 | 7 | 6 | 6 | 2 | 0 | 0 | 0 | 0 | | |
| | | | 0.25 | 0 | 0 | 2 | 0 | 0 | 3 | 3 | 2 | 2 | 1 | 0 | 0 | 0 | 0 | | |
| | | | 0.13 | 0 | 0 | 2 | 0 | 0 | 1 | 0 | 5 | 5 | 0 | 0 | 0 | 0 | 0 | | |
| | | | 0.06 | 0 | 0 | 0 | 0 | 0 | 0 | 0 | 2 | 2 | 0 | 0 | 0 | 0 | 0 | | |
| | | | 0.03 | 0 | 0 | 0 | 0 | 0 | 0 | 0 | 0 | 0 | 0 | 0 | 0 | 0 | 0 | | |
| $CH(CH_3)CH_2CH_2OCH_3$ | $CH_2OCH_3$ | Cl | 10.0 | 9 | 9 | 9 | 9 | 8 | 9 | 8 | 9 | 9 | 9 | 0 | 0 | 0 | 0 | | |
| | | | 1.0 | 0 | 9 | 0 | 0 | 0 | 7 | 0 | 0 | 0 | 3 | 0 | 0 | 0 | 0 | | |
| | | | 0.50 | 0 | 9 | 9 | 9 | 8 | 9 | 8 | 9 | 9 | 9 | 0 | 0 | 0 | 0 | | |
| | | | 0.25 | 9 | 9 | 9 | 9 | 0 | 9 | 0 | 0 | 0 | 0 | 0 | 0 | 0 | 0 | | |
| | | | 10.0 | 0 | 9 | 0 | 0 | 0 | 9 | 8 | 9 | 9 | 9 | 0 | 0 | 0 | 0 | | |
| | | | 1.0 | 0 | 9 | 9 | 0 | 0 | 7 | 3 | 9 | 9 | 0 | 6 | 0 | 0 | 0 | | |

TABLE XIV-continued
Preemergence Herbicidal Evaluation of
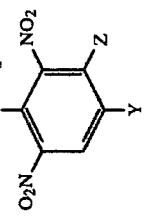
| Structure | | | Rate | Plant Species | | | | | | | | | | | | | | | | |
|---|---|---|---|---|---|---|---|---|---|---|---|---|---|---|---|---|---|---|---|---|
| R2 | Z | Y | lb/Acre | SE | MU | PI | RG | MG | TW | VL | BA | CR | GF | WO | CN | CO | SY | SB | RI |
| CH(CH3)CH2CH2OCH3 | CH2OCH3 | C3H7-i | 0.50 | 0 | 9 | 9 | 0 | 0 | 2 | 2 | 9 | 9 | 9 | 0 | 3 | 0 | 0 | | |
| | | | 0.25 | 0 | 8 | 7 | 0 | 0 | 0 | 0 | 9 | 9 | 9 | 0 | 0 | 0 | 0 | | |
| | | | 0.13 | 0 | 8 | 2 | 0 | 0 | 0 | 0 | 9 | 9 | 6 | 0 | 0 | 0 | 0 | | |
| | | | 0.06 | 0 | | 0 | 0 | 0 | 0 | 0 | 8 | 8 | 3 | 0 | 0 | 0 | 0 | | |
| | | | 0.03 | 8 | | 0 | 8 | 8 | 8 | 8 | 9 | 9 | 9 | 0 | 0 | 0 | 0 | | |
| CH(CH3)CH2OCH3 | CH2OCH3 | Cl | 10.0 | 0 | 9 | 9 | 0 | 0 | 0 | 0 | 9 | 9 | 9 | 0 | 0 | 0 | 0 | | |
| | | | 1.0 | 0 | 0 | 7 | 0 | 0 | 0 | 0 | 3 | 9 | 8 | 0 | 0 | 0 | 0 | | |
| | | | 0.50 | 0 | 0 | 0 | 0 | 0 | 0 | 0 | 2 | 6 | 0 | 0 | 0 | 0 | 0 | | |
| | | | 0.13 | 0 | 0 | 0 | 0 | 0 | 0 | 0 | 0 | 3 | 0 | 0 | 0 | 0 | 0 | | |
| | | | 0.06 | 0 | | 0 | 0 | 0 | 0 | 0 | 0 | 0 | 0 | 0 | 0 | 0 | 0 | | |
| | | | 0.03 | 8 | 9 | 9 | 9 | 8 | 8 | 8 | 9 | 9 | 9 | 0 | 5 | 0 | 0 | | |
| CH(C2H5)CH2OCH3 | CH2OCH3 | C3H7-i | 10.0 | 8 | 9 | 9 | 3 | 1 | 8 | 5 | 9 | 9 | 9 | 0 | 8 | 0 | 0 | | o |
| | | | 1.0 | 5 | 9 | 9 | 3 | 1 | 7 | 3 | 9 | 9 | 9 | 2 | 3 | 0 | 0 | | o |
| | | | 0.50 | 5 | 0 | 8 | 0 | 1 | 5 | 2 | 9 | 9 | 6 | 5 | 1 | 0 | 0 | | o |
| | | | 0.25 | 0 | 0 | 7 | 0 | 0 | 2 | 0 | 8 | 8 | 3 | 0 | 0 | 0 | 0 | | o |
| | | | 0.13 | 0 | 0 | 2 | 0 | 0 | 0 | 0 | 6 | 6 | 3 | 0 | 0 | 0 | 0 | | o |
| | | | 0.06 | 0 | 0 | 9 | 6 | 8 | 0 | 8 | 9 | 9 | 9 | 0 | 0 | 0 | 0 | | o |
| | | | 0.03 | 0 | 9 | 8 | 0 | 8 | 9 | 8 | 9 | 9 | 9 | 0 | 0 | 0 | 0 | | o |
| CH(CH3)CH2OCH3 | CH3 | Cl | 10.0 | | | 8 | | 7 | 8 | 7 | 9 | 9 | 9 | | | | | | |
| CH(C2H5)CH2OCH3 | CH3 | Cl | 4.0 | | | 7 | | 5 | 7 | 5 | 8 | 9 | 9 | 9 | 5 | 1 | 5 | 6 | |
| | | | 2.0 | | | 5 | | 0 | 5 | 5 | 8 | 9 | 9 | 2 | 8 | 0 | 0 | 3 | |
| | | | 1.0 | | | 3 | | 0 | 2 | 3 | 6 | 8 | 6 | 5 | 3 | 0 | 0 | 3 | |
| | | | 0.50 | | | 0 | 0 | 0 | 0 | 0 | 3 | 5 | 3 | 3 | 1 | 0 | 0 | 1 | |
| | | | 0.25 | | 8 | 9 | | 0 | 0 | 8 | 9 | 9 | 9 | 5 | 0 | 0 | 0 | | |
| CH(C2H5)CH2OCH3 | CH3 | Cl | 10.0 | | | 9 | | 8 | 9 | 6 | 9 | 9 | 9 | 3 | 6 | 5 | 6 | 8 | |
| (—) | | | 4.0 | | | 8 | | 5 | 8 | 3 | 9 | 9 | 9 | 3 | 1 | 0 | 1 | 7 | |
| | | | 2.0 | | | 7 | | 0 | 0 | 0 | 8 | 9 | 8 | 0 | 0 | 0 | 0 | 5 | |
| | | | 1.0 | | | 6 | | 0 | 0 | 0 | 7 | 9 | 8 | 0 | 0 | 0 | 0 | 1 | |
| | | | 0.50 | | | 1 | | 0 | 0 | 0 | 3 | 8 | 6 | 0 | 0 | 0 | 0 | 0 | |
| | | | 0.25 | | | 1 | | 0 | 0 | 0 | 3 | 8 | 6 | 0 | 0 | 0 | 0 | 0 | |

EXAMPLE

Postemergence Herbicidal Evaluation of Test Compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about 2 weeks The test compounds are dispersed in 50/50 acetone/water mixtures containing 0.5% TWEEN[(R)] 20, a polyoxyethylene sorbitan monolaurate surfactant of Atlas Chemical Industries, in sufficient quantity to provide the equivalent of from about 0.03 lb to 10 lbs. per acre of active compound when applied to the plants through a spray nozzle operating at 40 psi for a predetermined time. After spraying, the plants are placed on greenhouse benches and are cared for in the usual manner, commensurate with conventional greenhouse practices. From 4 to 13 weeks after treatment, the seedling plants are examined and rated according to the rating system provided below. The data obtained are reported in Table XII below.

| Rating System: | % Difference in Growth from the Check* |
|---|---|
| 0 - No effect | 0 |
| 1 - Possible effect | 1–10 |
| 2 - Slight effect | 11–25 |
| 3 - Moderate effect | 26–40 |
| 4 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation, but with an over-all effect less than a 5 on the rating scale. | |

Plant Abbreviations:
- SE - Sesbania (*Sesbania exaltata*)
- MU - Mustard (*Brassica kaber*)
- PI - Pigweed (*Amaranthus retroflexus*)
- RW - Ragweed (*Ambrosia artemisiifolia*)
- MG - Morningglory (*Ipomoea purpurea*)
- BA - Barnyardgrass (*Echinochloa crusgalli*)
- CR - Crabgrass (*Digitaria sanguinalis*)
- FO - Green foxtail (*Setaria viridis*)
- WO - Wild oats (*Avena fatua*)
- TW - Teaweed (*Sida spinosa*)
- VL - Velvetleaf (*Abutilon theophrasti*)

*Based on visual determination of stand, size, vigor, chlorosis, growth malformation and over-all plant appearance.

TABLE XV

Postemergence Herbicidal Evaluation of

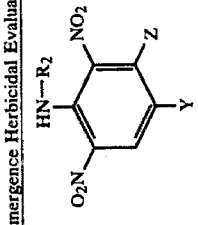

| Structure | | | Rate | Plant Species | | | | | | | | | | | | | | |
|---|---|---|---|---|---|---|---|---|---|---|---|---|---|---|---|---|---|---|
| R₂ | Z | Y | lb/Acre | SE | MU | PI | RG | MG | TW | VL | BA | CR | GF | WO | CN | CO | SY | SB | RI |
| *CH(C₂H₅)₂ | CH₂OCH₃ | CH₃ | 1.0 | | 8.5 | | | 6.3 | 7.3 | 7.8 | 7.7 | 8 | 5.1 | 1.4 | 0 | 5.6 | 3.6 | | 0 |
| | | | 0.50 | | 8.3 | | | 4.8 | 6.5 | 7.2 | 6.5 | 7.2 | 3.5 | 0 | 0 | 5.5 | 2.8 | | 0 |
| | | | 0.25 | | 7.3 | | | 2.6 | 4.3 | 6.7 | 4.3 | 6.2 | 2 | 0 | 0 | 5.5 | 36 | | 0 |
| | | | 0.13 | | 6 | | | 1 | 5.3 | 5.6 | 4.8 | 5 | .3 | 0 | 0 | 4.8 | 1.8 | | 0 |
| | | | 0.06 | | 2.5 | | | 0 | 5 | 6 | 1 | 3.5 | 1.5 | 0 | 0 | 3.5 | 2 | | 0 |
| C₄H₅-sec | CH₂OCH₃ | CH₃ | 1.0 | | 2 | | | 3 | 6 | 8 | 7 | 7 | 2 | 0 | 0 | 3 | 0 | | 0 |
| | | | 0.50 | | 0 | | | 0 | 3 | 5 | 6 | 5 | 1 | 0 | 0 | 1 | 0 | | 0 |
| | | | 0.25 | | 0 | | | 0 | 0 | 0 | 2 | 3 | 0 | 0 | 0 | 1 | 0 | | 0 |
| | | | 0.13 | | 0 | | | 0 | 0 | 2 | 0 | 1 | 0 | 0 | 0 | 0 | 0 | | 0 |
| | | | 0.06 | | 0 | | | 0 | 0 | 0 | 0 | 0 | 0 | 0 | 0 | 0 | 0 | | 0 |
| CH(C₂H₅)₂ | CH₂OCH₃ | C₃H₇-i | 0.03 | | 0 | | | 0 | 0 | 0 | 0 | 0 | 0 | 0 | 0 | 0 | 0 | | 0 |
| | | | 10.0 | 4 | 4 | 4 | 4 | 4 | 4 | 4 | 4 | 4 | 4 | 6 | | 4 | | | |
| *Average of Two to 6 Tests | | | | | | | | | | | | | | | | | | | |
| C₃H₇-i | CH₂OCH₃ | CH₃ | 1.0 | | 0 | | | 0 | 3 | 5 | 0 | 5 | 3 | 0 | 0 | 2 | 0 | | 0 |
| | | | 0.50 | | 0 | | | 0 | 1 | 3 | 0 | 1 | 1 | 0 | 0 | 2 | 0 | | 0 |
| | | | 0.25 | | 0 | | | 0 | 0 | 2 | 2 | 0 | 1 | 0 | 0 | 1 | 1 | | 0 |
| | | | 0.13 | | 0 | | | 0 | 0 | 1 | 1 | 0 | 0 | 0 | 0 | 0 | 1 | | 0 |
| | | | 0.06 | | 8 | | | 0 | 5 | 0 | 2 | 3 | 0 | 0 | 0 | 0 | 1 | | 0 |
| CH(C₂H₅)₂ | CH₂OCH₃ | Cl | 1.0 | | 0 | | | 3 | 3 | 8 | 3 | 1 | 0 | 0 | 0 | 2 | 1 | | 0 |
| | | | 0.50 | | 0 | | | 0 | 1 | 6 | 6 | 1 | 0 | 0 | 0 | 2 | 1 | | 0 |
| | | | 0.25 | | 9 | | | 0 | 5 | 5 | 7 | 0 | 0 | 0 | 0 | 1 | 1 | | 0 |
| CH(CH₃)C₃H₇-n | CH₂OCH₃ | Cl | 1.0 | | 6 | | | 0 | 5 | 5 | 7 | 0 | 0 | 0 | 0 | 0 | 1 | | 0 |
| | | | 0.50 | | 0 | | | 5 | 5 | 5 | 0 | 5 | 3 | 0 | 0 | 6 | 7 | | 0 |
| | | | 0.25 | | 8 | | | 5 | 7 | 7 | 8 | 7 | 3 | 7 | 0 | 5 | 7 | | 0 |
| CH(C₂H₅)₂ | CH₂OCH₃ | C₂H₅ | 1.0 | | 8 | | | 6 | 6 | 7 | 6 | 7 | 2 | 1 | 0 | 3 | 5 | | 0 |
| | | | 0.50 | | 8 | | | 5 | 5 | 7 | 8 | 7 | 0 | 0 | 0 | 1 | 3 | | 0 |
| | | | 0.25 | | 6 | | | 2 | 6 | 7 | 0 | 0 | 0 | 0 | 0 | 0 | 0 | | 0 |
| C₃H₇-i | CH₂OCH₃ | C₂H₅ | 1.0 | | 8 | | | 5 | 5 | 7 | 5 | 0 | 2 | 0 | 0 | 5 | 3 | | 0 |
| | | | 0.50 | | 5 | | | 6 | 6 | 6 | 3 | 0 | 1 | 0 | 0 | 5 | 3 | | 0 |
| | | | 0.25 | | 3 | | | 5 | 5 | 7 | 3 | 0 | 0 | 0 | 0 | 5 | 0 | | 0 |
| CH(CH₃)C₃H₇-n | CH₂OCH₃ | C₂H₅ | 1.0 | | 3 | | | 3 | 6 | 6 | 0 | 0 | 2 | 5 | 0 | 5 | 3 | | 0 |
| | | | 0.50 | | 8 | | | 3 | 6 | 7 | 7 | 0 | 0 | 0 | 0 | 5 | 0 | | 0 |
| | | | 0.25 | | 4 | | | 4 | 8 | 8 | 4 | 7 | 0 | 7 | 0 | 5 | 3 | | 0 |
| CH(C₂H₅)C₃H₇-n | CH₂OCH₃ | C₂H₅ | 1.0 | | 4 | | | 4 | 2 | 4 | 4 | 4 | 2 | 5 | 0 | 5 | 0 | | 0 |
| | | | 0.50 | 4 | | | | | | | | | | | | | | | |
| CH(C₃H₇-n)₂ | CH₂OCH₃ | C₂H₅ | 0.25 | | | | | | | | | | | | | | | | |
| C₄H₉-i | CH₂OCH₃ | C₂H₅ | 10.0 | 4 | 8 | 8 | 4 | 4 | 6 | 4 | 4 | 4 | 4 | 2 | 0 | 5 | — | | 0 |
| CH(CH₃)CH₂C₃H₇-i | CH₂OCH₃ | C₂H₅ | 10.0 | 4 | 4 | 4 | 0 | 4 | 2 | 5 | 4 | 4 | 4 | 2 | 0 | 5 | — | | 0 |
| *C₃H₇-i | CH₂OCH₃ | C₃H₇-i | 10.0 | 5 | 7 | 4 | 0 | 4 | 5 | 6 | 4 | 6.5 | 5 | 5.5 | 0 | 5 | 0 | | 0 |

*Average of Two to 6 Tests

TABLE XV-continued

Postemergence Herbicidal Evaluation of

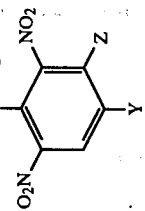

| Structure | | | Rate | Plant Species | | | | | | | | | | | | | | | | |
|---|---|---|---|---|---|---|---|---|---|---|---|---|---|---|---|---|---|---|---|---|
| R₂ | Z | Y | lb/Acre | SE | MU | PI | RG | MG | TW | VL | BA | CR | GF | WO | CN | CO | SY | SB | RI |
| C₃H₇-i | CH₂OC₂H₅ | Cl | 10.0 | 0 | 0 | 0 | 0 | 4 | 4 | 4 | 0 | 0 | 0 | 0 | | | | | |
| *CH₂CH=CH₂ | CH₂OCH₃ | C₂H₅ | 10.0 | 3 | 4.5 | 3 | | 5 | 3 | 4 | 6 | 6 | 5.5 | 5 | | | | | |
| *CH(C₃H₇-n)₂ | CH₂OCH₃ | CH₃ | 10.0 | 5.5 | 5.5 | 5.5 | | | 5 | 5 | 5.5 | 6 | 5.5 | 6.5 | 5.5 | | | | |
| *CH(CH₃)C₄H₉-n | CH₂OCH₃ | CH₃ | 10.0 | 5.5 | 6 | 5.5 | | 3 | 6 | 6 | 6 | 5.5 | 6 | 4.5 | | | | | |
| *C₄H₉-sec | CH₂OCH₃ | C₂H₅ | 10.0 | 6 | 6 | 5 | | 5 | 5.5 | 6.5 | 6 | 6 | 6.5 | 6 | | | | | |
| *CH(CH₃)C₃H₇-n | CH₂OCH₃ | CH₃ | 10.0 | 6 | 6 | 5.5 | | 5 | 6 | 5.5 | 6 | 5.5 | 6 | 5.5 | | | | | |
| *CH(C₂H₅)C₃H₇-n | CH₂OCH₃ | CH₃ | 10.0 | 6 | 6 | 5 | 0 | 0 | 5.5 | 5 | 6 | 6 | 6 | 6 | 5.5 | | | | |
| *CH(CH₃)C₃H₇-i | CH₂OCH₃ | CH₃ | 10.0 | | 6 | 4.5 | | 5 | 5 | 6 | 6 | 6 | 6 | 5.5 | | | | | |
| C₄H₉-sec | CH₂OCH₃ | Cl | 10.0 | 2 | 4 | 2 | 0 | 3 | 7 | 7 | 7 | 4 | 4 | 4 | | | | | |
| *CH(CH₃)CH₂Cl | CH₂OCH₃ | C₂H₅ | 10.0 | | 5.5 | 5.5 | | | 5.5 | 5.5 | 5.5 | 5.5 | 6.5 | 5.5 | | | | | |
| CH(C₂H₅)CH₂Cl | CH₂OCH₃ | CH₃ | 10.0 | 5 | 7 | 6 | 3 | 0 | 7 | 4 | 7 | 7 | 7 | 4 | | | | | |
| CH(CH₃)C₃H₇-n | CH₂OCH₃ | C₃H₇-i | 10.0 | 4 | 4 | 4 | 4 | 4 | 4 | 4 | 7 | 7 | 7 | 7 | | | | | |
| CH(C₂H₅)CH₂Cl | CH₂OCH₃ | C₂H₅ | 10.0 | 4 | 4 | 4 | 4 | 4 | 4 | 4 | 7 | 7 | 7 | 7 | | | | | |
| CH(C₂H₅)₂ | CH₂OCH₃ | C₄H₉-sec | 10.0 | 4 | 7 | 4 | 4 | 4 | 4 | 4 | 7 | 7 | 7 | 6 | | | | | |
| C₄H₉-i | CH₂OCH₃ | CH₃ | 10.0 | 4 | 4 | 0 | 4 | 0 | 4 | 7 | 9 | 8 | 4 | | | | | | |
| CH(C₂H₅)CH₂Cl | CH₂OCH₃ | C₃H₇-i | 10.0 | 3 | 4 | 4 | 4 | 4 | 4 | 4 | 4 | 4 | 4 | 4 | | | | | |
| CH(CH₃)CHClCH₃ | CH₂OCH₃ | CH₃ | 10.0 | | | | | | | | | | | | | | | | |

*Average of Two Tests

We claim:

1. A method for the preemergence control of undesirable plant species comprising applying to soil containing seeds of the undesirable plant species a herbicidally effective amount of a compound of the formula:

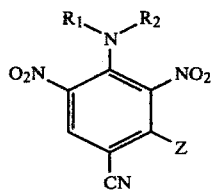

wherein:
- Z is alkyl $C_1$-$C_4$, alkenyl $C_2$-$C_4$ or monosubstituted alkyl $C_1$-$C_4$ where the substituent is halogen, alkoxy $C_1$-$C_4$ or —$NR_3R_4$;
- $R_1$ is hydrogen, alkyl $C_1$-$C_6$, alkenyl $C_2$-$C_6$ or alkynyl $C_2$-$C_6$;
- $R_2$ is alkyl $C_2$-$C_7$ (straight, branched or cyclo), alkenyl $C_2$-$C_6$, alkynyl $C_2$-$C_6$, or monosubstituted alkyl $C_1$-$C_4$ where the substituent is halogen or alkoxy $C_1$-$C_4$; and
- $R_3$ and $R_4$ each represent hydrogen or alkyl $C_1$-$C_4$.

2. A method according to claim 1, wherein the compound is of the formula:

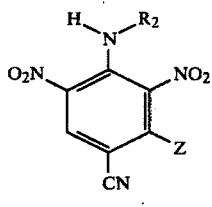

wherein:
Z is $CH_3$ or —$CH_2OCH_3$; and
$R_2$ is secondary $C_3$-$C_5$ alkyl.

3. A method according to claim 2, wherein the compound is 4-cyano-N-(sec-butyl)-2,6-dinitro-m-toluidine.

4. A method according to claim 2, wherein the compound is 4-cyano-N-(1-ethylpropyl)-α-methoxy-2,6-dinitro-m-toluidine.

5. A method according to claim 2, wherein the compound is 4-cyano-N-(1-ethylpropyl)-2,6-dinitro-m-toluidine.

6. A method according to claim 2, wherein the compound is 4-cyano-N-(1-methylbutyl)-2,6-dinitro-m-toluidine.

7. A preemergence herbicidal composition comprising an admixture of an inert herbicidal adjuvant and a herbicidally effective amount of a compound of the formula:

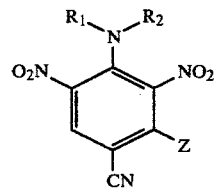

wherein:
- Z is alkyl $C_1$-$C_4$, alkenyl $C_2$-$C_4$ or monosubstituted alkyl $C_1$-$C_4$ where the substituent is halogen, alkoxy $C_1$-$C_4$ or —$NR_3R_4$;
- $R_1$ is hydrogen, alkyl $C_1$-$C_6$, alkenyl $C_2$-$C_6$ or alkynyl $C_2$-$C_6$;
- $R_2$ is alkyl $C_2$-$C_7$ (straight, branched or cyclo), alkenyl $C_2$-$C_6$, alkynyl $C_2$-$C_6$, or monosubstituted alkyl $C_1$-$C_4$ where the substituent is halogen or alkoxy $C_1$-$C_4$;

and
$R_3$ and $R_4$ each represent hydrogen or alkyl.

* * * * *